(12) United States Patent
Cui et al.

(10) Patent No.: US 7,858,643 B2
(45) Date of Patent: Dec. 28, 2010

(54) ENANTIOMERICALLY PURE AMINOHETEROARYL COMPOUNDS AS PROTEIN KINASE INHIBITORS

(75) Inventors: Jingrong Jean Cui, San Diego, CA (US); Lee Andrew Funk, Oceanside, CA (US); Lei Jia, San Diego, CA (US); Pei-Pei Kung, San Diego, CA (US); Jerry Jialun Meng, San Diego, CA (US); Mitchell David Nambu, San Diego, CA (US); Mason Alan Pairish, San Diego, CA (US); Hong Shen, San Diego, CA (US); Michelle Tran-Dube, La Jolla, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 1504 days.

(21) Appl. No.: 11/212,331

(22) Filed: Aug. 26, 2005

(65) Prior Publication Data

US 2006/0046991 A1 Mar. 2, 2006

Related U.S. Application Data

(60) Provisional application No. 60/605,086, filed on Aug. 26, 2004.

(51) Int. Cl.
| C07D 213/65 | (2006.01) |
| C07D 401/14 | (2006.01) |
| A61K 31/4412 | (2006.01) |
| C07D 401/04 | (2006.01) |
| A61K 31/496 | (2006.01) |
| A61K 31/4465 | (2006.01) |

(52) U.S. Cl. .................. 514/318; 514/253.12; 514/341; 514/349; 544/360; 546/275.4; 546/297; 546/194

(58) Field of Classification Search .................. 544/360; 546/275.4, 297, 194; 514/253.12, 318, 341, 514/349
See application file for complete search history.

(56) References Cited

U.S. PATENT DOCUMENTS

| 5,587,458 | A | 12/1996 | King et al. |
| 5,747,498 | A | 5/1998 | Schnur et al. |
| 5,792,783 | A | 8/1998 | Tang et al. |
| 5,834,504 | A | 11/1998 | Tang et al. |
| 5,861,510 | A | 1/1999 | Piscopio et al. |
| 5,863,949 | A | 1/1999 | Robinson et al. |
| 5,877,305 | A | 3/1999 | Huston et al. |
| 5,883,113 | A | 3/1999 | Tang et al. |
| 5,886,020 | A | 3/1999 | Tang et al. |
| 6,071,935 | A | 6/2000 | Lyssikatos |
| 6,080,769 | A | 6/2000 | Lyssikatos et al. |
| 6,106,864 | A | 8/2000 | Dolan et al. |
| 6,150,377 | A | 11/2000 | Lyssikatos et al. |
| 6,194,438 | B1 | 2/2001 | Yang et al. |
| 6,258,824 | B1 | 7/2001 | Yang |
| 6,284,764 | B1 | 9/2001 | Kath et al. |
| 6,465,449 | B1 | 10/2002 | Kath et al. |
| 6,479,513 | B2 | 11/2002 | Yang |
| 6,495,564 | B1 | 12/2002 | Lyssikatos et al. |
| 6,586,447 | B1 | 7/2003 | Lyssikatos et al. |
| 6,596,735 | B1 | 7/2003 | Yang |
| 6,682,736 | B1 | 1/2004 | Hanson et al. |
| 7,230,098 | B2 * | 6/2007 | Cui et al. ...................... 544/60 |
| 7,465,842 | B2 * | 12/2008 | Kung et al. .................. 570/126 |
| 7,585,853 | B2 | 9/2009 | Berg et al. |
| 2003/0166675 | A1 | 9/2003 | Yang |
| 2004/0186113 | A1 | 9/2004 | Berg et al. |
| 2005/0009840 | A1 | 1/2005 | Cui et al. |
| 2005/0227997 | A1 | 10/2005 | Noe et al. |
| 2006/0052396 | A1 | 3/2006 | Berg et al. |
| 2006/0063782 | A1 | 3/2006 | Murray et al. |
| 2006/0128724 | A1 * | 6/2006 | Cui et al. ................ 514/255.05 |
| 2006/0178374 | A1 * | 8/2006 | Cui et al. ................ 514/255.05 |
| 2007/0072874 | A1 * | 3/2007 | Cui et al. ................ 514/255.05 |
| 2008/0293769 | A1 * | 11/2008 | Cui et al. .................... 514/318 |

FOREIGN PATENT DOCUMENTS

| EP | 606046 | 7/1994 |
| EP | 780386 | 6/1997 |
| EP | 0 818 442 A2 | 7/1997 |
| EP | 0 952 148 B1 | 3/1999 |
| EP | 1 084 114 B1 | 5/1999 |
| EP | 931788 | 7/1999 |

(Continued)

OTHER PUBLICATIONS

U.S. Appl. No. 60/168,217 Equiv to WO 01/40217, Nov. 30, 1999, Pfizer Products Inc.

(Continued)

Primary Examiner—Susanna Moore
(74) Attorney, Agent, or Firm—Jeffrey H. Tidwell; Stephen D. Prodnuk; Vincent P. Liptak

(57) ABSTRACT

Enantiomerically pure compound of formula 1

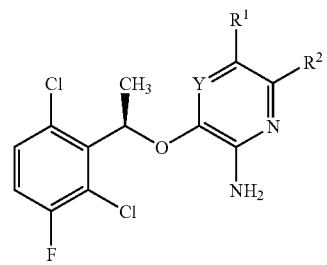

are provided, as well as methods for their synthesis and use. Preferred compounds are potent inhibitors of the c-Met protein kinase, and are useful in the treatment of abnormal cell growth disorders, such as cancers.

2 Claims, No Drawings

FOREIGN PATENT DOCUMENTS

| | | |
|---|---|---|
| EP | 1 004 578 B1 | 10/1999 |
| GB | 9912961.1 | 8/1999 |
| WO | WO 90/05719 | 5/1990 |
| WO | WO 91/11172 | 8/1991 |
| WO | WO 94/02518 | 2/1994 |
| WO | WO 95/19970 | 7/1995 |
| WO | WO 95/21613 | 8/1995 |
| WO | WO 96/27583 | 9/1996 |
| WO | WO 96/33172 | 10/1996 |
| WO | WO 97/13760 | 4/1997 |
| WO | WO 97/22596 | 6/1997 |
| WO | WO 97/32856 | 9/1997 |
| WO | WO 98/02424 | 1/1998 |
| WO | WO 98/02434 | 1/1998 |
| WO | WO 98/02437 | 1/1998 |
| WO | WO 98/02438 | 1/1998 |
| WO | WO 98/03516 | 1/1998 |
| WO | WO 98/07697 | 2/1998 |
| WO | WO 98/14451 | 4/1998 |
| WO | PCT/IB98/01113 | 7/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 98/50356 | 11/1998 |
| WO | WO 98/54093 | 12/1998 |
| WO | WO 98/55148 | 12/1998 |
| WO | WO 99/10349 | 3/1999 |
| WO | WO 99/16755 | 4/1999 |
| WO | WO 99/24440 | 5/1999 |
| WO | WO 99/29667 | 6/1999 |
| WO | WO 99/35132 | 7/1999 |
| WO | WO 99/35146 | 7/1999 |
| WO | WO 99/52889 | 10/1999 |
| WO | WO 99/52910 | 10/1999 |
| WO | WO 99/61422 | 12/1999 |
| WO | WO 00/35298 | 6/2000 |
| WO | WO 00/37107 | 6/2000 |
| WO | WO 00/38665 | 7/2000 |
| WO | WO 00/38715 | 7/2000 |
| WO | WO 00/38716 | 7/2000 |
| WO | WO 00/38717 | 7/2000 |
| WO | WO 00/38718 | 7/2000 |
| WO | WO 00/38719 | 7/2000 |
| WO | WO 00/38730 | 7/2000 |
| WO | WO 00/38786 | 7/2000 |
| WO | WO 03/004472 A1 | 1/2003 |
| WO | WO 03/004475 A1 | 1/2003 |
| WO | WO 2004/004720 A1 | 1/2004 |
| WO | WO 2004/055005 A1 | 7/2004 |
| WO | WO2004/076412 | 9/2004 |
| WO | WO 2005/002673 | 1/2005 |
| WO | WO2006/021886 | 3/2006 |

OTHER PUBLICATIONS

Finnin, B., et al., "Transdermal Penetration Enhancers: Applications, Limitations, and Potential," *Journal of Pharmaceutical Sciences*, 1999, 955-958, vol. 88, No. 10.

Haleblian, J., et al., "Characterization of Habits and Crystalline Modification of Solids and Their Pharmaceutical Applications," *Journal of Pharmaceutical Sciences*, 1975, 1269-1288, vol. 64, No. 8.

Jiang, W., et al., "Hypatocyte Growth Factor/Scatter Factor, Its Molecular, Cellular and Clinical Implications in Cancer," *Critical Revues in Oncology Hematology*, 1999, 209-248, vol. 29.

Ma, P., et al., "c-MET: Structure, Functions and Potential for Therapeutic Inhibition," *Cancer Metastasis Reviews*, 2003, 309-325, vol. 22.

Ma, P., et al., "*c-MET* Mutational Analysis in Small Cell Lung Cancer: Juxtamembrane Domain Mutations Regulating Cytoskeletal Functions," *Cancer Research*, 2003, 6272-6281, vol. 63.

Maulik, G., et al., "Role of the Hepatocyte Growth Factor Receptor, *c-MET*, in Oncogenesis and Potential for Therapeutic Inhibition," *Cytokine & Growth Factor Reviews*, 2002, 41-59, vol. 13.

Technikova-Dobrova, Z., et al., "Spectrophotometric Determination of Functional Characteristics of Protein Kinases With Coupled Enzymatic Assay," 1991, FEBS Lett., 69-72, vol. 292, No. 1,2.

Verma, R., et al., "Current Status of Drug Delivery Technologies and Future Directions," *Pharmaceutical Technology On-line*, 2001, 1-14, vol. 25, No. 2.

Voller, et al., "Enzyme-Linked Immunosorbent Assay," *Manual of Clinical Immunology 2 Edition*, 359-371, Rose And Friedman, Am. Soc. of Microbiology, Washington, D. C., 1980.

Sawyer, T., "Cancer Metastatis Therapeutic Targets and Drug Discovery: Emerging Small-Molecule Protein Kinase Inhibitors," *Expert Opinion on Investigational Drugs*, 2004, 1-19, vol. 13, No. 1.

* cited by examiner

ENANTIOMERICALLY PURE AMINOHETEROARYL COMPOUNDS AS PROTEIN KINASE INHIBITORS

This application claims the benefit under 35 USC 119(e) of U.S. Provisional Application No. 60/605,086 filed on Aug. 26, 2004, the contents of which is hereby incorporated by reference in its entirety.

FIELD OF THE INVENTION

The invention relates generally to novel chemical compounds and methods. More particularly, the invention provides enantiomerically pure aminoheteroaryl compounds, particularly aminopyridines and aminopyrazines, having protein tyrosine kinase activity, and methods of synthesizing and using such compounds. Preferred compounds are c-Met inhibitors useful for the treatment of abnormal cell growth, such as cancers.

BACKGROUND

The hepatocyte growth factor (HGF) receptor (c-MET or HGFR) receptor tyrosine kinase (RTK) has been shown in many human cancers to be involved in oncogenesis, tumor progression with enhanced cell motility and invasion, as well as metastasis (see, e.g., Ma, P. C., Maulik, G., Christensen, J. & Salgia, R. (2003b). Cancer Metastasis Rev, 22, 309-25; Maulik, G., Shrikhande, A., Kijima, T., Ma, P. C., Morrison, P. T. & Salgia, R. (2002b). Cytokine Growth Factor Rev, 13, 41-59). c-MET (HGFR) can be activated through overexpression or mutations in various human cancers including small cell lung cancer (SCLC) (Ma, P. C., Kijima, T., Maulik, G., Fox, E. A., Sattler, M., Griffin, J. D., Johnson, B. E. & Salgia, R. (2003a). Cancer Res, 63, 6272-6281).

c-MET is a receptor tyrosine kinase that is encoded by the Met proto-oncogene and transduces the biological effects of hepatocyte growth factor (HGF), which is also referred to as scatter factor (SF). Jiang et al., Crit. Rev. Oncol. Hematol. 29: 209-248 (1999). c-MET and HGF are expressed in numerous tissues, although their expression is normally confined predominantly to cells of epithelial and mesenchymal origin, respectively. c-MET and HGF are required for normal mammalian development and have been shown to be important in cell migration, cell proliferation and survival, morphogenic differentiation, and organization of 3-dimensional tubular structures (e.g., renal tubular cells, gland formation, etc.). In addition to its effects on epithelial cells, HGF/SF has been reported to be an angiogenic factor, and c-MET signaling in endothelial cells can induce many of the cellular responses necessary for angiogenesis (proliferation, motility, invasion).

The c-MET receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-MET signaling is most commonly regulated by tumor-stroma (tumor-host) interactions. Furthermore, c-MET gene amplification, mutation, and rearrangement have been observed in a subset of human cancers. Families with germline mutations that activate c-MET kinase are prone to multiple kidney tumors as well as tumors in other tissues. Numerous studies have correlated the expression of c-MET and/or HGF/SF with the state of disease progression of different types of cancer (including lung, colon, breast, prostate, liver, pancreas, brain, kidney, ovaries, stomach, skin, and bone cancers). Furthermore, the overexpression of c-MET or HGF have been shown to correlate with poor prognosis and disease outcome in a number of major human cancers including lung, liver, gastric, and breast. c-MET has also been directly implicated in cancers without a successful treatment regimen such as pancreatic cancer, glioma, and hepatocellular carcinoma.

Examples of c-MET (HGFR) inhibitors, their synthesis and use, can be found in U.S. patent application Ser. No. 10/786,610, entitled "Aminoheteroaryl Compounds as Protein Kinase Inhibitors", filed Feb. 26, 2004, and corresponding international application PCT/US2004/005495 of the same title, filed Feb. 26, 2004, the disclosures of which are incorporated herein by reference in their entireties.

It would be desirable to have novel c-MET (HGFR) inhibitors and methods of using such inhibitors for the treatment of abnormal cell growth, such as cancer.

SUMMARY

In one embodiment, the invention provides an enantiomerically pure compound of formula 1

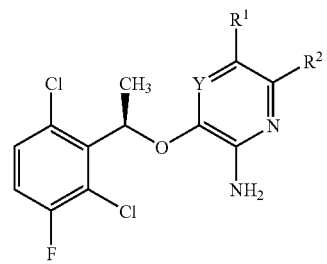

wherein:

Y is N or $CR^{12}$;

$R^1$ is selected from hydrogen, halogen, $C_{6-12}$ aryl, 5-12 membered heteroaryl, $C_{3-12}$ cycloalkyl, 3-12 membered heteroalicyclic, $-O(CR^6R^7)_nR^4$, $-C(O)R^4$, $-C(O)OR^4$, $-CN$, $-NO_2$, $-S(O)_mR^4$, $-SO_2NR^4R^5$, $-C(O)NR^4R^5$, $-NR^4C(O)R^5$, $-C(=NR^6)NR^4R^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, and each hydrogen in $R^2$ is optionally substituted by $R^8$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_mR^4$, $-SO_2NR^4R^5$, $-S(O)_2OR^4$, $-NO_2$, $-NR^4R^5$, $(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nOR^4$, $-(CR^6R^7)_nC(O)NR^4R^5$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$NH_2$, —CN, —OH, —O—$C_{1-12}$ alkyl, —O—$(CH_2)_n$ $C_{3-12}$ cycloalkyl, —O—$(CH_2)_n C_{6-12}$ aryl, —O—$(CH_2)_n$ (3-12 membered heteroalicyclic) or —O—$(CH_2)_n$(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —$S(O)_m R^4$, —$SO_2 NR^4 R^5$, —$S(O)_2 OR^4$, —$NO_2$, —$NR^4 R^5$, —$(CR^6 R^7)_n OR^4$, —CN, —$C(O)R^4$, —$OC(O)R^4$, —$NR^4 C(O)R^5$, —$(CR^6 R^7)_n C(O)OR^4$, —$(CR^6 R^7)_n NCR^4 R^5$, —$NR^4 C(O)NR^5 R^6$, —$NR^4 S(O)_p R^5$, or —$C(O)NR^4 R^5$; $R^9$ or $R^{10}$ may combine with a ring atom of A or a substituent of A to form a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—$(CH_2)_n C_{3-12}$ cycloalkyl, —O—$(CH_2)_n$ $C_{6-12}$ aryl, —O—$(CH_2)_n$(3-12 membered heteroalicyclic), —O—$(CH_2)_n$(5-12 membered heteroaryl) or —CN, and each hydrogen in $R^{11}$ is optionally substituted by halogen, —OH, —CN, —$C_{1-12}$ alkyl which may be partially or fully halogenated, —O—$C_{1-12}$ alkyl which may be partially or fully halogenated, —CO, —SO or —$SO_2$;

$R^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_m R^4$, —$SO_2 NR^4 R^5$, —$S(O)_2 OR^4$, —$NO_2$, —$NR^4 R^5$, —$(CR^6 R^7)_n OR^4$, —CN, —$C(O)R^4$, —$OC(O)R^4$, —$O(CR^6 R^7)_n R^4$, —$NR^4 C(O)R^5$, —$(CR^6 R^7)_n C(O)OR^4$, —$(CR^6 R^7)_n NCR^4 R^5$, —$C(=NR^6)NR^4 R^5$, —$NR^4 C(O)NR^5 R^6$, —$NR^4 S(O)_p R^5$ or —$C(O)NR^4 R^5$, and each hydrogen in $R^{12}$ is optionally substituted by $R^3$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_m R^4$, —$SO_2 NR^4 R^5$, —$S(O)_2 OR^4$, —$NO_2$, —$NR^4 R^5$, —$(CR^6 R^7)_n OR^4$, —CN, —$C(O)R^4$, —$OC(O)R^4$, —$O(CR^6 R^7)_n R^4$, —$NR^4 C(O)R^5$, —$(CR^6 R^7)_n C(O)OR^4$, —$(CR^6 R^7)_n C(O)NR^4 R^5$, —$(CR^6 R^7)_n NCR^4 R^5$, —$C(=NR^6)NR^4 R^5$, —$NR^4 C(O)NR^5 R^6$, —$NR^4 S(O)_p R^5$, —$C(O)NR^4 R^5$, —$(CR^6 R^7)_n$ (3-12 membered heteroalicyclic), —$(CR^6 R^7)_n (C_{3-12}$ cycloalkyl), —$(CR^6 R^7)(C_{6-12}$ aryl), —$(CR^6 R^7)_n$(5-12 membered heteroaryl), —$(CR^6 R^7)_n C(O)NR^4 R^5$, or —$(CR^6 R^7)C(O)R^4$, $R^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

each m is independently 0, 1 or 2;

each n is independently 0, 1, 2, 3 or 4;

each p is independently 1 or 2;

or a pharmaceutically acceptable salt, hydrate or solvate thereof.

In a particular aspect of this embodiment, $R^2$ is hydrogen.

In another particular aspect of this embodiment, Y is N.

In another particular aspect of this embodiment, Y is N and $R^2$ is hydrogen.

In another particular aspect of this embodiment, Y is $CR^{12}$.

In another particular aspect of this embodiment, Y is $CR^{12}$ and $R^{12}$ is H.

In another particular aspect of this embodiment, and in combination with any other particular aspect not inconsistent, $R^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane or phenyl group, and each hydrogen in $R^1$ is optionally substituted by one or more $R^3$ groups.

In another particular aspect of this embodiment, and in combination with any other particular aspect not inconsistent, $R^1$ is a fused ring heteroaryl group, and each hydrogen in $R^1$ is optionally substituted by one or more $R^3$ groups.

In another particular aspect of this embodiment, and in combination with any other particular aspect not inconsistent, $R^1$ is hydrogen.

In another particular aspect of this embodiment, and in combination with any other particular aspect not inconsistent, $R^1$ is a halogen.

In another embodiment, the invention provides an enantiomerically pure compound of formula 1a

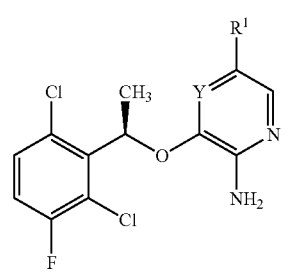

1a wherein:

Y is N or CH;

$R^1$ is a furan, thiopene, pyrrole, pyrroline, pyrrolidine, dioxolane, oxazole, thiazole, imidazole, imidazoline, imidazolidine, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane, azitidine or phenyl group; and each hydrogen in $R^1$ is optionally substituted by $R^3$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$ or —C(O)NR$^4$R$^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —NH$_2$, —CN, —OH, —O—$C_{1-12}$ alkyl, —O—(CH$_2$)$_n$ $C_{3-12}$ cycloalkyl, —O—(CH$_2$)$_n$C$_{6-12}$ aryl, —O—(CH$_2$)$_n$ (3-12 membered heteroalicyclic) or —O—(CH$_2$)$_n$(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —(CR$^6$R$^7$)$_n$NCR$^4$R$^5$, —NR$^4$C(O)NR$^5$R$^6$, —NR$^4$S(O)$_p$R$^5$ or —C(O)NR$^4$R$^5$; $R^9$ or $R^{10}$ may combine with a ring atom of A or a substituent of A to form a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—(CH$_2$)$_n$C$_{3-12}$ cycloalkyl, —O—(CH$_2$)$_n$ C$_{6-12}$ aryl, —O—(CH$_2$)$_n$(3-12 membered heteroalicyclic), —O—(CH$_2$)$_n$(5-12 membered heteroaryl) or —CN, and each hydrogen in $R^{11}$ is optionally substituted by halogen, —OH, —CN, —C$_{1-12}$ alkyl which may be partially or fully halogenated, —O—C$_{1-2}$ alkyl which may be partially or fully halogenated, —CO, —SO or —SO$_2$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_p$R$^5$, —C(O)NR$^4$R$^5$, —(CR$^6$R$^7$)$_n$(3-12 membered heteroalicyclic), —(CR$^6$R$^7$)(C$_{3-12}$ cycloalkyl), —(CR$^6$R$^7$)$_n$(C$_{6-12}$ aryl), —(CR$^6$R$^7$)$_n$(5-12 membered heteroaryl), —(CR$^6$R$^7$)$_n$C(O)NR$^4$R$^5$, or —(CR$^6$R$^7$)$_n$C(O)R$^4$, R$^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

each m is independently 0, 1 or 2;

each n is independently 0, 1, 2, 3 or 4;

each p is independently 1 or 2;

or a pharmaceutically acceptable salt, hydrate or solvate thereof.

In another embodiment, the invention provides an enantiomerically pure compound selected from the group consisting of 5-Bromo-3-[(R)-1-(2,6-dichloro-3-fluoro-phenyl)-ethoxy]-pyrazin-2-ylamine; 5-iodo-3-[(R)-1-(2,6-dichloro-3-fluoro-phenyl)-ethoxy]-pyridin-2-ylamine; 5-bromo-3-[1 (R)-(2,6-dichloro-3-fluoro-phenyl)-ethoxy]-pyridin-2-ylamine; 4-{5-Amino-6-[(R)-1-(2,6-dichloro-3-fluoro-phenyl)-ethoxy]-pyrazin-2-yl}-benzoic acid; (4-{5-Amino-6-[(R)-1-(2,6-dichloro-3-fluoro-phenyl)-ethoxy]-pyrazin-2-yl}-phenyl)-piperazin-1-yl-methanone; 4-(4-{5-Amino-6-[(R)-1-(2,6-dichloro-3-fluoro-phenyl)-ethoxy]-pyrazin-2-yl}-benzoyl)-piperazine-1-carboxylic acid tert-butyl ester; 3-[(1R)-1-(2,6-dichloro-3-fluorophenyl)ethoxy]-5-[4-(piperazin-1-ylcarbonyl)phenyl]pyridin-2-amine; 4-{6-amino-5-[(1R)-1-(2,6-dichloro-3-fluorophenyl)ethoxy]pyridin-3-yl}-N-[2-(dimethylamino)ethyl]-N-methylbenzamide; (4-{6-amino-5-[(1R)-1-(2,6-dichloro-3-fluorophenyl)ethoxy]pyridin-3-yl}phenyl)methanol; 4-{6-amino-5-[(1R)-1-(2,6-dichloro-3-fluorophenyl)ethoxy]pyridin-3-yl}-N-[3-(dimethylamino)propyl]-N-methylbenzamide; tert-butyl 4-(4-{6-amino-5-[(1R)-1-(2,6-dichloro-3-fluorophenyl)ethoxy]pyridin-3-yl}benzoyl)piperazine-1-carboxylate; 3-[(R)-1-(2,6-Dichloro-3-fluoro-phenyl)-ethoxy]-5-[1-(1-methyl-piperidin-4-yl)-1H-pyrazol-4-yl]-pyridin-2-ylamine; 1-[4-(4-{6-Amino-5-[(R)-1-(2,6-dichloro-3-fluoro-phenyl)-ethoxy]-pyridin-3-yl}-pyrazol-1-yl)-piperidin-1-yl]-2-hydroxy-ethanone; 3-[(R)-1-(2,6-Dichloro-3-fluoro-phenyl)-ethoxy]-5-(1-piperidin-4-yl-1H-pyrazol-4-yl)-pyridin-2-ylamine; 3-[(R)-1-(2,6-Dichloro-3-fluoro-phenyl)-ethoxy]-5-(1-piperidin-4-yl-1H-pyrazol-4-yl)-pyridin-2-ylamine; 3-[(R)-1-(2,6-Dichloro-3-fluoro-phenyl)-ethoxy]-5-(1-piperidin-4-yl-1H-pyrazol-4-yl)-pyrazin-2-ylamine; 3-[(R)-1-(2,6-Dichloro-3-fluoro-phenyl)-ethoxy]-5-(1H-pyrazol-4-yl)-pyrazin-2-ylamine; 1-[4-(4-{5-Amino-6-[(R)-1-(2,6-dichloro-3-fluoro-phenyl)-ethoxy]-pyrazin-2-yl)pyrazol-1-yl}-piperidin-1-yl]-2-hydroxy-ethanone; 3-[(R)-1-(2,6-Dichloro-3-fluoro-phenyl)-ethoxy]-5-[1-(1-methyl-piperidin-4-yl)-1H-pyrazol-4-yl]-pyrazin-2-ylamine; 1-[4-(4-{5-Amino-6-[(R)-1-(2,6-dichloro-3-fluoro-phenyl)-ethoxy]-pyrazin-2-yl}-pyrazol-1-yl-piperidin-1-yl]-2-dimethylamino-ethanone; 3-[(R)-1-(2-Chloro-3,6-difluoro-phenyl)-ethoxy]-5-(1-piperidin-4-yl-1H-pyrazol-4-yl)-pyridin-2-ylamine; or a pharmaceutically acceptable salt, solvate or hydrate thereof.

In another embodiment, the invention provides a pharmaceutical composition comprising any of the compounds of the invention and a pharmaceutically acceptable carrier. Examples of such compositions are described below.

Preferred compounds of the invention include those having c-MET inhibitory activity as defined by any one or more of IC$_{50}$, Ki, or percent inhibition (% I). One skilled in the art can readily determine if a compound has such activity by carrying out the appropriate assay, and descriptions of such assays are shown in the Examples section herein. In one embodiment, particularly preferred compounds have a c-MET Ki of less than 5 µM or less than 2 µM, or less than 1 µM, or less than 500 nM or less than 200 nM or less than 100 nM. In another embodiment, particularly preferred compounds have a c-MET inhibition at 1 µM of at least 10% or at least 20% or at least 30% or at least 40% or at least 50% or at least 60% or at least 70% or at least 80% or at least 90%. Methods for measuring c-MET/HGFR activity are described in the Examples herein.

In another embodiment, the invention provides a method of treating abnormal cell growth in a mammal, including a human, the method comprising administering to the mammal any of the pharmaceutical compositions of the invention.

In a specific embodiment of any of the inventive methods described herein, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

In another embodiment, the invention provides a method of treating an HGFR mediated disorder in a mammal, including a human, the method comprising administering to the mammal any of the pharmaceutical compositions of the invention.

In further specific embodiments of any of the inventive methods described herein, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diazi-quone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)methyl]amino]benzoyl]-L-aspartic acid, N-[4-[[(2,4-diamino-5-ethyl-6-quinazolinyl)methyl]amino]benzoyl]-L-aspartic acid, N-[2-chloro-4-[[(2,4-diaminopteridinyl)methyl] amino]benzoyl]-L-aspartic acid, soluble Bakers antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747, 498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383, 755 (filed Aug. 26, 1999); and the compounds disclosed and claimed in the following U.S. provisional patent applications 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

DEFINITIONS

Unless otherwise stated, the following terms used in the specification and claims have the meanings discussed below. Variables defined in this section, such as R, X, n and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

"Alkyl" refers to a saturated aliphatic hydrocarbon radical including straight chain and branched chain groups of 1 to 20 carbon atoms, preferably 1 to 12 carbon atoms, more preferably 1 to 8 carbon atoms, or 1 to 6 carbon atoms, or 1 to 4 carbon atoms. "Lower alkyl" refers specifically to an alkyl group with 1 to 4 carbon atoms. Examples of alkyl groups include methyl, ethyl, propyl, 2-propyl, n-butyl, iso-butyl, tert-butyl, pentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring.

"Cycloalkyl" refers to a 3 to 8 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^x$R$^y$, with R$^x$ and R$^y$ as defined above. Illustrative examples of cycloalkyl are derived from, but not limited to, the following:

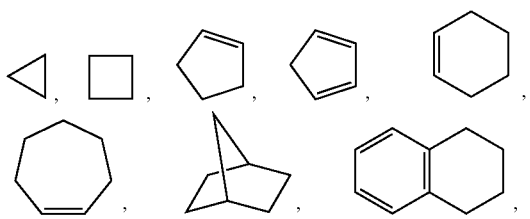

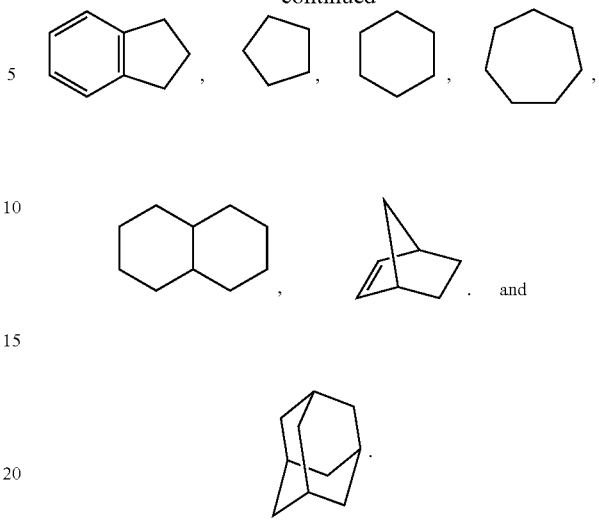

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

"Aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —NR$^x$R$^y$, with R$^x$ and R$^y$ as defined above.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^x$R$^y$ with R$^x$ and R$^y$ as defined above.

A pharmaceutically acceptable heteroaryl is one that is sufficiently stable to be attached to a compound of the invention, formulated into a pharmaceutical composition and subsequently administered to a patient in need thereof.

Examples of typical monocyclic heteroaryl groups include, but are not limited to:

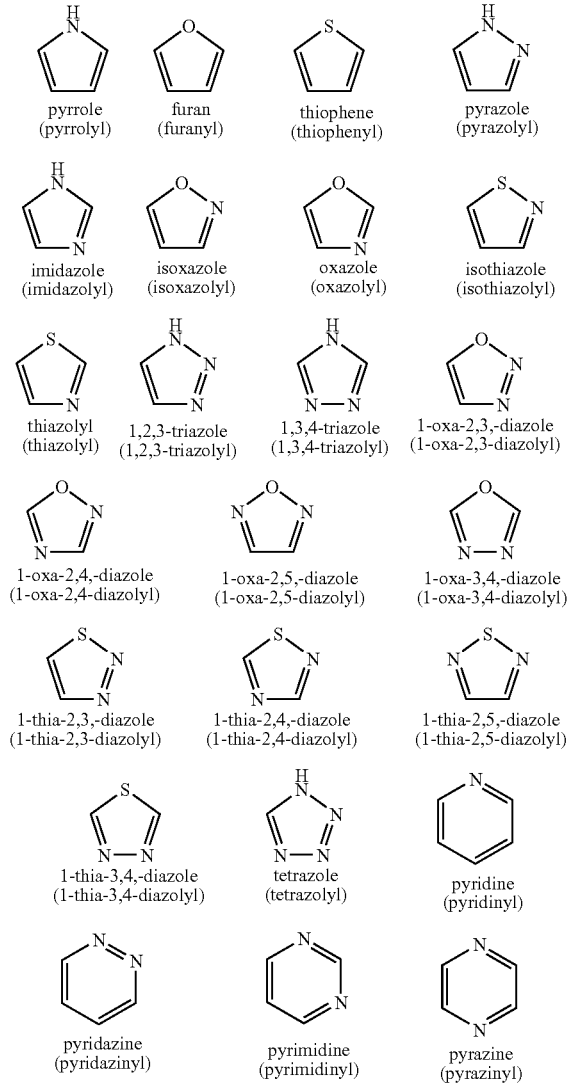

Examples of suitable fused ring heteroaryl groups include, but are not limited to:

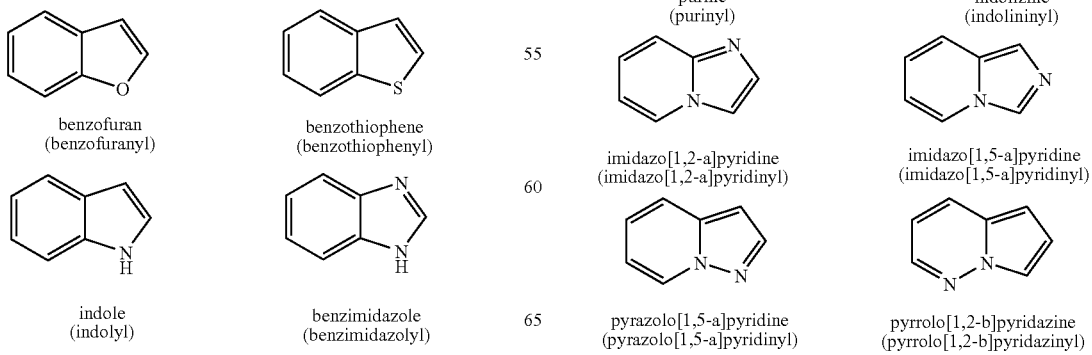

indazole (indazolyl)     benzotriazole (benzotriazolyl)

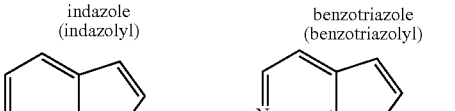

pyrrolo[2,3-b]pyridine (pyrrolo[2,3-b]pyridinyl)     pyrrolo[2,3-c]pyridine (pyrrolo[2,3-c]pyridinyl)

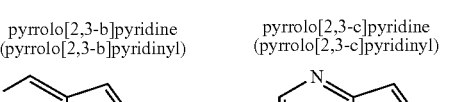

pyrrolo[3,2-c]pyridine (pyrrolo[3,2-c]pyridinyl)     pyrrolo[3,2-b]pyridine (pyrrolo[3,2-b]pyridinyl)

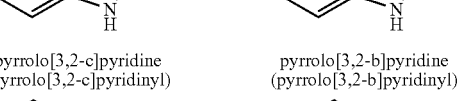

imidazo[4,5-b]pyridine (imidazo[4,5-b]pyridinyl)     imidazo[4,5-c]pyridine (imidazo[4,5-c]pyridinyl)

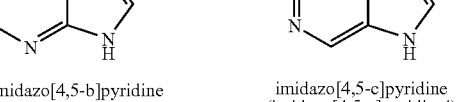

pyrazolo[4,2-d]pyridine (pyrazolo[4,3-d]pyridinyl)     pyrazolo[4,3-c]pyridine (pyrazolo[4,3-c]pyridinyl)

pyrazolo[3,4-d]pyridine (pyrazolo[3,4-d]pyridinyl)     pyrazolo[3,4-b]pyridine (pyrazolo[3,4-b]pyridinyl)

isoindole (isoindolyl)     indazole (indazolyl)

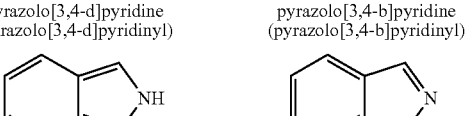

purine (purinyl)     indolizine (indolininyl)

imidazo[1,2-a]pyridine (imidazo[1,2-a]pyridinyl)     imidazo[1,5-a]pyridine (imidazo[1,5-a]pyridinyl)

pyrazolo[1,5-a]pyridine (pyrazolo[1,5-a]pyridinyl)     pyrrolo[1,2-b]pyridazine (pyrrolo[1,2-b]pyridazinyl)

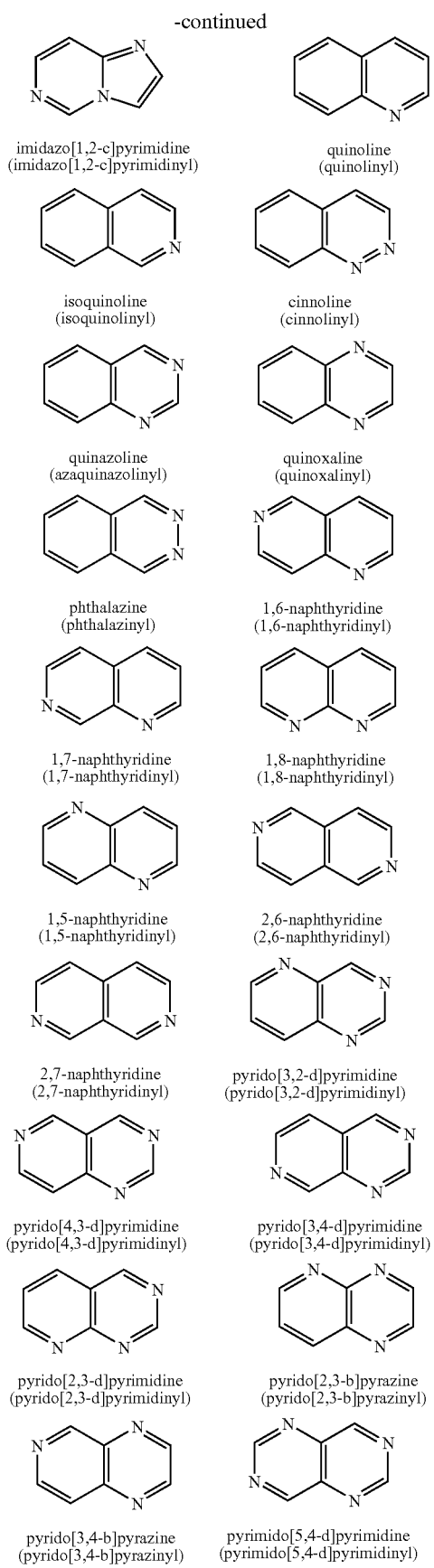
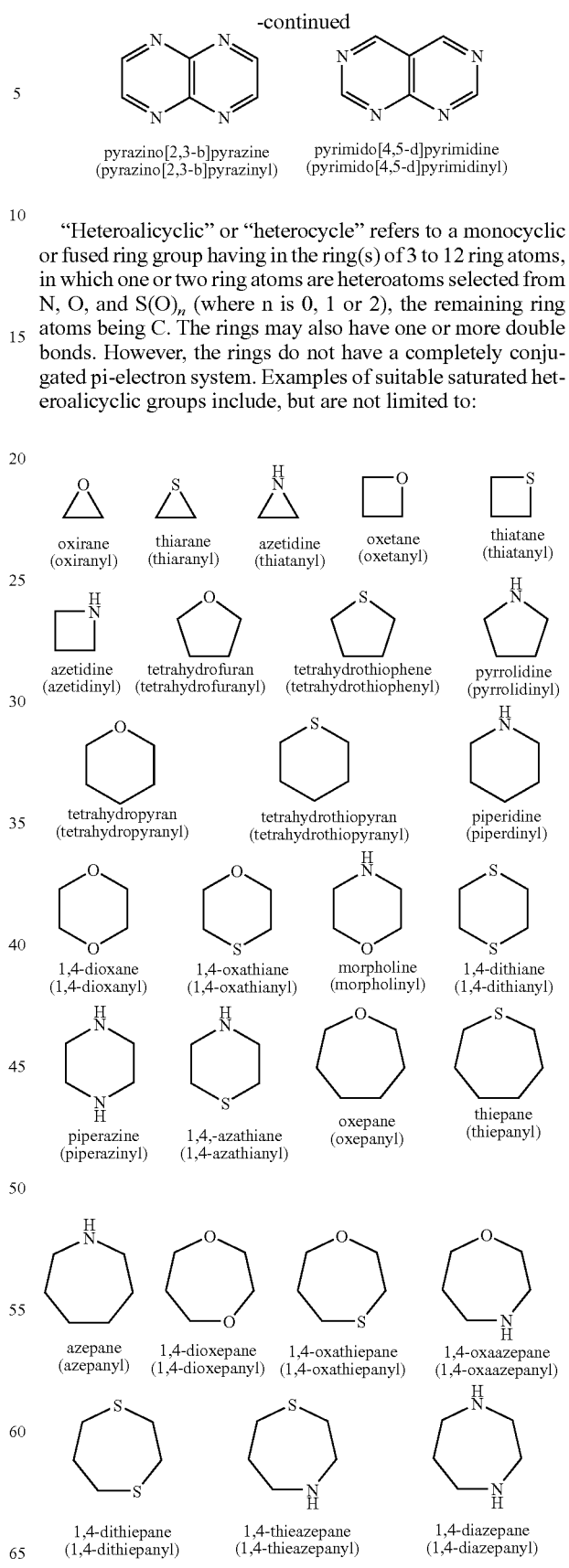

"Heteroalicyclic" or "heterocycle" refers to a monocyclic or fused ring group having in the ring(s) of 3 to 12 ring atoms, in which one or two ring atoms are heteroatoms selected from N, O, and $S(O)_n$ (where n is 0, 1 or 2), the remaining ring atoms being C. The rings may also have one or more double bonds. However, the rings do not have a completely conjugated pi-electron system. Examples of suitable saturated heteroalicyclic groups include, but are not limited to:

Examples of suitable partially unsaturated heteroalicyclic groups include, but are not limited to:

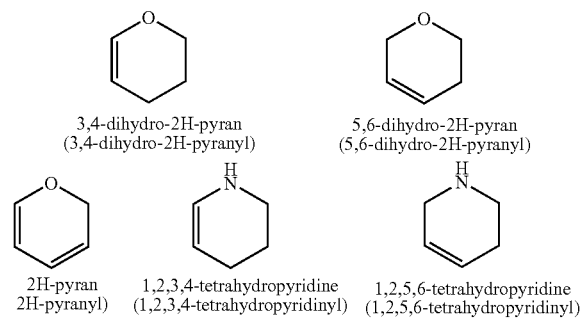

3,4-dihydro-2H-pyran (3,4-dihydro-2H-pyranyl)

5,6-dihydro-2H-pyran (5,6-dihydro-2H-pyranyl)

2H-pyran 2H-pyranyl)

1,2,3,4-tetrahydropyridine (1,2,3,4-tetrahydropyridinyl)

1,2,5,6-tetrahydropyridine (1,2,5,6-tetrahydropyridinyl)

The heterocycle group is optionally substituted with one or two substituents independently selected from halo, lower alkyl, lower alkyl substituted with carboxy, ester hydroxy, or mono or dialkylamino.

"Hydroxy" refers to an —OH group.

"Alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

"Haloalkoxy" refers to an —O-(haloalkyl) group. Representative examples include, but are not limited to, trifluoromethoxy, tribromomethoxy, and the like.

"Aryloxy" refers to an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Mercapto" refers to an —SH group.

"Alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

"Arylthio" refers to an —S-aryl or an —S-heteroaryl group, as defined herein. Representative examples include, but are not limited to, phenylthio, pyridinylthio, furanylthio, thienylthio, pyrimidinylthio, and the like and derivatives thereof.

"Acyl" or "carbonyl" refers to a —C(O)R" group, where R" is selected from the group consisting of hydrogen, lower alkyl, trihalomethyl, unsubstituted cycloalkyl, aryl optionally substituted with one or more, preferably one, two, or three substituents selected from the group consisting of lower alkyl, trihalomethyl, lower alkoxy, halo and —NR$^x$R$^y$ groups, heteroaryl (bonded through a ring carbon) optionally substituted with one or more, preferably one, two, or three substitutents selected from the group consisting of lower alkyl, trihaloalkyl, lower alkoxy, halo and —NR$^x$R$^y$ groups and heteroalicyclic (bonded through a ring carbon) optionally substituted with one or more, preferably one, two, or three substituents selected from the group consisting of lower alkyl, trihaloalkyl, lower alkoxy, halo and —NR$^x$R$^y$ groups. Representative acyl groups include, but are not limited to, acetyl, trifluoroacetyl, benzoyl, and the like "Aldehyde" refers to an acyl group in which R" is hydrogen.

"Thioacyl" or "thiocarbonyl" refers to a —C(S)R" group, with R" as defined above.

A "thiocarbonyl" group refers to a —C(S)R" group, with R" as defined above.

A "C-carboxy" group refers to a —C(O)OR" group, with R" as defined above.

An "O-carboxy" group refers to a —OC(O)R" group, with R" as defined above.

"Ester" refers to a —C(O)OR" group with R" as defined herein except that R" cannot be hydrogen.

"Acetyl" group refers to a —C(O)CH$_3$ group.

"Halo" group refers to fluorine, chlorine, bromine or iodine, preferably fluorine or chlorine.

"Trihalomethyl" group refers to a methyl group having three halo substituents, such as a trifluoromethyl group.

"Cyano" refers to a —C≡N group.

A "sulfinyl" group refers to a —S(O)R" group wherein, in addition to being as defined above, R" may also be a hydroxy group.

A "sulfonyl" group refers to a —S(O)$_2$R" group wherein, in addition to being as defined above, R" may also be a hydroxy group.

"S-sulfonamido" refers to a —S(O)$_2$NR$^x$R$^y$ group, with R$^x$ and R$^y$ as defined above.

"N-sulfonamido" refers to a —NR$^x$S(O)$_2$R$^y$ group, with R$^x$ and R$^y$ as defined above.

"O-carbamyl" group refers to a —OC(O)NR$^x$R$^y$ group with R$^x$ and R$^y$ as defined above.

"N-carbamyl" refers to an R$^y$OC(O)NR$^x$— group, with R$^x$ and R$^y$ as defined above.

"O-thiocarbamyl" refers to a —OC(S)NR$^x$R$^y$ group with R$^x$ and R$^y$ as defined above.

"N-thiocarbamyl" refers to a R$^y$OC(S)NR$^x$ group, with R$^y$ and R$^x$ as defined above.

"Amino" refers to an —NR$^x$R$^y$ group, wherein R$^x$ and R$^y$ are both hydrogen.

"C-amido" refers to a —C(O)NR$^x$R$^y$ group with R$^x$ and R$^y$ as defined above.

"N-amido" refers to a R$^x$C(O)NR$^y$— group, with R$^x$ and R$^y$ as defined above.

"Nitro" refers to a —NO$_2$ group.

"Haloalkyl" means an alkyl, preferably lower alkyl, that is substituted with one or more same or different halo atoms, e.g., —CH$_2$Cl, —CF$_3$, —CH$_2$CF$_3$, —CH$_2$CCl$_3$, and the like.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

"Aralkyl" means alkyl, preferably lower alkyl, that is substituted with an aryl group as defined above; e.g., —CH$_2$phenyl, —(CH$_2$)$_2$phenyl, —(CH$_2$)$_3$phenyl, CH$_3$CH (CH$_3$)CH$_2$phenyl, and the like and derivatives thereof.

"Heteroaralkyl" group means alkyl, preferably lower alkyl, that is substituted with a heteroaryl group; e.g., —CH$_2$pyridinyl, —(CH$_2$)$_2$pyrimidinyl, —(CH$_2$)$_3$imidazolyl, and the like, and derivatives thereof.

"Monoalkylamino" means a radical —NHR where R is an alkyl or unsubstituted cycloalkyl group; e.g., methylamino, (1-methylethyl)amino, cyclohexylamino, and the like.

"Dialkylamino" means a radical —NRR where each R is independently an alkyl or unsubstituted cycloalkyl group; dimethylamino, diethylamino, (1-methylethyl)-ethylamino, cyclohexylmethylamino, cyclopentylmethylamino, and the like.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. The effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

As used herein, the terms "optically pure," "enantiomerically pure," "pure enantiomer," and "optically pure enantiomer" mean a composition that comprises one enantiomer of a compound and is substantially free of the opposite enantiomer of the compound. A typical optically pure compound comprises greater than about 80% by weight of one enantiomer of the compound and less than about 20% by weight of the opposite enantiomer of the compound, more preferably greater than about 90% by weight of one enantiomer of the compound and less than about 10% by weight of the opposite enantiomer of the compound, even more preferably greater than about 95% by weight of one enantiomer of the compound and less than about 5% by weight of the opposite enantiomer of the compound, and most preferably greater than about 97% by weight of one enantiomer of the compound and less than about 3% by weight of the opposite enantiomer of the compound.

DETAILED DESCRIPTION

General schemes for synthesizing the compounds of the invention can be found in the Examples section herein.

Some of the general procedures are shown with reference to synthesis of compounds wherein the 1-(2,6-dichloro-3-fluorophenyl)-ethoxy moiety is the pure (R)-isomer, and some are shown with reference to compounds wherein said moiety is a racemic mixture. It should be understood that the procedures herein can be used to produce racemic compounds or enantiomerically pure (R) isomers by choosing the corresponding racemic or enantiomerically pure starting material.

The procedures shown herein can be used to produce a wide variety of enantiomerically pure compounds by selection of the appropriate enantiomerically pure starting material. In addition to the compounds shown herein, the invention also provides enantiomerically pure compounds corresponding to the 3-[1-(2,6-dichloro-3-fluoro-phenyl)-ethoxy]-pyridin-2-ylamine and 3-[1-(2,6-dichloro-3-fluoro-phenyl)-ethoxy]-pyrazin-2-ylamine compounds shown in U.S. patent application Ser. No. 10/786,610 (PCT/US2004/005495); in U.S. application Ser. No. 60/605,244, filed Aug. 26, 2004 and entitled, "Pyrazolo-Substituted Aminoheteroaryl Compounds as Protein Kinase Inhibitors"; and in U.S. application Ser. No. 60/605,279, filed Aug. 26, 2004 and entitled, "Aminoheteroaryl Compounds as Protein Kinase Inhibitors". The disclosures of these documents are incorporated herein by reference in their entireties.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In the following examples, "Et" means ethyl, "Ac" means acetyl, "Me" means methyl, "Ms" means methanesulfonyl ($CH_3SO_2$), "iPr" means isopropyl, "HATU" means 2-(7-Aza-1H-benzotriazole-1-yl)-1,1,3,3-tetramethyluronium hexafluorophosphate, "Ph" means phenyl, "Boc" means tert-butoxycarbonyl, "EtOAc" means ethyl acetate, "HOAc" means acetic acid, "NEt$_3$" or "Et$_3$N" means triethylamine, "THF" means tetrahydrofuran, "DIC" means diisopropylcarbodiimide, "HOBt" means hydroxy benzotriazole, "MeOH" means methanol, "i-PrOAc" means isopropyl acetate, "KOAc" means potassium acetate, "DMSO" means dimethylsulfoxide, "AcCl" means acetyl chloride, "CDCl$_3$" means deuterated chloroform, "MTBE" means methyl t-butyl ether, "DMF" means dimethyl formamide, "Ac$_2$O" means acetic anhydride, "Me3SOI" means trimethylsulfoxonium iodide, "DMAP" means 4-dimethylaminopyridine, "dppf" means diphenylphosphino ferrocene, "DME" means ethylene glycol dimethyl ether, HOBT means 1-hydroxybenzotriazole, EDC means 1-Ethyl-3-(3-dimethylaminopropyl)-carbodiimide.

The following examples are given to illustrate the present invention. It should be understood, however, that the invention is not to be limited to the specific conditions or details described in these examples.

Reagents can be synthesized as shown herein, or are available from commercial sources (e.g., Aldrich, Milwaukee, Wis.; Acros, Morris Plains, N.J.; Biosynth International, Naperville, Ill.; Frontier Scientific, Logan, Utah; TCI America, Portland, Oreg.; Combi-Blocks, San Diego, Calif.; Matrix Scientific, Columbia, S.C.; Acros, Morris Plains, N.J.; Alfa Aesar, Ward Hill, Mass.; Apollo Scientific, UK; etc.) or can be synthesized by procedures known in the art.

The synthesis of several specific reagents is shown in U.S. patent application Ser. No. 10/786,610, entitled "Aminoheteroaryl Compounds as Protein Kinase Inhibitors", filed Feb. 26, 2004, and corresponding international application PCT/US2004/005495 of the same title, filed Feb. 26, 2004. Other reagents can be synthesized by adapting the procedures therein, and one skilled in the art can readily adapt those procedures to produce the desired compounds. Further, these references contain general procedures and specific examples for the preparation of a large number of heteroarylamino compounds, and one skilled in the art can readily adapt such procedures and examples to the preparation of compounds of the present invention. The disclosures of these references are incorporated herein by reference in their entireties.

When a general or exemplary synthetic procedure is referred to, one skilled in the art can readily determine the appropriate reagents, if not indicated, extrapolating from the general or exemplary procedures. Some of the general procedures are given as examples for preparing specific compounds. One skilled in the art can readily adapt such procedures to the synthesis of other compounds. It should be understood that R groups shown in the general procedures are meant to be generic and non-limiting, and do not correspond to definitions of R groups elsewhere in this document. Each such R group represents one or multiple chemical moieties that can be the same or different from other chemical moieties also represented by the same R symbol. One skilled in the art can readily appreciate the range of R groups suitable in the exemplary syntheses. Moreover, representation of an unsubstituted position in structures shown or referred to in the general procedures is for convenience and does not preclude substitution as described elsewhere herein. For specific groups that can be present, either as R groups in the general procedures or as optional substituents not shown, refer to the descriptions in the remainder of this document, including the claims, summary and detailed description.

Some of the general procedures are shown with reference to synthesis of compounds wherein the 1-(2,6-dichloro-3-fluorophenyl)-ethoxy moiety is the pure (R)-isomer, and some are shown with reference to compounds wherein said moiety is a racemic mixture. It should be understood that the procedures herein can be used to produce racemic compounds or enantiomerically pure (R) isomers by choosing the corresponding racemic or enantiomerically pure starting material.

The procedures shown herein can be used to produce a wide variety of enantiomerically pure compounds by selection of the appropriate enantiomerically pure starting material. In addition to the compounds shown herein, the invention also provides enantiomerically pure compounds corresponding to the 3-[1-(2,6-dichloro-3-fluoro-phenyl)-ethoxy]-pyridin-2-ylamine and 3-[1-(2,6-dichloro-3-fluoro-phenyl)-ethoxy]-pyrazin-2-ylamine compounds shown in U.S. patent application Ser. No. 10/786,610 (PCT/US2004/005495); in U.S. application Ser. No. 60/605,244, filed Aug. 26, 2004 and entitled, "Pyrazolo-Substituted Aminoheteroaryl Compounds as Protein Kinase Inhibitors"; and in U.S. application Ser. No. 60/605,279, filed Aug. 26, 2004 and entitled, "Aminoheteroaryl Compounds as Protein Kinase Inhibitors". The disclosures of these documents are incorporated herein by reference in their entireties.

Select Starting Materials 5-bromo-3-[1-(2,6-dichloro-3-fluoro-phenyl)-ethoxy]-pyridin-2-ylamine (racemate)

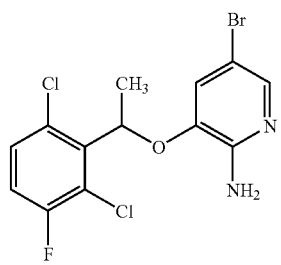

1. 2,6-Dichloro-3-fluoroacetophenone (15 g, 0.072 mol) was stirred in THF (150 mL, 0.5M) at 0° C. using an ice bath for 10 min. Lithium aluminum hydride (2.75 g, 0.072 mol) was slowly added. The reaction was stirred at ambient temperature for 3 hr. The reaction was cooled in ice bath, and water (3 mL) was added drop wisely followed by adding 15% NaOH (3 mL) slowly. The mixture was stirred at ambient temperature for 30 min. 15% NaOH (9 mL), MgSO₄ were added and the mixture filtered to remove solids. The solids were washed with THF (50 mL) and the filtrate was concentrated to give 1-(2,6-dichloro-3-fluoro-phenyl)-ethanol (14.8 gm, 95% yield) as a yellow oil. ¹H NMR (400 MHz, DMSO-d₆) δ 1.45 (d, 3H), 5.42 (m, 2H), 7.32 (m, 1H), 7.42 (m, 1H).

2. To a stirred solution of triphenyl phosphine (8.2 g, 0.03 mol) and DEAD (13.65 mL of a 40% solution in toluene) in THF (200 mL) at 0° C. was added a solution of 1-(2,6-dichloro-3-fluoro-phenyl)-ethanol (4.55 g, 0.021 mol) and 3-hydroxy-nitropyridine (3.35 g, 0.023 mol) in THF (200 mL). The resulting bright orange solution was stirred under a nitrogen atmosphere at ambient temperature for 4 hours at which point all starting materials had been consumed. The solvent was removed, and the crude material was dry loaded onto silica gel, and eluted with ethyl acetate-hexanes (20:80) to yield 3-(2,6-dichloro-3-fluoro-benzyloxy)-2-nitro-pyridine (6.21 g, 0.021 mol, 98%) as a pink solid. ¹H NMR (CDCl₃, 300 MHz) δ1.8-1.85 (d, 3H), 6.0-6.15 (q, 1H), 7.0-7.1 (t, 1H), 7.2-7.21 (d, 1H), 7.25-7.5 (m, 2H), 8.0-8.05 (d, 1H).

3. To a stirred mixture of AcOH (650 mL) and EtOH (500 mL) was suspended 3-(2,6-dichloro-3-fluoro-benzyloxy)-2-nitro-pyridine (9.43 g, 0.028 mol) and iron chips (15.7 g, 0.28 mol). The reaction was heated slowly to reflux and allowed to stir for 1 hr. The reaction was cooled to room temperature then diethyl ether (500 mL) and water (500 mL) was added. The solution was carefully neutralized by the addition of sodium carbonate. The combined organic extracts were washed with sat'd NaHCO₃ (2×100 mL), H₂O (2×100 mL) and brine (1×100 mL) then dried (Na₂SO₄), filtered and concentrated to dryness under vacuum to yield 3-(2,6-dichloro-3-fluoro-benzyloxy)-pyridin-2-ylamine (9.04 g, 0.027 mol, 99%) as a light pink solid. ¹H NMR (CDCl₃, 300 MHz) δ1.8-1.85 (d, 3H), 4.9-5.2 (brs, 2H), 6.7-6.84 (q, 1H), 7.0-7.1 (m, 1H), 7.2-7.3 (m, 1H), 7.6-7.7 (m, 1H).

4. A stirring solution of 3-(2,6-dichloro-3-fluoro-benzyloxy)-pyridin-2-ylamine (9.07 g, 0.03 mol) in acetonitrile was cooled to 0° C. using an ice bath. To this solution was added N-bromosuccinimide (NBS) (5.33 g, 0.03 mol) portionwise. The reaction was stirred at 0° C. for 15 min. The reaction was concentrated to dryness under vacuum. The resulting dark oil was dissolved in EtOAc (500 mL), and purified via silica gel chromatography. The solvents were then removed in vacuo to yield 5-bromo-3-(2,6-dichloro-3-fluoro-benzyloxy)-pyridin-2-ylamine (5.8 g, 0.015 mol, 51%) as a white crystalline solid. ¹H NMR (CDCl₃, 300 MHz) δ1.85-1.95 (d, 3H), 4.7-5.0 (brs, 2H), 5.9-6.01 (q, 1H), 6.8-6.95 (d, 1H), 7.01-7.2 (t, 1H), 7.4-7.45 (m, 1H), 7.8-7.85 (d, 1H).

5-iodo-3-[1-(2,6-dichloro-3-fluoro-phenyl)-ethoxy]-pyridin-2-ylamine (racemate)

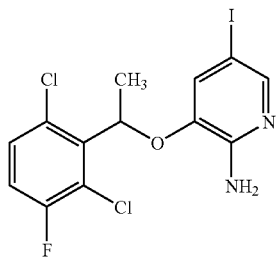

To a solution of 3-[1-(2,6-Dichloro-3-fluoro-phenyl)-ethoxy]-pyridin-2-ylamine (10.0 g, 33.2 mmol) in acetonitrile (600 mL) and acetic acid (120 mL) was added N-iodosuccinimide (11.2 g, 49.8 mmol). The mixture was stirred at room temperature for 4 h and the reaction was quenched with Na₂S₂O₅ solution. After evaporation, the residue was partitioned between ethyl acetate and water. The organic layer was washed with 2N NaOH solution, brine, and dried over Na₂SO₄. The crude product was purified on a silica gel column to provide 5-iodo-3-[1-(2,6-dichloro-3-fluoro-phenyl)-ethoxy]-pyridin-2-ylamine (7.1 g, 50% yield). MS m/z 427 [M+1]. ¹H NMR (400 MHz, DMSO-D6) δ ppm 1.74 (d, J=6.57 Hz, 3H) 5.91-5.99 (m, 3H) 6.82 (d, J=1.26 Hz, 1H) 7.46 (t, J=8.72 Hz, 1H) 7.56 (dd, J=8.97, 4.93 Hz, 1H) 7.62 (d, J=1.52 Hz, 1H).

5-bromo-3-[1-(2,6-dichloro-3-fluoro-phenyl)-ethoxy]-pyrazin-2-ylamine (racemate)

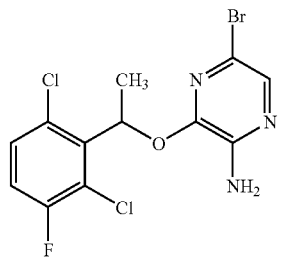

1. 2,6-Dichloro-3-fluoroacetophenone (15 g, 0.072 mol) was stirred in THF (150 mL, 0.5M) at 0° C. using an ice bath for 10 min. Lithium aluminum hydride (from Aldrich, 2.75 g, 0.072 mol) was slowly added. The reaction was stirred at ambient temperature for 3 h. The reaction was cooled in ice bath, and water (3 mL) was added drop wisely followed by adding 15% NaOH (3 mL) slowly. The mixture was stirred at ambient temperature for 30 min. 15% NaOH (9 mL), MgSO₄ were added and the mixture filtered to remove solids. The solids were washed with THF (50 mL) and the filtrate was concentrated to give 1-(2,6-dichloro-3-fluoro-phenyl)-ethanol (14.8 gm, 95% yield) as a yellow oil. ¹H NMR (400 MHz, DMSO-d₆) δ 1.45 (d, 3H), 5.42 (m, 2H), 7.32 (m, 1H), 7.42 (m, 1H).

2. 5-Bromo-3-[1-(2,6-dichloro-3-fluoro-phenyl)-ethoxy]-pyrazin-2-ylamine was prepared following procedure 2 below, from 1-(2,6-dichloro-3-fluoro-phenyl)-ethanol and 3,5-dibromo-pyrazin-2-ylamine. ¹H NMR (400 MHz, DMSO-d₆) δ 1.74 (d, 3H), 6.40 (m, 1H), 6.52 (br s, 2H), 7.30 (m, 1H), 7.48 (m, 1H), 7.56 (s, 1H); MS m/z 382 (M+1).

Enantiomerically Pure Starting Materials

PLE is an enzyme produced by Roche and sold through Biocatalytics Inc. as a crude esterase preparation from pig liver, commonly known as PLE-AS (purchased from Biocatalytics as ICR-123, sold as an ammonium sulfate suspension). The enzyme is classified in the CAS registry as a "carboxylic-ester hydrolase, CAS no. 9016-18-6". The corresponding enzyme classification number is EC 3.1.1.1. The enzyme is known to have broad substrate specificity towards the hydrolysis of a wide range of esters. The lipase activity is determined using a method based on hydrolysis of ethylbutyrate in a pH titrator. 1 LU (lipase unit) is the amount of enzyme which liberates 1 μmol titratable butyric acid per minute at 22° C., pH 8.2. The preparation reported herein (PLE-AS, as a suspension) is usually shipped as an opaque brown-green liquid with a declared activity of >45 LU/mg (protein content around 40 mg/mL).

(1S)-1-(2,6-dichloro-3-fluorophenyl)ethanol (1S)-1-(2,6-dichloro-3-fluorophenyl)ethanol, shown as compound (S-1) in the schemes below, was prepared by a combination of enzymatic hydrolysis of racemic 1-(2,6-dichloro-3-fluorophenyl)ethyl acetate, esterification and chemical hydrolysis with inversion according to Scheme B. Racemic 1-(2,6-dichloro-3-fluorophenyl)ethyl acetate (compound A2) was prepared according to Scheme A.

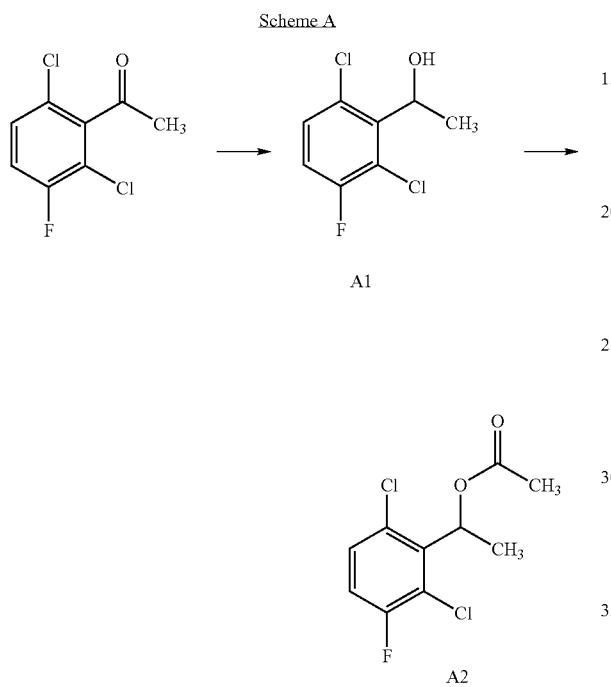

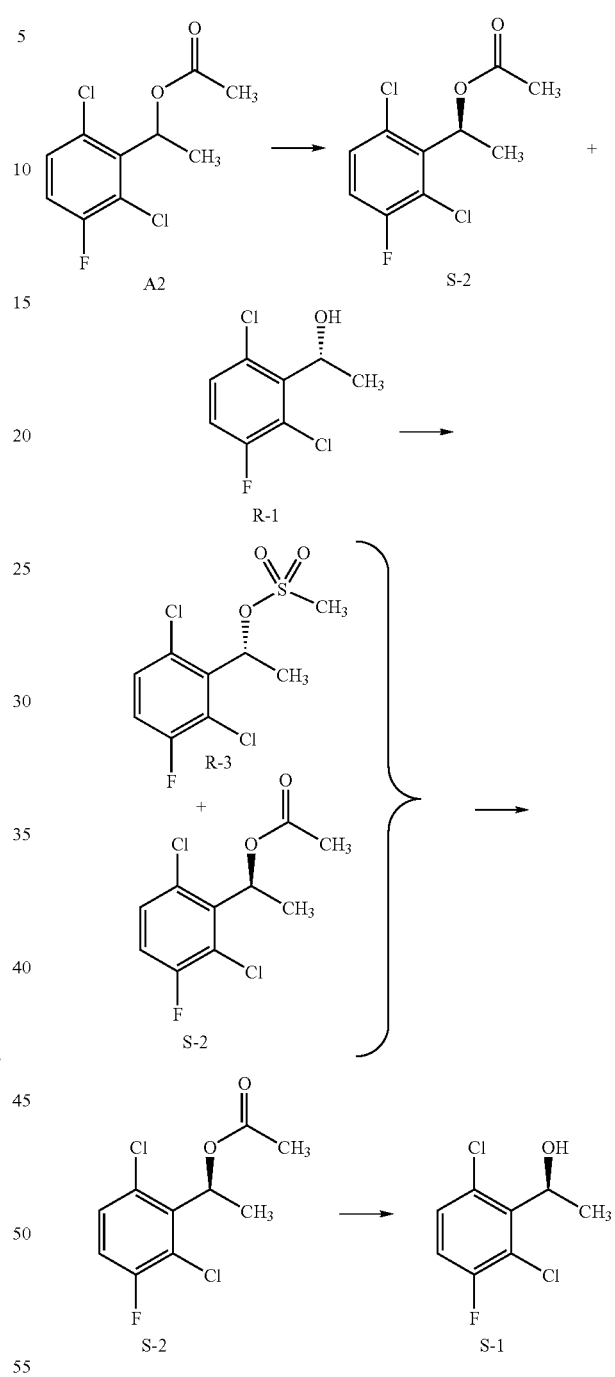

1-(2,6-dichloro-3-fluorophenyl)ethanol (A1): Sodium borohydride (90 mg, 2.4 mmol) was added to a solution of 2',6'-dichloro-3'-fluoro-acetophenone (Aldrich, catalog # 52,294-5) (207 mg, 1 mmol) in 2 mL of anhydrous $CH_3OH$. The reaction mixture was stirred at room temperature for 1 h then was evaporated to give a colorless oil residue. The residue was purified by flash chromatography (eluting with 0→10% EtOAc in hexanes) to give compound A1 as a colorless oil (180 mg; 0.88 mmol; 86.5% yield); MS (APCl) $(M-H)^-$ 208; $^1H$ NMR (400 MHz, chloroform-D) δ ppm 1.64 (d, J=6.82 Hz, 3H) 3.02 (d, J=9.85 Hz, 1H) 6.97-7.07 (m, 1H) 7.19-7.33 (m, 1H).

1-(2,6-dichloro-3-fluorophenyl)ethyl acetate (A2): Acetic anhydride (1.42 mL, 15 mmol) and pyridine (1.7 mL, 21 mmol) were added sequentially to a solution of compound A1 (2.2 g, 10.5 mmol) in 20 mL of $CH_2Cl_2$. The reaction mixture was stirred at room temperature for 12 h and then evaporated to give a yellowish oil residue. The residue was purified by flash chromatography (eluting with 7→9% EtOAc in hexanes) to give compound A2 as a colorless oil (2.26 g; 9.0 mmol; 85.6% yield); $^1H$ NMR (400 MHz, chloroform-D) δ ppm 1.88 (d, J=6.82 Hz, 3H) 2.31 (s, 3H) 6.62 (q, J=6.82 Hz, 1H) 7.25 (t, J=8.46 Hz, 1H) 7.49 (dd, J=8.84, 5.05 Hz, 1H).

To a 50 mL jacketed flask equipped with a pH electrode, an overhead stirrer and a base addition line (1M NaOH), was added 1.2 mL of 100 mM potassium phosphate buffer pH 7.0 and 0.13 mL of PLE AS suspension. Then, compound A2 (0.13 g, 0.5 mmol, 1.00 eq) was added dropwise and the resulting mixture was stirred at room temperature for 20 h, maintaining the pH of the reaction constant at 7.0 using 1 M NaOH. Both the conversion and ee's of the reaction were monitored by RP-HPLC, and stopped after 50% starting material was consumed (approximately 17 hours under these conditions). The mixture was then extracted three times with 10 mL of ethyl acetate to recover both ester and alcohol as a mixture of R-1 and S-2.

Methanesulfonyl chloride (0.06 mL, 0.6 mmol) was added to a solution of a mixture of R-1 and S-2 (0.48 mmol) in 4 mL of pyridine under nitrogen atmosphere. The reaction mixture was stirred at room temperature for 3 h then evaporated to obtain an oil. Water (20 mL) was added to the mixture and then EtOAc (20 mL×2) was added to extract the aqueous solution. The organic layers were combined, dried, filtered, and evaporated to give a mixture of R-3 and S-2. This mixture was used in the next step reaction without further purification. $^1$H NMR (400 MHz, chloroform-D) δ ppm 1.66 (d, J=7.1 Hz, 3H) 1.84 (d, J=7.1 Hz, 3H) 2.09 (s, 3H) 2.92 (s, 3H) 6.39 (q, J=7.0 Hz, 1H) 6.46 (q, J=6.8 Hz, 1H) 6.98-7.07 (m, 1H) 7.07-7.17 (m, 1H) 7.23-7.30 (m, 1H) 7.34 (dd, J=8.8, 4.80 Hz, 1H).

Potassium acetate (0.027 g, 0.26 mmol) was added to a mixture of R-3 and S-2 (0.48 mmol) in 4 mL of DMF under nitrogen atmosphere. The reaction mixture was heated to 100° C. for 12 h. Water (20 mL) was added to the reaction mixture and EtOAc (20 mL×2) was added to extract the aqueous solution. The combined organic layer was dried, filtered, and evaporated to give an oil of S-2 (72 mg, 61% yield in two steps). Chirality ee: 97.6%. $^1$H NMR (400 MHz, chloroform-D) δ ppm 1.66 (d, J=7.1 Hz, 3H) 2.09 (s, 3H) 6.39 (q, J=6.8 Hz, 1H) 7.02 (t, J=8.5 Hz, 1H) 7.22-7.30 (m, 1H).

Sodium methoxide (19 mmol; 0.5 M in methanol) was added slowly to compound S-2 (4.64 g, 18.8 mmol) under a nitrogen atmosphere at 0° C. The resulting mixture was stirred at room temperature for 4 hours. The solvent was evaporated and H$_2$O (100 mL) was added. The cooled reaction mixture was neutralized with sodium acetate-acetic acid buffer solution to pH 7. Ethyl acetate (100 mL×2) was added to extract the aqueous solution. The combined organic layers were dried over Na$_2$SO$_4$, filtered, and evaporated to obtain a white solid (4.36 g, 94.9% yield); SFC-MS: 97% ee. $^1$H NMR (400 MHz, chloroform-D) δ ppm 1.65 (d, J=6.8 Hz, 3H) 5.58 (q, J=6.9 Hz, 1H) 6.96-7.10 (m, 1H) 7.22-7.36 (m, 1H).

3-[(1R)-1-(2,6-dichloro-3-fluorophenyl)ethoxy]-2-nitropyridine

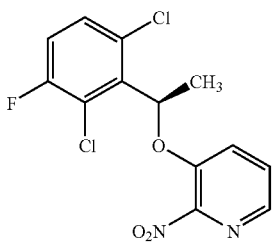

3-Hydroxy-2-nitropyridine (175 mg, 1.21 mmol) and triphenylphosphine (440 mg, 1.65 mmol) were added sequentially to a stirred solution of (1S)-1-(2,6-dichloro-3-fluorophenyl)ethanol (229.8 mg, 1.1 mmol) in THF (10 mL) under a nitrogen atmosphere. The reaction mixture was maintained at room temperature for 1 h and then diisopropyl azodicarboxylate (0.34 mL, 1.65 mmol) was added at 0° C. The mixture was stirred for an additional 12 h. The reaction mixture was evaporated under vacuum to give an oil. The residue was purified by flash chromatography (eluting with 20→25% EtOAc in hexanes) to give the title compound as a white solid (321.5 mg; 0.97 mmol; 88.3% yield); MS (APCI) (M+H)$^+$ 331; SFC-MS: 99.5% ee. $^1$H NMR (400 MHz, chloroform-D) δ ppm 1.85 (d, J=6.6 Hz, 3H) 6.10 (q, J=6.6 Hz, 1H) 7.04-7.13 (m, 1H) 7.21 (dd, J=8.5, 1.14 Hz, 1H) 7.30 (dd, J=9.0, 4.9 Hz, 1H) 7.37 (dd, J=8.6, 4.6 Hz, 1H) 8.04 (dd, J=4.6, 1.3 Hz, 1H).

3-[(1R)-1-(2,6-dichloro-3-fluorophenyl)ethoxy]pyridin-2-amine

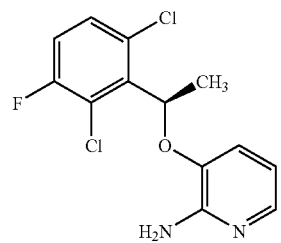

Iron (365 mg) was added to a stirred solution of 3-[(1R)-1-(2,6-dichloro-3-fluorophenyl)ethoxy]-2-nitropyridine (321 mg, 0.97 mmol) in a mixture of EtOH (2 mL) and 2M HCl (0.2 mL) at 0° C. The resulting solution was heated to 85° C. for 2 h. Celite (0.5 g) was added to the cooled reaction mixture. This mixture was filtered over a bed of celite and evaporated to give the title compound as a dark oil. MS (APCI) (M+H)$^+$ 301.

5-bromo-3-[1(R)-(2,6-dichloro-3-fluoro-phenyl)-ethoxy]-pyridin-2-ylamine

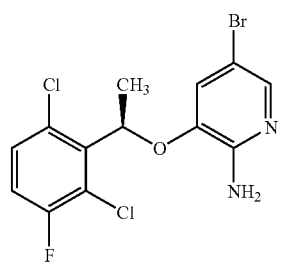

The enantiomerically pure R isomer was prepared as described above for the racemate, but using the enantiomerically pure starting materials described above. $^1$H NMR (400 MHz, DMSO-d$_6$) δ 1.74 (d, 3H), 6.40 (m, 1H), 6.52 (br s, 2H), 7.30 (m, 1H), 7.48 (m, 1H), 7.56 (s, 1H); MS m/z 382 (M+1).

5-iodo-3-[(R)1-(2,6-dichloro-3-fluoro-phenyl)-ethoxy]-pyridin-2-ylamine

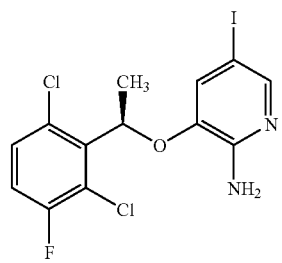

Periodic acid (60 mg, 0.24 mmol), iodine (130 mg, 0.5 mmol), and sulfuric acid (0.03 mL) were added sequentially to a stirred solution of 3-[(1R)-1-(2,6-dichloro-3-fluorophenyl)ethoxy]pyridin-2-amine (0.97 mmol) in a mixture of acetic acid (3 mL) and H$_2$O (0.5 mL). The resulting solution was heated to 80° C. for 5 h. The cooled reaction mixture was quenched with Na$_2$SO$_3$ (80 mg) and basicified with saturated Na$_2$CO$_3$ (2×100 mL) to pH 7. CH$_2$Cl$_2$ (2×50 mL) was added to extract the aqueous solution. The combined organic layers were dried over Na$_2$SO$_4$ then filtered and concentrated under vacuum. The residue was purified by flash chromatography (eluting with 35→40% EtOAc in hexanes) to give the title compound as a yellow oil (254 mg; 0.6 mmol; 61.6% yield); MS (APCI) (M+H)$^+$ 426. $^1$H NMR (400 MHz, chloroform-D) δ ppm 1.81 (d, J=6.8 Hz, 3H) 4.86 (s, 2H) 5.98 (q, J=6.57 Hz, 1H) 6.96 (d, J=1.5 Hz, 1H) 7.08 (dd, J=9.0, 8.0 Hz, 1H) 7.31 (dd, J=8.8, 4.8 Hz, 1H) 7.78 (d, J=1.8 Hz, 1H).

5-bromo-3-[(R)-1-(2,6-dichloro-3-fluoro-phenyl)-ethoxy]-pyrazin-2-ylamine

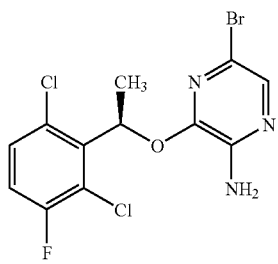

The title compound was prepared according to procedure 2, from (1S)-1-(2,6-dichloro-3-fluorophenyl)ethanol. $^1$H NMR (400 MHz, DMSO-d$_6$) δ 7.53 (s, 1H), 7.48 (m, 1H), 7.39 (t, 1H), 6.48 (s, 2H), 6.41 (q, 1H), 1.74 (d, 3H); LCMS: 381 [M+1]; c-Met Ki: 0.796 μM.

General Scheme I for the Synthesis of 5-Aryl-3-(Substituted-Benzyloxy)-Pyridin-2-ylamine (6)

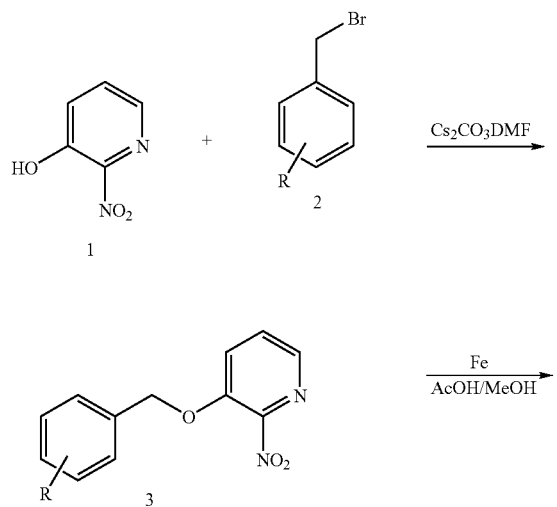

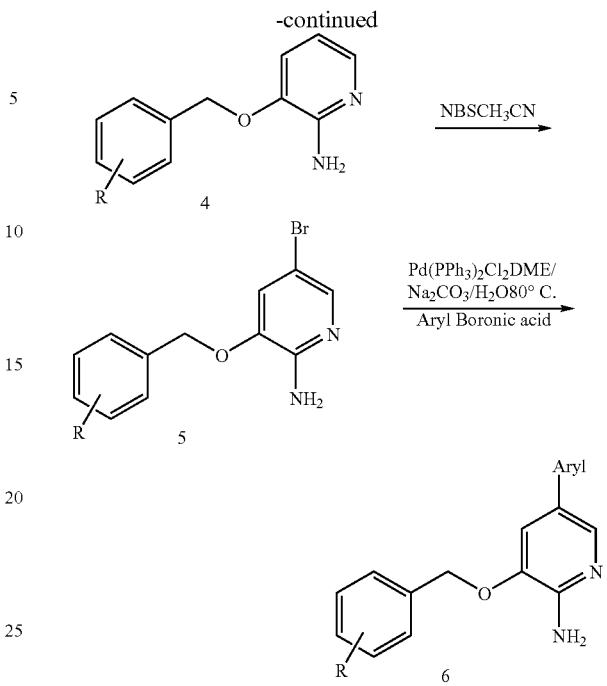

General Procedure 1 for the Synthesis of 5-Bromo-3-(Substituted-Benzyloxy)-Pyridin-2-ylamine (5)

1. Preparation of 3-(substituted-benzyloxy)-2-nitro-pyridine (3): To a stirred solution of Cs$_2$CO$_3$ (1.0 molar equivalent)) in DMF (0.2 M) under a N$_2$ atmosphere containing 3-hydroxy-4-nitro-pyridine (Aldrich, 1.0 molar equivalent) is added substituted benzyl bromide (1.0 molar equivalent). The mixture is stirred for 6 h at ambient temperature. The reaction is then diluted with EtOAc, and partitioned with H$_2$O. The aqueous layer is extracted with EtOAc twice. The organic layers are then combined, washed with H$_2$O and brine, dried over Na$_2$SO$_4$, filtered, and concentrated to dryness under vacuum to yield 3-(substituted-benzyloxy)-2-nitro-pyridine (3) as a solid.

2. Preparation of 3-(substituted-benzyloxy)-pyridin-2-ylamine (4): To a stirred mixture of AcOH and EtOH (1.3:1) is suspended 3-(substituted-benzyloxy-2-nitro-pyridine (1.0 molar equivalent, 1 M) and iron chips (1.0 molar equivalent). The reaction is heated slowly to reflux and allowed to stir for 1 hr. The reaction is cooled to room temperature then filtered through a pad of celite. The resulting filtrate is neutralized with conc. NH$_4$OH, and then extracted with EtOAc for three times. The combined organic extracts are washed with saturated NaHCO$_3$, H$_2$O, and brine, dried over Na$_2$SO$_4$, filtered and concentrated to dryness under vacuum to yield 3-(substituted-benzyloxy)-pyridin-2-ylamine (4) as a solid.

3. Preparation of 5-bromo-3-(substituted benzyloxy)-pyridin-2-ylamine (5): A stirring solution of 3-(substituted-benzyloxy)-pyridin-2-ylamine (4) (1.0 molar equivalent) in acetonitrile is cooled to 0° C. using an ice bath. To this solution is added N-bromosuccinimide (Aldrich, 1.0 molar equivalent) portionwise. The reaction is stirred at 0° C. for 15 min. The reaction is concentrated to dryness under vacuum. The resulting dark oil is dissolved in EtOAc and partitioned with H$_2$O. The organic is then washed with saturated NaHCO$_3$ twice and brine once. Activated charcoal is added to the organic layer and warmed to reflux. The solution is then cooled to room temperature and filtered through a pad of celite. The organic is then concentrated to dryness under vacuum to one third the original volume. The solids are then filtered off to yield 5-bromo-3-(substituted benzyloxy)-pyridin-2-ylamine (5) as a solid.

General Scheme II for the Synthesis of 5-Aryl-3-(Substituted-Benzyloxy)-Pyrazin-2-ylamine

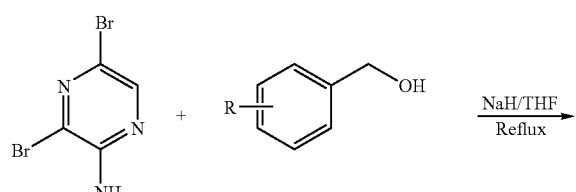

ture was concentrated, diluted with ethyl acetate, and washed with brine. The organic layer was dried over anhydrous magnesium sulfate and concentrated in vacuum. The crude product was purified using a silica gel eluting with 1:1 ethyl acetate/dichloromethane to yield the 5-bromo-3-(substituted-benzyloxy)-pyrazin-2-ylamine as a white solid in 60-90% yield.

General Procedure 3 for the Synthesis of 5-Aryl-3-(Substituted-Benzyloxy)-Pyridin-2-ylamine and 5-Aryl-3-(Substituted-Benzyloxy)-Pyrazin-2-ylamine

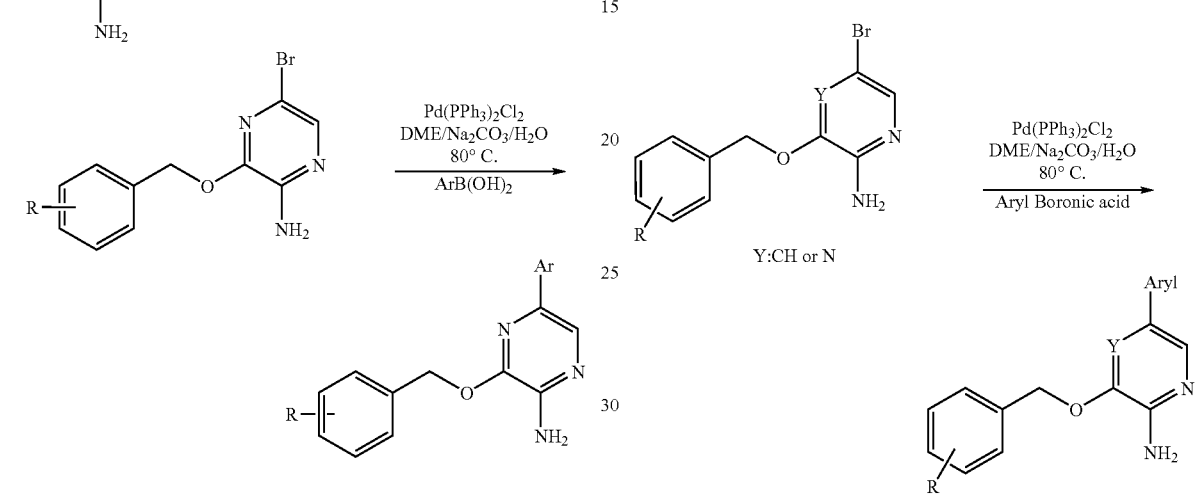

General Procedure 2 for the Synthesis of 5-Bromo-3-(Substituted-Benzyloxy)-Pyrazin-2-ylamine

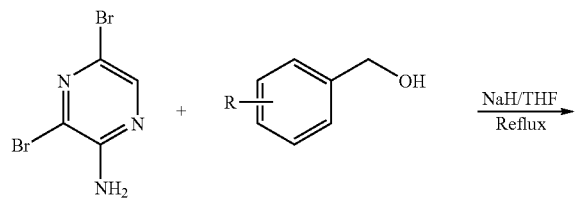

To an ice cooled solution of substituted benzyl alcohol (1.0 molar equivalent) and anhydrous tetrahydrofuran (0.14 M) was added sodium hydride (1.0 molar equivalent) slowly under nitrogen atmosphere. After stirring for 30 minutes, 3,5-dibromopyrazin-2-ylamine (1.0 molar equivalent) in tetrahydrofuran (0.56 M) was added via an addition funnel at a fast dropwise rate. Once the addition was complete the ice bath was removed and the reaction was refluxed under nitrogen and monitored by reversed phase HPLC. After 18 hr HPLC showed that the majority of the starting 3,5-dibromopyrazin-2-ylamine had been consumed and the reaction was allowed to cool to room temperature. The reaction mix- A mixture of 5-bromo-3-(substituted-benzyloxy)-pyridin-2-ylamine or 5-bromo-3-(substituted-benzyloxy)-pyrazin-2-ylamine (1 molar equivalent), aryl boronic acid or ester (1.2 molar equivalent), bis(triphenylphosphine) palladium II chloride (0.03 molar equivalent) and sodium carbonate (3.0 molar equivalent.) in ethylene glycol dimethyl ether and water (10:0.5, 0.03 M) is de-gassed and charged with nitrogen for three times, and then heated to reflux under nitrogen for overnight. The reaction is cooled to ambient temperature and diluted with ethyl acetate. The mixture is washed with water, brine, dried over $Na_2SO_4$, and purified on a silica gel column to afford 5-aryl-3-(substituted-benzyloxy)-pyridin-2-ylamine, or 5-aryl-3-(substituted-benzyloxy)-pyrazin-2-ylamine.

General Procedure 4 for Amidation Reaction of 6-amino-5-(substituted-benzyloxy)-pyridin-3-yl]-benzoic acid

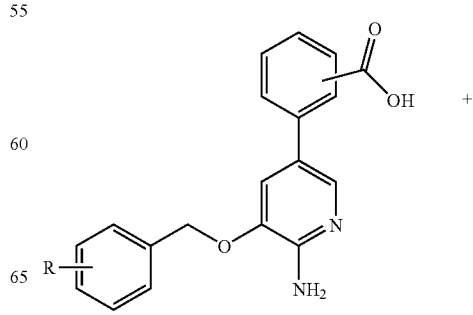

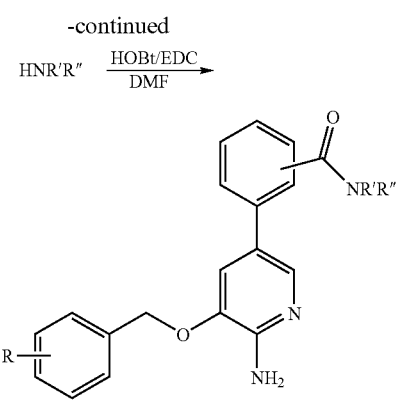
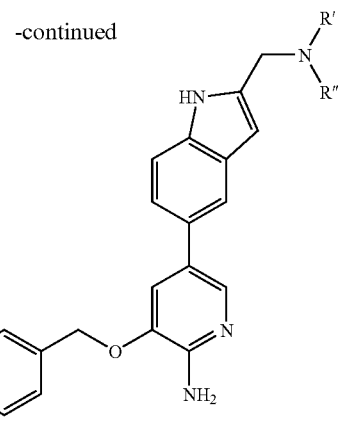

To a solution of 6-amino-5-(substituted-benzyloxy)-pyridin-3-yl]-benzoic acid (1 molar equivalent), 1-hydroxybenzotriazole hydrate (HOBT, 1.2 molar equivalent), and 1-(3-dimethylaminopropyl)-3-ethylcarbodiimide hydrochloride (EDC, 1.2 molar equivalent) in DMF (0.2 M) is added amine (1.2 molar equivalent). The reaction solution is stirred at room temperature for overnight, then diluted with EtOAc, and partitioned with H$_2$O. The organic is separated and the aqueous is extracted with EtOAc. The organic layers are combined, washed with saturated NaHCO$_3$, and concentrated to dryness under vacuum. The material is purified using column chromatography (silica gel, 99:1 to 95:5 CH$_2$Cl$_2$/MeOH). The fractions containing product are concentrated under vacuum to yield the amide product.

General procedure 5 for the preparation of 3-(substituted-benzyloxy)-5-(3-dialkylaminomethyl-1H-indol-5-yl)-pyridin-2-ylamine

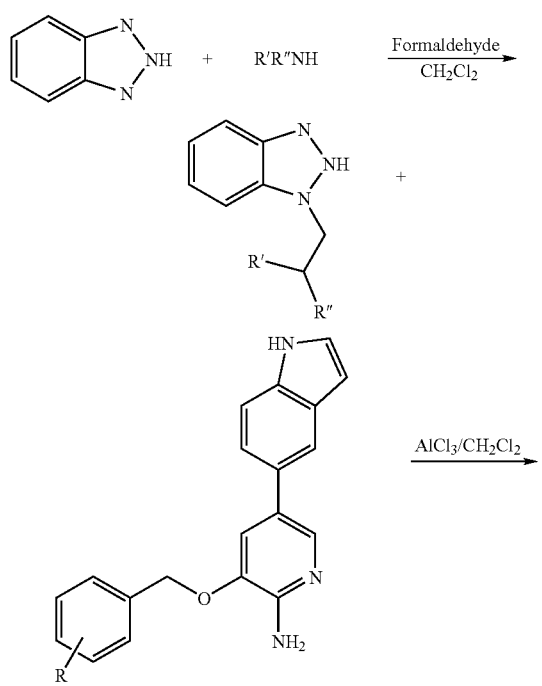

To a solution of benzotriazole (1.0 molar equivalent) in dichloromethane (0.2 M) Is added amine (1.0 molar equivalent). The reaction Is stirred for 5 minutes at room temperature after which formaldehyde (37% by wt, 1.0 molar equivalent) Is added and the reaction capped and stirred at room temperature for 3 h. Once TLC (10% ethyl acetate:dichloromethane) shows the consumption of starting benzotriazole the reaction is dried with anhydrous magnesium sulfate (10 g), filtered and concentrated in vacuo. The crude product is purified with a silica gel column eluting with 1:1 ethyl acetate:dichloromethane to yield the desired product as a white solid.

To a solution of the aminomethylbenzotriazole intermediate (1.0 molar equivalent) in dichloromethane (0.43 M) is added aluminum chloride (2.0 molar equivalent) followed by 3-(2,6-dichloro-benzyloxy)-5-(1H-indol-5-yl)-pyridine-2-ylamin (1.1 molar equivalent). The reaction is capped and heated with stirring to 40° C. for 3-4 h. The reaction is then removed from the heat and allowed to cool to room temperature. The reaction mixture is diluted with sodium hydroxide (0.2 M) and chloroform, recapped and vigorously stirred at room temperature to dissolve the residue in the vial. The chloroform is extracted away from the aqueous, dried over anhydrous sodium sulfate and concentrated in vacuo. The crude product is purified with a silica gel column, first eluting with 1:1, ethyl acetate:dichloromethane, to elute the less polar impurities and then eluting the product with 90:9:1, chloroform:methanol:ammonium hydroxide. (Yields 10-67%.)

General Procedure 6 for the synthesis of 3-(Substituted-benzyloxy)-5-phenyl-pyridin-2-ylamine using 3-(3-methoxy-benzyloxy)-5-phenyl-pyridin-2-ylamine

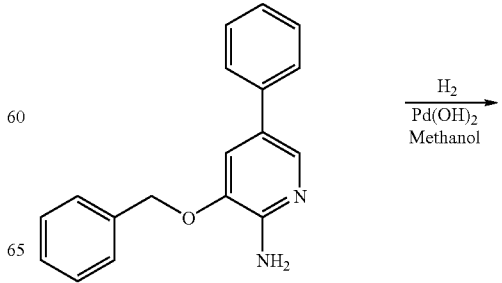

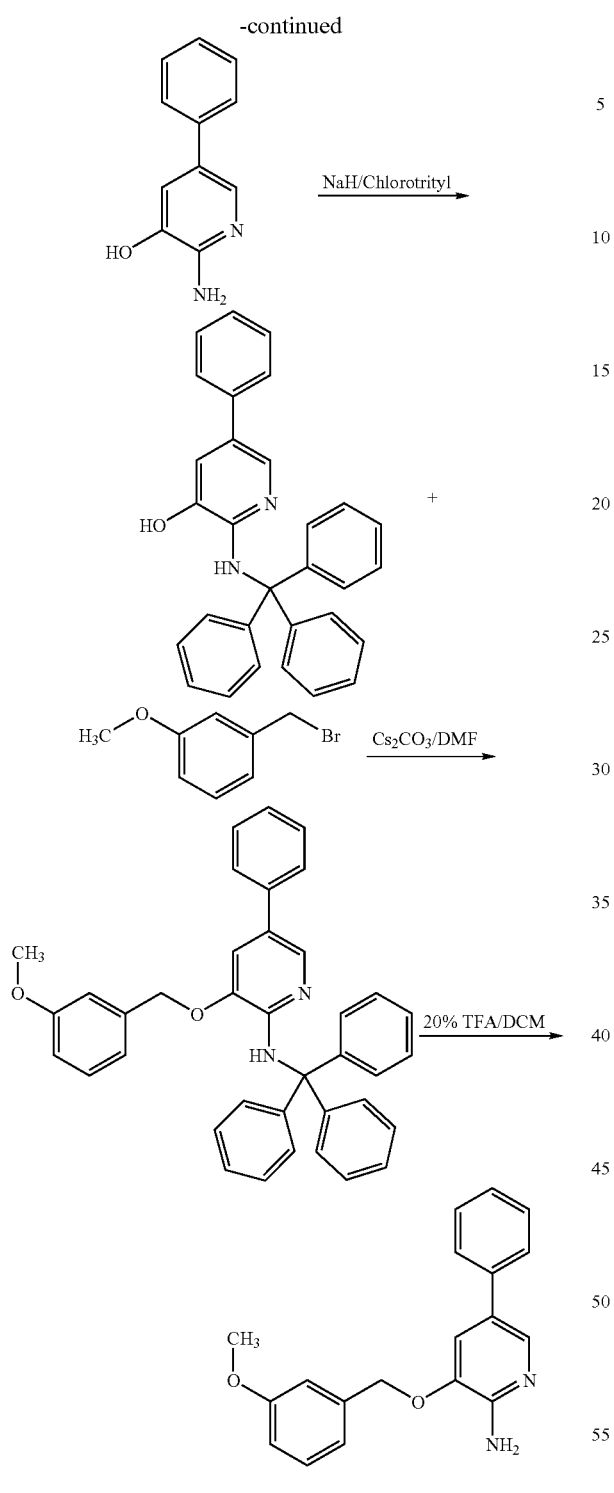

To a solution of 3-benzyloxy-5-phenyl-pyridin-2-ylamine (Example I-87, 3.27 g, 11.8 mmol) in methanol (30 mL) was added Pd(OH)$_2$ (2.5 g, 2.37 mmol). The mixture was degassed and charged with hydrogen three times, and then stirred under hydrogen balloon for 5 h. The reaction was filtered through a celite pad, washed with methanol, and condensed. After high vacuum dry, 2-amino-5-phenyl-pyridin-3-ol was obtained (2.04 g, 93% yield). MS m/z 187 [M+1].

To a solution of 2-amino-5-phenyl-pyridin-3-ol (2.04 g, 10.95 mmol) in THF (anhydrous, 30 mL) was added NaH (1.31 g, 32.85 mmol) slowly. The mixture was stirred under nitrogen for 20 minutes, and then trityl chloride (3.66 g, 13.14 mmol) was added. The reaction was stirred at room temperature for over night under nitrogen. The solvent was evaporated, and the residue was dissolved in dichloromethane, washed with water, and dried over Na$_2$SO$_4$. After filtration and condensation, the crude product was purified on a silica gel column eluting with EtOAc-Hexane (1:10) to provide 5-phenyl-2-(trityl-amino)-pyridin-3-ol (1.09 g, 23% yield). MS m/z 427 [M+1].

To a solution of 5-phenyl-2-(trityl-amino)-pyridin-3-ol (100 mg, 0.24 mmol) in THF (3 mL) was added Cs$_2$CO$_3$ (79 mg, 0.24 mmol). The mixture was stirred at room temperature for 20 minutes, and then 3-methoxybenzylbromide (0.037 mL, 0.26 mmol) was added. The reaction was stirred at room temperature overnight, diluted with dichloromethane (5 mL), and filtered to remove the salts. The solvents were evaporated, and the residue was dissolved in 10% trifluoroacetic acid in dichloromethane (2 mL). The reaction was stirred for 2 hr, and evaporated. The residue was dissolved in dichloromethane, washed by sat. NaHCO$_3$, and dried over Na$_2$SO$_4$. After filtration and concentration, the crude product was purified on a silica gel column eluting with methanol-dichloromethane (from 3% to 15% gradient) to provide 3-(3-methoxy-benzyloxy)-5-phenyl-pyridin-2-ylamine as a white solid (43.5 mg, 60% yield).

General Procedure 7 for the Synthesis of 3-(Substituted-benzyloxy)-5-Aryl-pyridin-2-ylamine using 5-[4-(2-morpholin-4-yl-ethoxy)-phenyl]-3-(3-nitrobenzyloxy)-pyridin-2-ylamine

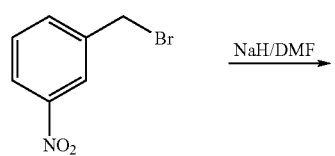

-continued

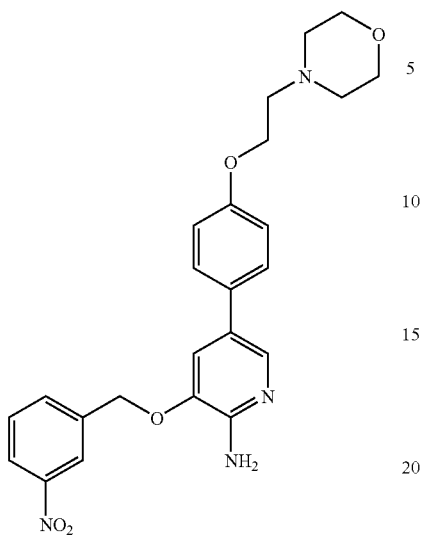

To a solution of 2-amino-5-[4-(2-morpholin-4-yl-ethoxy)-phenyl]-pyridin-3-ol (prepared according to the procedures for 2-amino-5-phenyl-pyridin-3-ol in Example I-88 of U.S. patent application Ser. No. 10/786,610 (PCT/US2004/005495) (45.5 mg, 0.14 mmol) in DMF (3 mL) at 0° C. was added NaH (60% in oil) (5.6 mg, 0.14 mmol) and the mixture was stirred at 0° C. for 20 min. Then 1-bromomethyl-3-nitro-benzene was added and the mixture was stirred at 0° C. for 1 hr and at room temperature for 2 hr. Cold 1 N aqueous HCl (0.1 mL) was added and the solvent was removed under reduced pressure. The residue was purified with silica gel chromatography (CH$_2$Cl$_2$:MeOH:NH$_4$OH=100:3:0.3) to give 5-[4-(2-morpholin-4-yl-ethoxy)-phenyl]-3-(3-nitro-benzyloxy)-pyridin-2-ylamine as yellow solid (44 mg, 68%).

General Procedure 8 for the Synthesis of {4-[6-Amino-5-(substituted-benzyloxy)-pyridin-3-yl]-phenyl}-[(2R)-2-pyrrolidin-1-ylmethyl-pyrrolidin-1-yl]-methanone using {4-[6-amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone

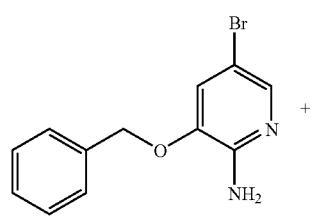 +

-continued

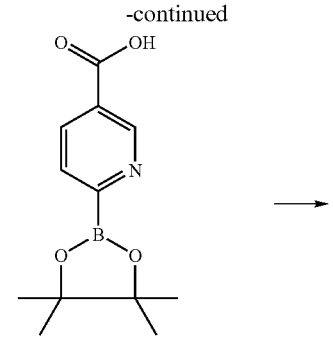

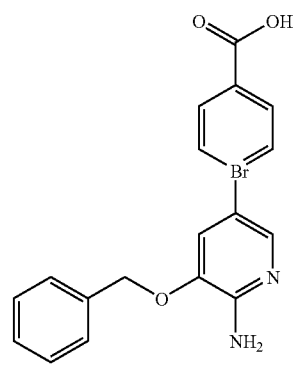

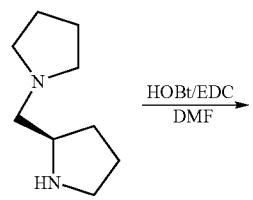

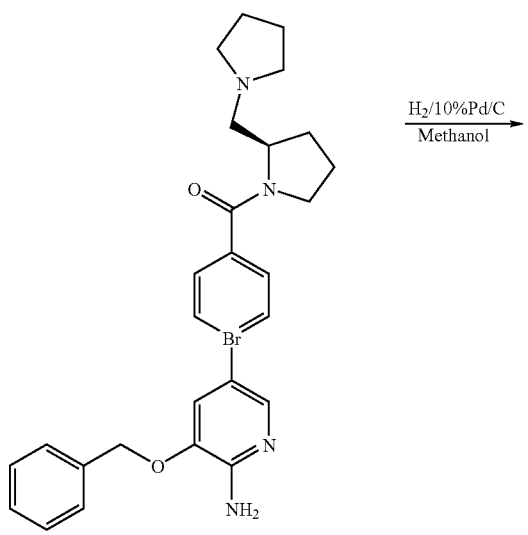

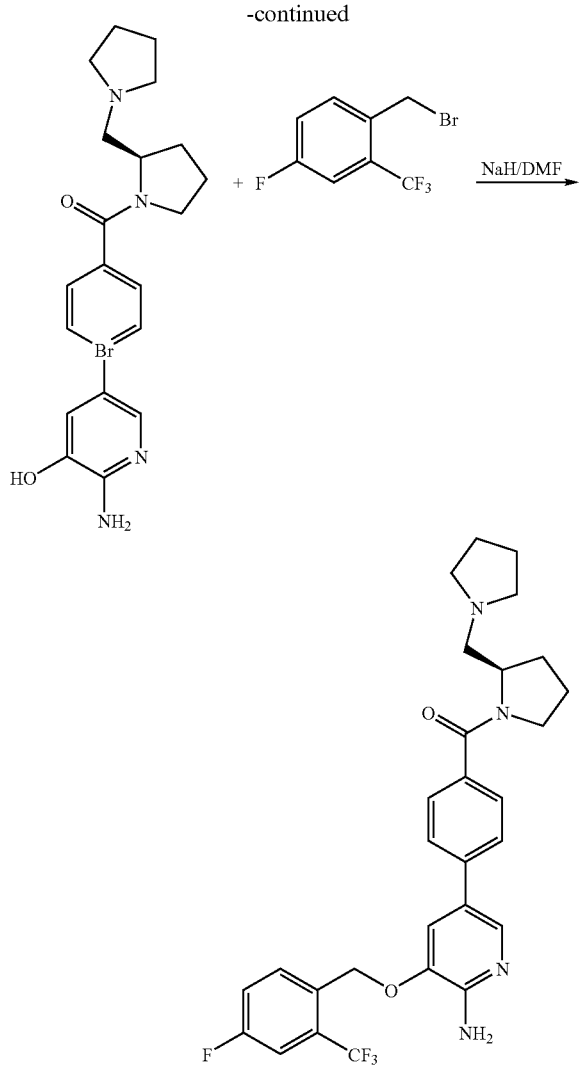

1. 6-Amino-5-benzyloxy-nicotinic acid was prepared according to procedure 3 from 3-benzyloxy-5-bromo-pyridin-2-ylamine and 4-(4,4,5,5-tetramethyl-[1,3,2]dioxaborolan-2-yl)-benzoic acid. MS m/z 321 (M+1).

2. [4-(6-amino-5-benzyloxy-pyridin-3-yl)-phenyl]-[(2R)-2-pyrrolidin-1-ylmethyl-pyrrolidin-1-yl]-methanone was prepared following procedure 4 using 6-amino-5-benzyloxy-nicotinic acid and (2R)-pyrrolidin-1-ylmethyl-pyrrolidine (prepared in Example I-39 of U.S. patent application Ser. No. 10/786,610 (PCT/US2004/005495)). MS m/z 457 (M+1).

3. To a solution of [4-(6-amino-5-benzyloxy-pyridin-3-yl)-phenyl]-[(2R)-pyrrolidin-1-ylmethyl-pyrrolidin-1-yl]-methanone (2.28 g, 5.00 mmol) in methanol (25 mL) was added 10% Pd/C (100 mg). The mixture was degassed and charged with hydrogen for three times, and then stirred under hydrogen balloon overnight. The reaction was filtered through a celite pad, washed with methanol, and condensed. After high vacuum dry, [4-(6-amino-5-hydroxy-pyridin-3-yl)-phenyl]-[(2R)-2-pyrrolidin-1-ylmethyl-pyrrolidin-1-yl)-methanone was obtained (1.74 g, 95% yield). $^1$H NMR (400 MHz, DMSO-$d_6$) δ 7.79 (s, 1H), 7.54 (m, 3H), 7.46 (m, 2H), 7.14 (s, 1H), 5.68 (s, 2H), 4.22 (m, 1H), 3.45 (m, 2H), 2.66 (m, 1H), 2.52 (m, 4H), 1.96 (m, 2H), 1.84 (m, 3H), 1.64 (m, 4H); MS m/z 367 (M+1).

4. To a stirred solution of [4-(6-amino-5-hydroxy-pyridin-3-yl)-phenyl]-[(2R)-2-pyrrolidin-1-ylmethyl-pyrrolidin-1-yl]-methanone (100 mg, 0.27 mmol) in anhydrous DMF (15 mL) under a N$_2$ atmosphere containing, at 0° C., sodium hydride (60% dispersion in mineral oil, 11 mg, 0.49 mmol) was added. The mixture was allowed to stir at 0° C. for 30 min. 1-(Bromomethyl)-4-fluoro-2-(trifluoromethyl)benzene (0.046 mL, 0.27 mmol) was added. The mixture was stirred at room temperature for 2 hr. The reaction was diluted with EtOAc, and partitioned with H$_2$O. The aqueous layer was extracted with EtOAc (2×25 mL). The organic layers were combined, washed with H$_2$O (1×15 mL), brine (1×15 mL), dried over MgSO$_4$, filtered, concentrated, and purified on a silica gel column to yield {4-[6-amino-5-(4-fluoro-2-trifluoromethyl-benzyloxy)-pyridin-3-yl]-phenyl}-[(2R)-2-pyrrolidin-1-ylmethyl-pyrrolidin-1-yl]-methanone as off-white crystals.

General Procedure 9 for the Synthesis 2-Dialkylamino-ethanesulfonic acid [6-amino-5-(substituted-benzyloxy)-pyridin-3-yl]-phenyl-amide using 2-diethylamino-ethanesulfonic acid {4-[6-amino-5-(2-chloro-3,6-difluoro-benzyloxy)-pyridin-3-yl]-phenyl}-amide

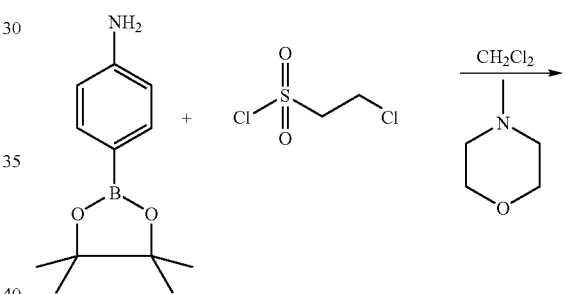

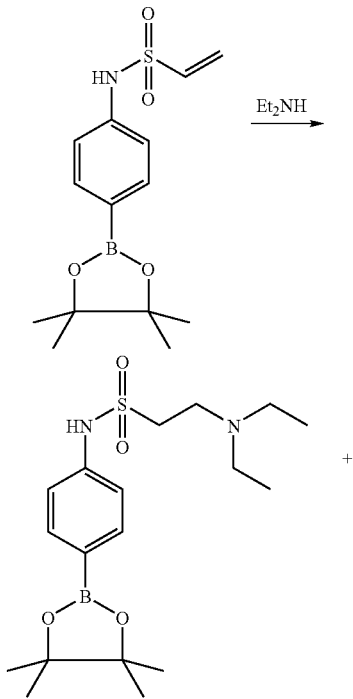

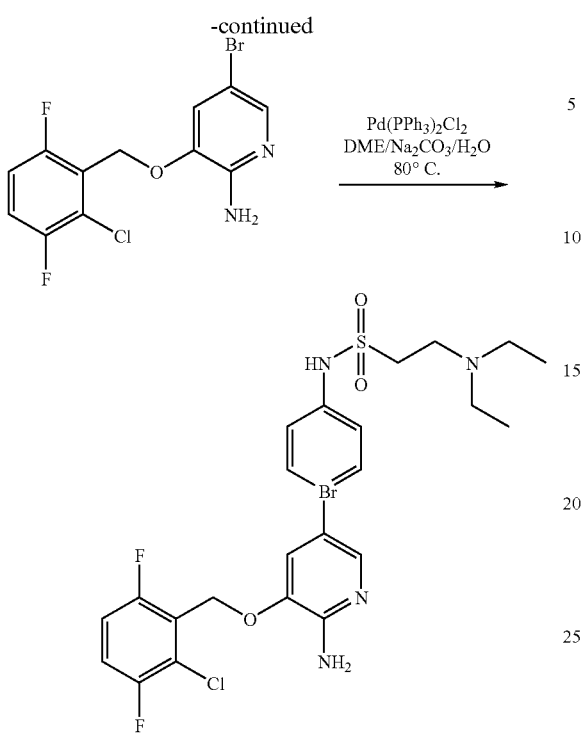

1. To a solution of 4-(4,4,5,5-Tetramethyl-[1,3,2]dioxaborolan-2-yl)-phenylamine (5 g, 22.8 mmol) in dichloromethane (120 mL) was added N-methyl morpholine (7.5 mL, 68.4 mmol). This mixture was cooled to 0° C. under nitrogen atmosphere. 2-Chloroethanesulfonyl chloride (2.5 mL, 23.9 mmol) in dichloromethane (60 mL) was then added drop wise with stirring. Once the addition was complete the flask was stirred at 0° C. for 1 hr and then at room temperature while monitoring by TLC (1:1 ethyl acetate:hexanes) and staining with ninhydrin. After 4 h stirring some starting boronic ester still remained and an additional 0.2 equivalents (0.5 mL) of 2-chloroethanesulfonyl chloride in dichloromethane (25 mL) was added drop wise at room temperature. After 1 hr the boronic ester had been consumed as shown by TLC and the total reaction volume was reduced by one-half via rotary evaporation. The contents were diluted with ethyl acetate (200 mL), washed with 50% brine (2×100 mL), dried over anhydrous sodium sulfate and concentrated in vacuum. The crude product was purified using silica gel (120 g) and eluting with 10% ethyl acetate, dichloromethane to yield ethenesulfonic acid [4-(4,4,5,5-tetramethyl-[1,3,2]dioxaborolan-2-yl)-phenyl]-amide as a white solid (6.2 g, 20.2 mmol, 89% yield). $^1$H NMR (CDCl$_3$, 300 MHz), δ 7.76 (d, J=8.4, 2H), 7.12 (d, J=8.45, 2H) 6.65 (s, 1H), 6.55 (dd, J=9.77, 6.7, 1H), 6.31 (d, J=16.54, 1H), 5.96 (d, J=9.8, 1H), 1.33 (s, 12H).

2. To a solution of ethenesulfonic acid [4-(4,4,5,5-tetramethyl-[1,3,2]dioxaborolan-2-yl)-phenyl]-amide (0.500 g, 1.6 mmol) in methanol (5 mL) was added diethylamine (0.707 g, 4.0 mmol) in methanol (5 mL), and the reaction was stirred at room temperature and monitored by TLC (1:1 Ethyl acetate: hexanes). After 2 hr the reaction was concentrated in vacuum and the residue partitioned between ethyl acetate (50 mL) and water (50 mL). The ethyl acetate was then washed with 50% brine (1×50 mL), dried over anhydrous sodium sulfate, filtered and concentrated in vacuum. Crude product was purified using a 10 g prepacked silica gel column, eluting with 1:1 ethyl acetate:dichloromethane to provide 2-diethylaminoethanesulfonic acid [4-(4,4,5,5-tetramethyl-[1,3,2]dioxaborolan-2-yl)-phenyl]-amide as a white solid (0.346 g, 0.90 mmol, 56%). $^1$H NMR (CDCl$_3$, 300 MHz) δ 7.78 (d, J=6.65, 2H) 7.15 (d, J=6.66, 2H), 3.20 (m, 2H), 3.0 (m, 2H), 2.55 (q, J=7.15, 7.16 4H), 1.34 (s, 12H), 1.05 (t, J=7.19, 6H).

3. 2-diethylamino-ethanesulfonic acid {4-[6-amino-5-(2-chloro-3,6-difluoro-benzyloxy)-pyridin-3-yl]-phenyl}-amide was prepared following the general Suzuki coupling procedure 3 from 5-bromo-3-(2-chloro-3,6-difluoro-benzyloxy)-pyridin-2-ylamine and 2-diethylamino-ethanesulfonic acid [4-(4,4,5,5-tetramethyl-[1,3,2]dioxaborolan-2-yl)-phenyl]-amide prepared in part 2 as a white solid in 60% yield.

General Procedure 10

1: 4-(4,4,5,5-tetramethyl 1,3,2 dioxaboralan-2-yl) aniline (3 g, 0.013 mol) was dissolved in dichloromethane (350 mL) to which pyridine (1.02 g, 0.013 mol) and 4-nitrophenyl chloroformate was added. The reaction was stirred for 13 hr where TLC analysis showed consumption of all starting materials. The solution was washed with saturated NaHCO$_3$ (3×50 mL), water (3×50 mL) and brine (3×50 mL). The organic layer was dried over Na$_2$SO$_4$ and solvent removed to yield a white crystalline solid [4-(4,4,5,5-Tetramethyl-[1,3,2]dioxaborolan-2-yl)-phenyl]-carbamic acid phenyl ester, 4.45 g, 91%. $^1$H NMR (CDCl$_3$ 300 MHz) δ 1.4 (s, 12H), 7.1 (brs, 1H), 7.3 (d, 2H), 7.5 (d, 2H), 7.8 (d, 2H), 8.3 (d, 2H).

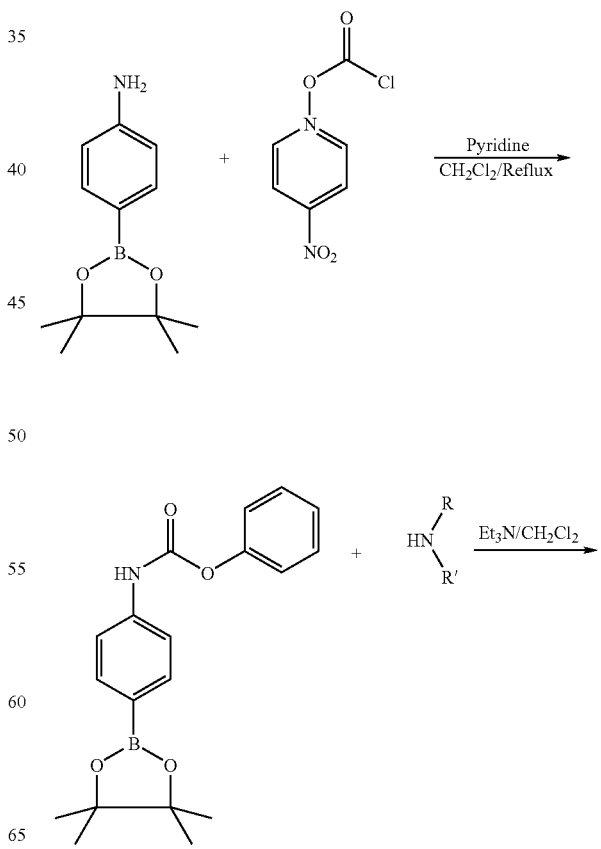

General Procedure 11

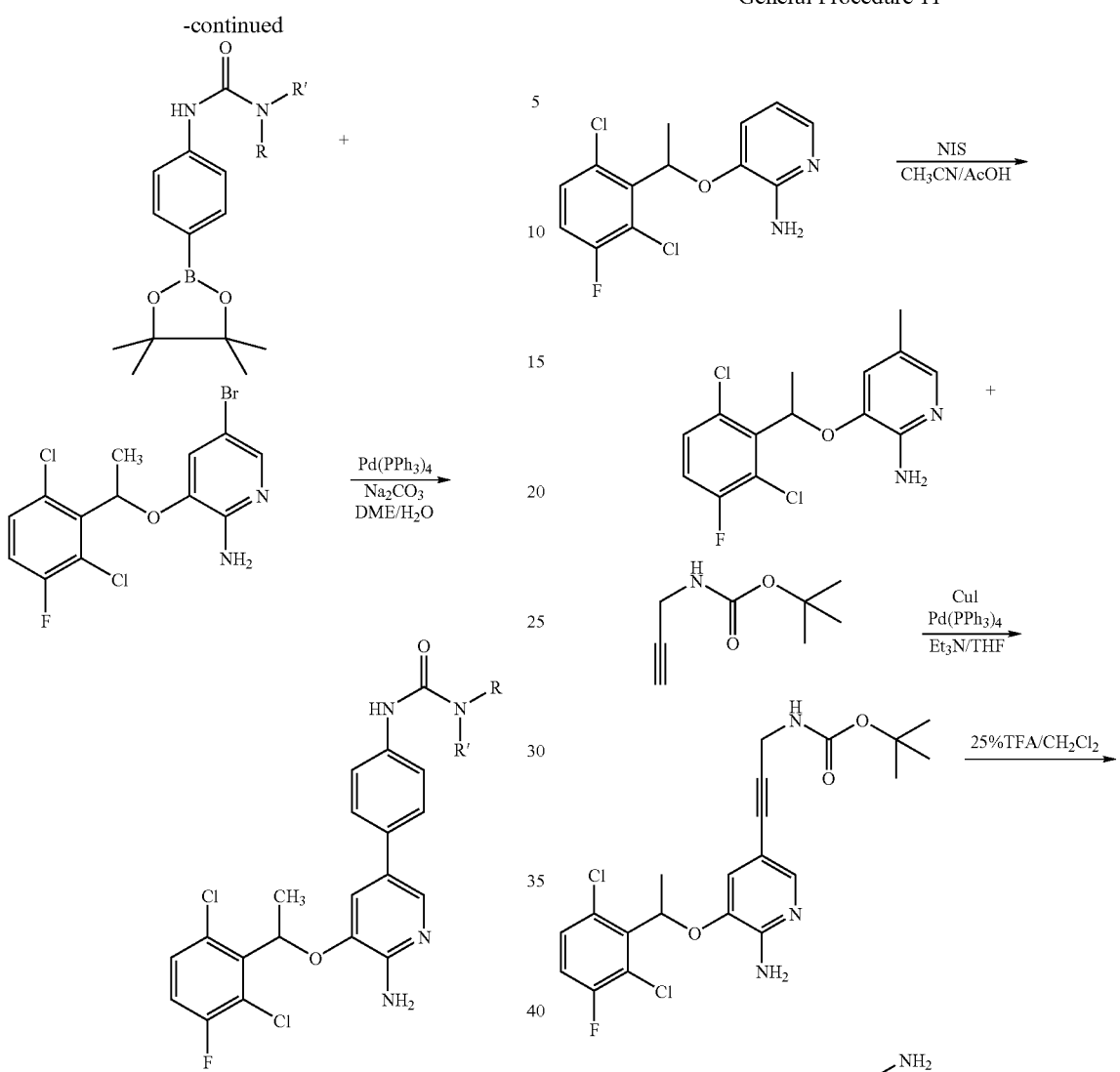

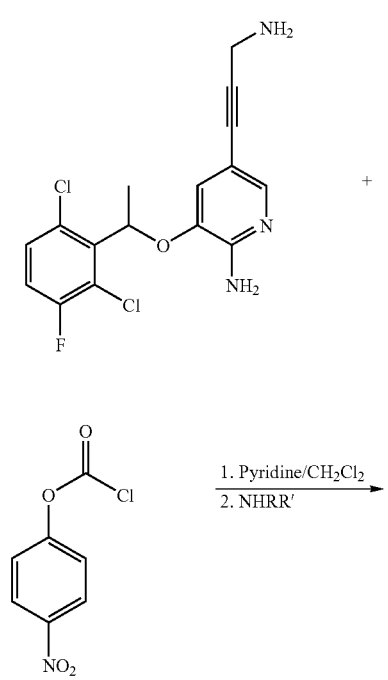

2: [4-(4,4,5,5-Tetramethyl-[1,3,2]dioxaborolan-2-yl)-phenyl]-carbamic acid phenyl ester (500 mg, 1.3 mmol) was dissolved in anhydrous dichloromethane (0.5 mL) and trethylamine (0.187 mL, 1.3 mmol). To this stirred solution was added 1-methyl piperazine (or any other amine) (0.144 mL, 1.3 mmol). The solution turned yellow instantly, and tlc analysis showed consumption of all starting material. The reaction was washed with water (3×500 mL), saturated sodium bicarbonate (2×200 mL) and dried prior to removal of solvents in vacuo. The boronic esters were used without purification.

3: To a mixture of 2.1 mL of DME and 2.8 mL of 2N $Na_2CO_3$ was added 100 mg of the bromide scaffold, 1 equivalent of the boronic acid, and 5 mol % of $Pd(PPh_3)_4$. The reaction was stirred and heated at 80° C. overnight in a two dram vial. The crude mixture was filtered through ceolite and extracted with EtOAc (2×100 mL). The combined extracts were washed with $NaHCO_3$ (1×100 mL), followed by water (1×100 mL), and then saturated brine (1×100 mL). The resulting mixture was concentrated in vacuum. The residue was dissolved in hexane and purified via column chromatography.

-continued

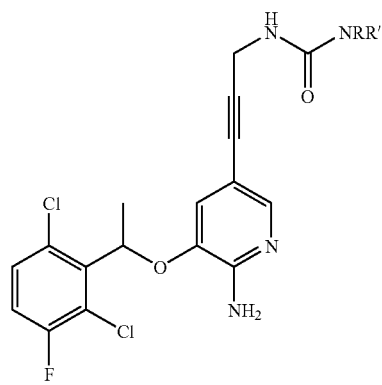

1: To a solution of 3-[1-(2,6-Dichloro-3-fluoro-phenyl)-ethoxy]-pyridin-2-ylamine (10.0 g, 33.2 mmol) in acetonitrile (600 mL) and acetic acid (120 mL) was added N-iodosuccinimide (11.2 g, 49.8 mmol). The mixture was stirred at room temperature for 4 hr and the reaction was quenched with $Na_2S_2O_5$ solution. After evaporation, the residue was partitioned between ethyl acetate and water. The organic layer was washed with 2N NaOH solution, brine, and dried over $Na_2SO_4$. The crude product was purified on a silica gel column to provide 3-[1-(2,6-dichloro-3-fluoro-phenyl)-ethoxy]-5-iodo-pyridin-2-ylamine (7.1 g, 50% yield). MS m/z 427 [M+1]

2: To a solution of 3-[1-(2,6-Dichloro-3-fluoro-phenyl)-ethoxy]-5-iodo-pyridin-2-ylamine (7.1 g, 16.6 mmol) and prop-2-ynyl-carbamic acid tert-butyl ester (3.1 g, 20.0 mmol) in THF (60 mL) and $Et_3N$ (60 mL) was added CuI (63 mg, 0.3 mmol) and Pd(PPh$_3$)$_4$ (384 mg, 0.3 mmol). The mixture was stirred under nitrogen and monitored by TLC until the reaction was complete. The mixture was extracted with EtOAc and washed by water. The crude product was purified on a silica gel column eluting with 20-40% EtOAc in hexanes to provide (3-{6-Amino-5-[1-(2,6-dichloro-3-fluoro-phenyl)-ethoxy]-pyridin-3-yl}-prop-2-ynyl)-carbamic acid tert-butyl ester (2.2 g, 29% yield).

3: The solution of (3-{6-Amino-5-[1-(2,6-dichloro-3-fluoro-phenyl)-ethoxy]-pyridin-3-yl}-prop-2-ynyl)-carbamic acid tert-butyl ester in 25% TFA in dichloromethane was stirred for 2 hr, then washed by 2N NaOH, water twice, brine, dried over $Na_2SO_4$. After filtration and evaporation, 5-(3-amino-prop-1-ynyl)-3-[1-(2,6-dichloro-3-fluoro-phenyl)-ethoxy]-pyridin-2-ylamine was obtained in 93% yield.

4: To a solution of 5-(3-amino-prop-1-ynyl)-3-[1-(2,6-dichloro-3-fluoro-phenyl)-ethoxy]-pyridin-2-ylamine (0.282 mmol, 1 eq) and 4-nitrophenyl chloroformate (1 eq) in anhydrous dichloromethane (10 mL) was added pyridine (1 eq). The reaction was stirred for 4 hr under nitrogen, and then the selected amine (1 eq) and triethylamine (1 eq) were added. The mixture was refluxed for 5 minutes and cooled to room temperature. The reaction mixture was washed with water. The organic layer was evaporated and purified on a silica gel column eluting with 0-20% methanol in dichloromethane on prepacked silica columns. Final yields varied between 24% and 71%.

General Procedure 12

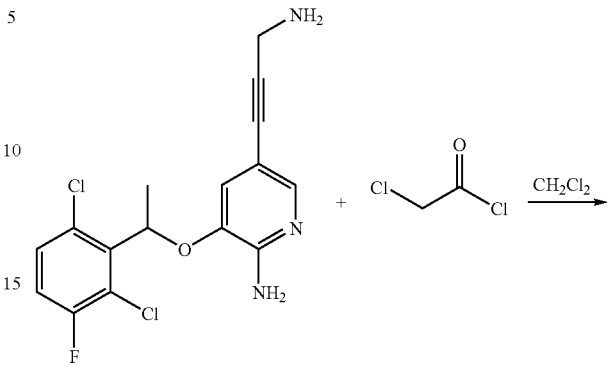

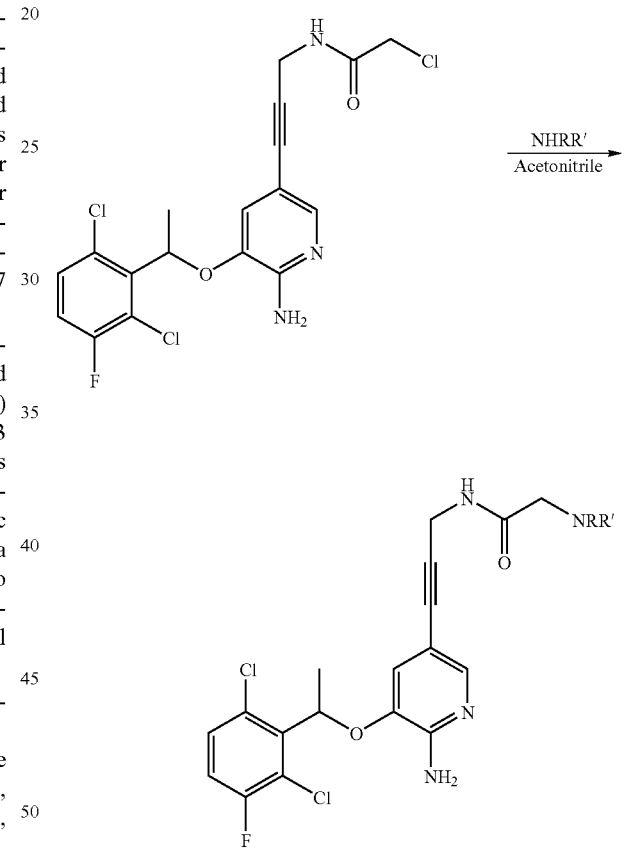

1: To a solution of 5-(3-amino-prop-1-ynyl)-3-[1-(2,6-dichloro-3-fluoro-phenyl)-ethoxy]-pyridin-2-ylamine (prepared in procedure 11) (400 mg, 1.1 mmol) in dichloromethane (17 mL) was added chloroacetyl chloride (153 mg, 1.4 mmol). The reaction was stirred at room temperature with TLC monitor of the completion of the reaction. After the completion, the solvent was evaporated to get the crude product.

2: To a solution of N-(3-{6-Amino-5-[1-(2,6-dichloro-3-fluoro-phenyl)-ethoxy]-pyridin-3-yl}-prop-2-ynyl)-2-chloro-acetamide (1 eq) in acetonitrile (5 eq) was added the individual amine (5 eq). The mixture was refluxing under nitrogen overnight. After evaporation of solvent, the residue was purified on a silica gel column eluting with 1-10% methanol in dichloromethane to provide the product with yields varied between 47% to 97%.

General Procedure 13

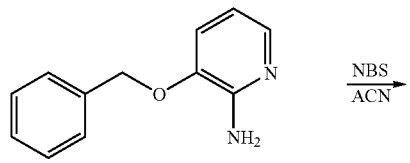

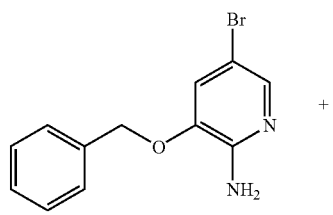

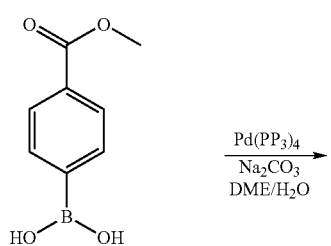

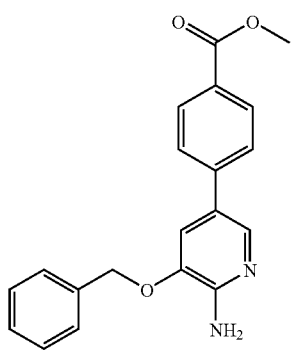

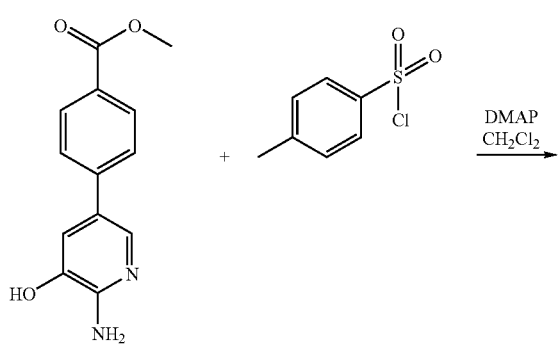

-continued

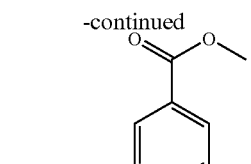

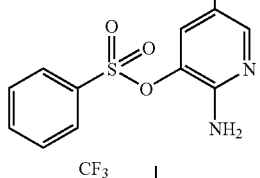

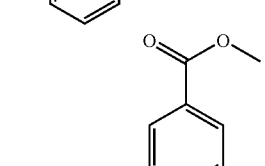

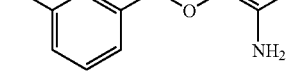

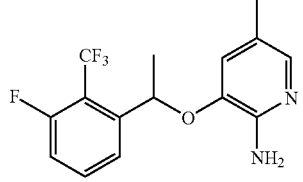

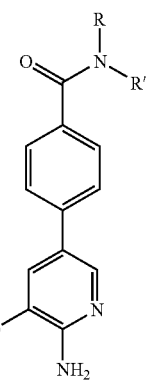

1. To a stirred solution of 2-amino-3-benzyloxypyridine (42.0 g, 0.21 mol) in CH$_3$CN (600 mL) at 0° C. was added N-bromosuccinimide (37.1 g, 0.21 mol) over 30 minutes. The mixture was stirred for 0.5 hr, after which the reaction was then diluted with EtOAc (900 mL) and partitioned with H$_2$O (900 mL). The organic layer was washed with brine and dried (Na$_2$SO$_4$), filtered and concentrated to dryness under vacuum to yield 3-benzyloxy-5-bromo-pyridin-2-ylamine (31.0 g, 0.11 mol, 53%). $^1$H NMR (CDCl$_3$, 300 MHz) 64.63-4.78 (brs, 2H), 5.04 (s, 2H), 7.07 (d, 1H, J, 1.8 Hz), 7.33-7.42 (m, 5H), 7.73 (d, 1H, J, 1.8 Hz).

2. To a stirred mixture of 3-benzyloxy-5-bromo-pyridin-2-ylamine (31.0 g, 0.11 mol) in a mixture of DME (600 mL) and H$_2$O (600 mL) was added 4-carboxymethylboronic acid (29.9 g, 0.11 mol), Pd(PPh$_3$)$_4$ (6.4 g, 5.55 mmol), and Na$_2$CO$_3$ (82.0 g, 0.78 mol). The reaction was heated slowly to reflux and allowed to stir for 3 hr. The reaction was cooled to room temperature, then diluted with CH$_2$Cl$_2$ (1.5 L) and partitioned with H$_2$O (700 mL). The organic layer was washed with saturated NaHCO$_3$ (700 mL), dried (Na$_2$SO$_4$), filtered, and concentrated in vacuo. The crude material was purified by column chromatography (silica gel, 1:1 to 4:1 EtOAc:hexanes) and the fractions containing product were combined and concentrated in vacuo to yield 4-(6-amino-5-benzyloxy-pyridin-3-yl)-benzoic acid methyl ester (29.4 g, 0.086 mol, 79%). $^1$H NMR (CDCl$_3$, 300 MHz) δ 3.92 (s, 3H), 4.82-4.94 (brs, 2H), 5.15 (s, 2H), 7.22 (d, 1H, J, 1.8 Hz), 7.33-7.42 (m, 5H), 7.54 (d, 2H, J, 8.6), 7.98 (d, 1H, J, 1.8 Hz), 8.06 (d, 2H, J, 8.6 Hz).

3. To a stirring solution of 4-(6-amino-5-benzyloxy-pyridin-3-yl)-benzoic acid methyl ester (10.0 g, 0.03 mol) in EtOH:H$_2$O (95:5, 600 mL) was added Pd/C (15.9 g, 0.015 mol) (the reaction was de-gassed under vacuum). The solution was allowed to stir under an H$_2$ atmosphere for 22 hr. The solution was filtered through wet celite and the celite washed with EtOH. The filtrate was concentrated under vacuum to yield 4-(6-Amino-5-hydroxy-pyridin-3-yl)-benzoic acid methyl ester (2.3 g, 9.3 mmol, 31%). $^1$H NMR (MeOD, 300 MHz) δ 3.90 (s, 3H), 7.21 (d, 1H, J, 1.9 Hz), 7.62 (d, 2H, J, 8.5 Hz), 7.76 (d, 1H, J, 1.9 Hz), 8.04 (d, 2H, J, 8.5 Hz).

4. To a stirring solution of 4-(6-amino-5-hydroxy-pyridin-3-yl)-benzoic acid methyl ester (2.3 g, 9.3 mmol) in CH$_2$Cl$_2$ (180 mL) was added N,N-diisopropylethylamine (3.2 mL, 0.019 mol), 4-methyl-benzenesulfonyl chloride (2.66 g, 0.014 mol), and PS-DMAP (catalytic amount). The reaction was stirred at ambient temperature for 6 hr then filtered to remove the resin. The resin was washed with CH$_2$Cl$_2$ (3×20 mL), and the combined fractions were washed with 10% citric acid (100 mL), saturated NaCl (100 mL), dried (Na$_2$SO$_4$) and filtered and concentrated in vacuo. The resulting crude material was purified by column chromatography (silica gel, 100% CH$_2$Cl$_2$ to 95:5 CH$_2$Cl$_2$:MeOH) and the fractions containing the desired product were combined and concentrated in vacuo to yield 4-[6-Amino-5-(toluene-4-sulfonyloxy)-pyridin-3-yl]-benzoic acid methyl ester (3.3 g, 8.2 mmol, 88%). $^1$H NMR (CDCl$_3$, 300 MHz) δ 2.47 (s, 3H), 3.93 (s, 3H), 4.81-4.88 (brs, 2H), 7.36-7.44 (m, 5H), 7.81 (d, 2H, J, 8.3 Hz), 8.05 (d, 2H, J, 8.4 Hz), 8.19-8.27 (brs, 1H).

5. To a stirred solution of 1-(3-fluoro-2-trifluoromethyl-phenyl)-ethanol (2.0 g, 9.6 mmol) in anhydrous DMF (500 mL) at 0° C. under a N$_2$ atmosphere was added NaH (0.38 g, 9.6 mmol). The reaction was allowed to stir for 0.5 hr. A solution of 4-[6-Amino-5-(toluene-4-sulfonyloxy)-pyridin-3-yl]-benzoic acid methyl ester (3.8 g, 9.6 mmol) in anhydrous DMF (30 mL) was added to the reaction mixture which was allowed to come to ambient temperature slowly and stirred for 21 hr at this temperature. The reaction was diluted with EtOAc (500 mL) and H$_2$O (100 mL). The organic layer was separated off and the aqueous was further extracted with EtOAc (1×200 mL). The organic layers were combined and washed with brine (1×100 mL), dried with Na$_2$SO$_4$ and concentrated to dryness under vacuum. The crude mixture was purified by column chromatography (silica gel, 40:60 to 70:30 EtOAc:hexanes) and the fractions containing product were combined and concentrated in vacuo to yield 4-{6-amino-5-[1-(3-fluoro-2-trifluoromethyl-phenyl)-ethoxy]-pyridin-3-yl}-benzoic acid methyl ester (1.4 g, 3.2 mmol, 34%). $^1$H NMR (CDCl$_3$, 300 MHz) δ 1.73 (d, 3H, J, 6.2 Hz), 3.91 (s, 3H), 4.87-4.64 (brs, 2H), 5.81 (q, 1H, J, 6.1, 6.3 Hz), 6.92 (d, 1H, J, 1.8 Hz), 7.38 (d, 2H, J, 8.5 Hz), 7.46-7.66 (m, 3H), 7.93 (d, 1H, J, 1.8 Hz), 8.02 (d, 2H, J, 8.5 Hz).

6. To a stirred solution of 4-{6-amino-5-[1-(3-fluoro-2-trifluoromethyl-phenyl)-ethoxy]-pyridin-3-yl}-benzoic acid methyl ester (1.4 g, 3.2 mmol) in warm IPA (72 mL) was added H$_2$O (38 mL) containing LiOH (0.68 g, 16.2 mmol). The reaction was heated to reflux for 3.5 hr. The reaction was neutralized and diluted with EtOAc (200 mL) and extracted upon cooling. The organic layer was washed with brine (50 mL), dried over Na$_2$SO$_4$ and concentrated under vacuum to yield 4-{6-Amino-5-[1-(3-fluoro-2-trifluoromethyl-phenyl)-ethoxy]-pyridin-3-yl}-benzoic acid (1.2 g, 2.8 mmol, 88%). $^1$H NMR (MeOD, 300 MHz) δ 1.75 (d, 3H, J, 6.2 Hz), 4.88-4.93 (m, 1H), 7.01 (d, 1H, J, 1.8 Hz), 7.39 (d, 2H, J, 8.3 Hz), 7.52-7.67 (m, 3H), 7.80 (d, 1H, J, 1.8 Hz), 7.97 (d, 2H, J, 8.3 Hz).

7. Preparation of amide compounds: A stirring solution of 4-{6-Amino-5-[1-(3-fluoro-2-trifluoromethyl-phenyl)-ethoxy]-pyridin-3-yl}-benzoic acid (50 mg, 0.12 mmol), EDC (27.0 mg, 0.13 mmol) and HOBt (18.0 mg, 0.13 mmol) in DMF (2 mL) was added to a two dram vial containing NHR$_1$R$_2$ (0.12 mmol). The reaction was stirred at room temperature for 18 hr. The reaction was then diluted with CH$_2$Cl$_2$ (3 mL) and partitioned with H$_2$O. The organic was separated washed with saturated NaCl (1×2 mL) and saturated NaHCO$_3$ (1×2 mL). The organic was concentrated to dryness under vacuum. The material was purified using column chromatography (silica gel, 99:1 to 95:5 CH$_2$Cl$_2$/MeOH). The fractions containing product were concentrated under vacuum to yield amide compounds.

General Procedure 14

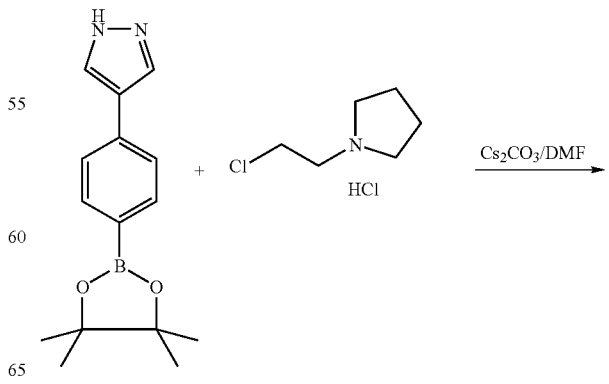

-continued

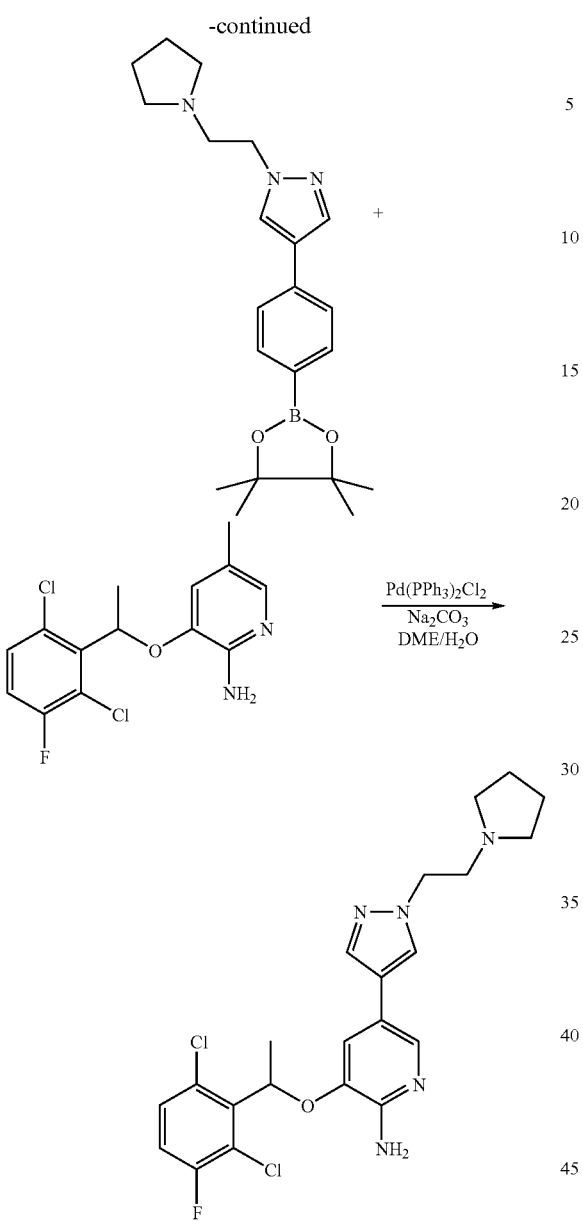

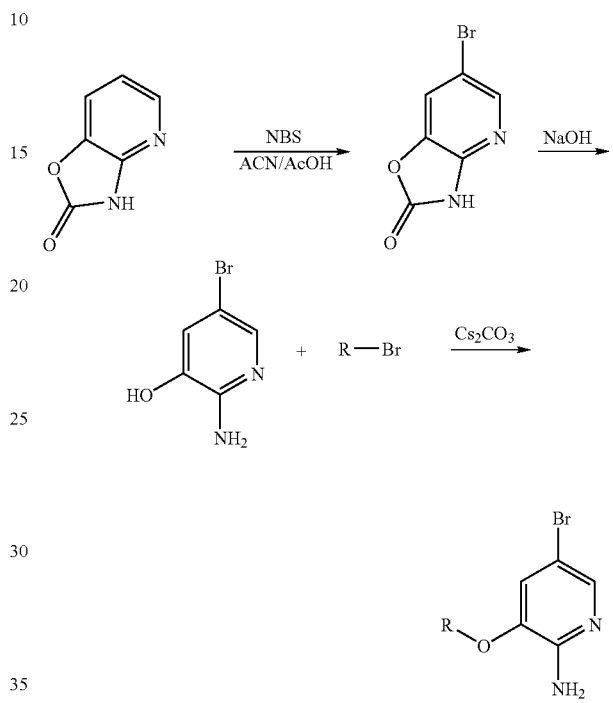

(10 mL). The product was extracted with EtOAc (3×20 mL), dried over Na$_2$SO$_4$, and concentrated. The crude product was purified by reverse phase HPLC with 0.1% TFA in water and acetonitrile.

General Procedure 15

1: To a solution of 3H-oxazolo[4,5-b]pyridin-2-one (13.6 g, 100 mmol) in acetonitrile (600 mL) and acetic acid (120 mL) was added N-bromosuccinimide (21.4 g, 120 mmol). The mixture was stirred at room temperature for 4 hr and the reaction was quenched with Na$_2$S$_2$O$_5$ solution. After evaporation, the residue was partitioned between ethyl acetate and water. The organic layer was washed with 2N NaOH solution, brine, and dried over Na$_2$SO$_4$. The crude product was purified on a silica gel column to provide 6-bromo-3H-oxazolo[4,5-b]pyridin-2-one (11.5 g, 55% yield).

2: 6-Bromo-3H-oxazolo[4,5-b]pyridin-2-one (21.5 g, 100 mmol) was suspended in NaOH solution (2N, 250 mL, 500 mmol). The mixture was refluxed overnight and a clear solution was obtained. After cooling to room temperature, the reaction solution was neutralized to pH ~7. A lot of CO$_2$ was released and also precipitate was observed. The product was filtered, washed with water, and dried under high vacuum to provide 2-amino-5-bromo-pyridin-3-ol as an off-white solid (17.8 g, 98% yield).

1: To a mixture of 1-(2-chloroethyl)pyrrolidine hydrochloride (200 mg, 1.18 mmol) and 4-[4-(4,4,5,5-Tetramethyl-[1,3,2]dioxaborolan-2-yl)-phenyl]-1H-pyrazole (229 mg, 1.19 mmol) in DMF (6 mL) was added Cs$_2$CO$_3$. The mixture was stirred at room temperature overnight. Water (10 mL) was then added to the mixture. The product was extracted with EtOAc (3×10 mL). The combined extracts were then washed with brine (5×10 mL) to remove the DMF, then dried over Na$_2$SO$_4$, and concentrated (142 mg, 41% yield).

2: To a mixture of 3-[1-(2,6-Dichloro-3-fluoro-phenyl)-ethoxy]-5-iodo-pyridin-2-ylamine (200 mg, 0.468 mmol), pinacol boronic ester (1.2 eq), Na$_2$CO$_3$ (149 mg, 1.41 mmol) in water (1.25 mL), and dimethyl ethyl glycol (3.75 mL, 0.1M) was added Pd(PPh$_3$)$_2$Cl$_2$ (16 mg, 0.020 mmol) in a microwave reaction vessel. The system was degassed and charged with nitrogen. The mixture was stirred at 160° C. in a microwave apparatus for 15 minutes. The mixture was cooled to room temperature followed by the addition of water 3: To a solution of 2-amino-5-bromo-pyridin-3-ol (358 mg, 1.89 mmol) in DMF (8 mL) was added Cs$_2$CO$_3$ (620 mg, 1.89 mmol). The mixture was stirred at room temperature under nitrogen for 1 hr. To the reaction mixture was added bromocompound (0.9 eq) in DMF (5 mL) slowly. The reaction solution was stirred under nitrogen for five hr, and then partitioned between water and ethyl acetate. The organic layer was washed with brine for three times, dried over MgSO$_4$.

The crude product was purified on a silica gel column eluting with hexane-ethyl acetate (4:1) to provide the product with 70%-80% yield.

General Procedure 16 using Example I-488 of U.S. patent application Ser. No. 10/786,610 (PCT/US2004/005495)

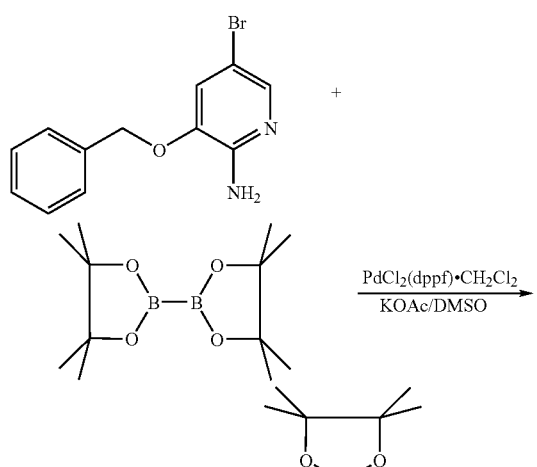

1. To a solution of 3-benzyloxy-5-bromo-pyridin-2-ylamine (1 g, 3.58 mmol) in dimethylsulfoxide (7 mL) was added sequentially bis(pinacolato)diborane (1.0 g, 3.94 mmol), potassium acetate (1.05 g, 10.7 mmol) [1,1'-bis(diphenylphosphino)ferrocine]dichloropalladium (II), complex with dichloromethane (1:1) (146 mg, 0.18 mmol). The mixture was heated to 80° C. for 16 hr and then cooled to room temperature. The reaction mixture was diluted with ethyl acetate (50 mL) and filtered. The filtrate was washed with water (2×50 mL) and dried over magnesium sulfate. Concentration in vacuo yielded the crude boronate as a brown solid (1.13 g, 97%). $^1$H NMR (CDCl$_3$) δ 1.32 (s, 12H), 5.08 (s, 2H), 5.44 (br s, 2H), 7.33-7.42 (m, 6H), 8.03 (s, 1H).

2. An 18 mL reaction vessel was charged with the crude 3-benzyloxy-5-(4,4,5,5-tetramethyl-[1,3,2]dioxaborolan-2-yl)-pyridin-2-ylamine (161 mg, 0.49 mmol), dimethoxyethane (3 mL) and 2-bromopyridine (117 mg, 0.74 mmol). To this solution was added [1,1'-bis(diphenylphosphino)ferrocine]dichloropalladium (II), complex with dichloromethane (1:1) (20 mg, 0.05 mmol) and a 2 M solution of cesium carbonate in water (0.75 mL, 1.5 mmol). The reactor was warmed to 80° C. for 66 hr under a nitrogen atmosphere, then cooled to room temperature. The reaction mixture was partitioned between ethyl acetate (5 mL) and water (5 mL). The organic layer was washed with additional water (5 mL) and diluted with dimethylformamide (5 mL). Polymer-bound sulfonic acid (0.5 g, 2.1 mmol) was added to the organic solution, and the resulting mixture was gently agitated for 2 hr. The resin was filtered and washed with dimethylformamide, methanol and methylene chloride (3×5 mL each solvent). Then the polymer was reacted with 2 M ammonia in methanol for 1 hr. The resin was filtered and washed with additional 2 M ammonia in methanol (2×5 mL), and the combined filtrates were concentrated in vacuo. Purification of the crude product by flash column chromatography yielded 52.2 mg of product as a tan solid (38% yield).

General Procedure 17

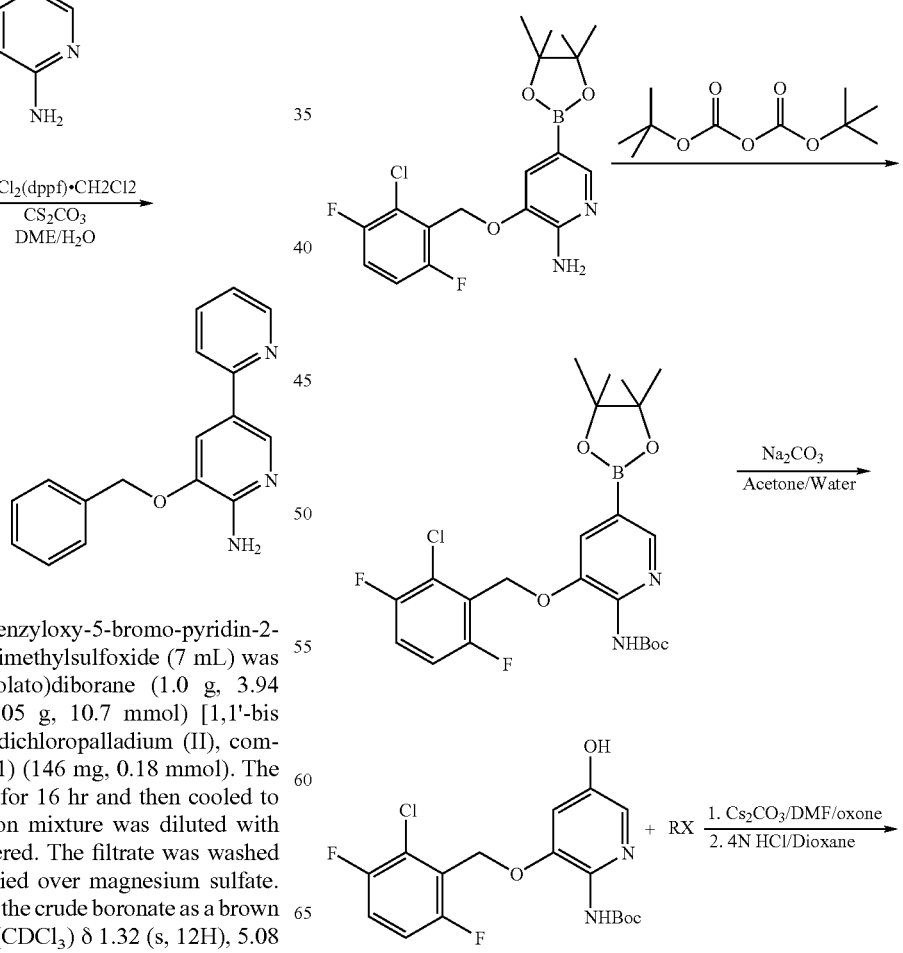

-continued

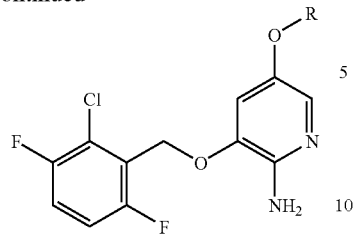

1. To the solution of 3-(2-Chloro-3,6-difluoro-benzyloxy)-5-(4,4,5,5-tetramethyl-[1,3,2]dioxaborolan-2-yl)-pyridin-2-ylamine (procedure 16) (10.0 g, 24.3 mmol) in t-butyl alcohol (50 mL) was added boc anhydride (5.83 g, 26.7 mmol) and reaction stirred at room temperature overnight. Additional boc anhydride (2.25 g, 10.3 mmol) was added and reaction stirred overnight again. Material was concentrated to a viscous black oil and used as-is.

2. The crude boronic ester (24.3 mmol theoretical) in THF (150 mL) was added to a solution of sodium bicarbonate (16.3 g, 194 mmol) in water (150 mL) and acetone (23 mL). The mixture was cooled to 2° C. and oxone (13.5 g, 21.9 mmol) added slowly, keeping temperature below 8° C. Upon completion of addition, reaction was stirred for 5 minutes then quenched with sodium bisulfite (14.2 g) in water (28 mL). Ethyl acetate was added (200 mL) and layers separated. Aqueous layer was neutralized with 6N HCl and extracted with ethyl acetate (2×200 mL). Combined organics were washed with water (250 mL) and brine (250 mL), dried ($Na_2SO_r$) and concentrated to a crude black oil. Silica gel chromatography (ethyl acetate/hexane) gave the product as a light brown foam (4.78 g, 49.0%). $^1$H NMR (CDCl$_3$) δ 1.48 (s, 9H), 1.74 (d, 3H), 5.75 (q, 1H), 6.61 (d, 1H), 76.89 (dt, 1H), 6.94-7.04 (m, 2H), 7.26 (d, 1H), 8.19 (bs, 1H). MS m/z 401 (M+H)$^+$.

3. To cesium carbonate in a 2 dram vial was added [3-(2-Chloro-3,6-difluoro-benzyloxy)-5-hydroxy-pyridin-2-yl]-carbamic acid tert-butyl ester (100 mg, 0.25 mmol) in anhydrous DMF (1 mL) followed by benzyl bromide (89.2 μL, 0.75 mmol). The vial was capped and stirred at 90° C. overnight. Reaction was filtered through a 5 mL Chem-Elut tube pre-wetted with water (3.5 mL) and eluted with 1:1 ethyl acetate:methylene chloride. After partial concentration, 4N HCl in dioxane (1-2 mL) was added and solution concentrated. Reverse phase chromatography (water:acetonitrile, 0.05% TFA) followed by lyophilization, gave the desired product as an off white amorphous solid (25.3 mg, 20.0%) and the bis-addition product as a tan amorphous solid (35.2 mg, 23.7%).

General Procedure 18

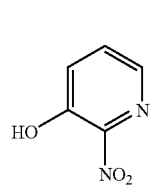 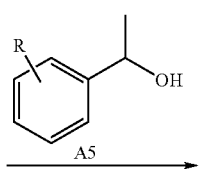 →

-continued

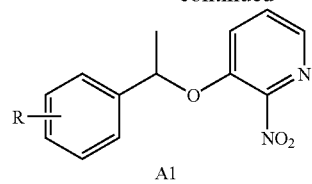

A1

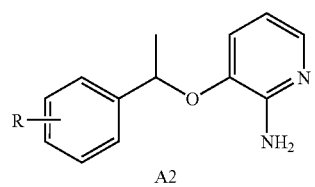

A2

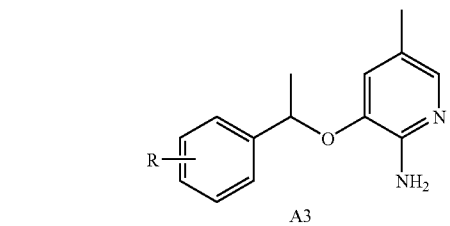

A3

Sodium borohydride (1.5 molar equivalent) is added to solution of ketone (3.89 mmol) in 10 mL of ethanol under a nitrogen atmosphere. The resulting mixture is stirred at room temperature for 12 hr. The mixture is then put in an ice bath and quenched with dilute aqueous HCl. The ethanol is evaporated and EtOAc is added to extract the aqueous solution. The EtOAc layer is dried over Na$_2$SO$_4$. The Na$_2$SO$_4$ is filtered off and the filtrate evaporated to give a oil residue, compound A5. The residue is used without further purification.

3-Hydroxy-2-nitropyridine (1.1 molar equivalent) and triphenylphosphine (1.5 molar equivalent) are added to a solution of compound A5 (1.1 mmol) in 10 mL of THF. The reaction mixture is then put in an ice bath and diisopropyl azodicarboxylate (1.5 molar equivalent) is added. The ice bath is removed and the mixture stirred at room temperature for 12 hr. The solvent is evaporated to give a yellow oil residue. The residue is purified by silica gel chromatography (eluting EtOAc in hexanes) to give compound A1.

2 M HCl (0.2 mL) is added to solution of compound A1 (0.97 mmol) in 2 mL of ethanol. The mixture is then put in an ice bath and Fe powder (365 mg) is added slowly. The reaction is heated to 85° C. for 1 hr and cooled to room temperature. Celite (0.5 g) is added to stir and the resulting mixture is filtered through a bed of celite and rinsed with ethanol. The filtrated is evaporated to give a brown oil residue, compound A2. The residue is used without further purification.

Periodic acid (0.25 molar equivalent), iodine (0.5 molar equivalent), H$_2$O (0.5 mL), and concentrate sulfuric acid (0.03 mL) are added to a solution of compound A2 in 3 mL of acetic acid. The reaction mixture is heated to 85° C. for 5 hr. The reaction mixture is then cooled in an ice bath and basified with saturated aq. Na$_2$CO$_3$ to a pH of 3-4. Ethyl acetate is added to extract the aqueous solution. Dry EtOAc layer over Na$_2$SO$_4$. The Na$_2$SO$_4$ is filtered off and the filtrated evaporated to give a brown oil residue. The residue is purified by silica gel chromatography (eluting with EtOAc and hexanes) to give desired product, compound A3.

General Procedure 19

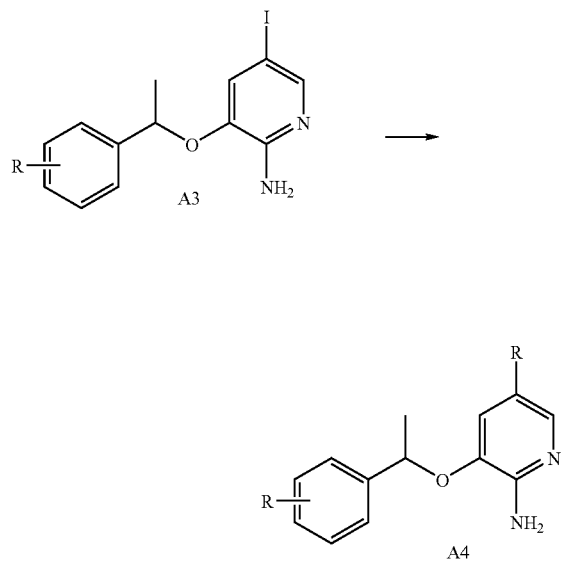

Boronic ester or boronic acid (1.3 molar equivalent) is added to a solution of compound A3 (0.47 mmol) in 5 mL of DME. The mixture was purged with nitrogen several times and then dichlorobis(triphenylphosphino) palladium (II) (0.05 molar equivalent) is added. Sodium carbonate (3 molar equivalent) in 1 mL of H₂O is added to the reaction mixture and the resulting solution heated to 85° C. for 12 hr. Water is added to the reaction mixture to quench the reaction. EtOAc is then added to extract the aqueous solution. Dry EtOAc layer over Na₂SO₄. The Na₂SO₄ is filtered off and the filtrated evaporated to give a dark brown oil residue. The residue is purified by silica gel chromatography (eluting with CH₃OH, CH₂Cl₂, EtOAc, and hexanes) to give desired product, compound A4.

General Procedure 20

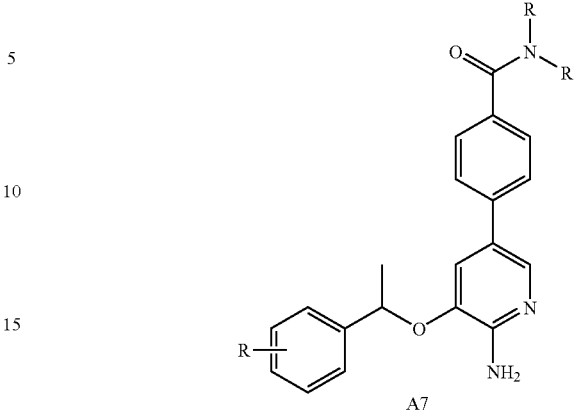

Compound A6 was prepared using general procedure 19. O-(7-azabenzotriazol-1-yl)-N,N,N',N'-tetramethyluronium phosphorus pentafluoride (HATU) (1.1 molar equivalent), diisopropylethyl amine (5 molar equivalent) and amine (1.3 molar equivalent) are added to a solution of compound A6 (0.17 mmol) in 3 mL of DMF under a nitrogen atmosphere. The reaction is allowed to stir at room temperature for 12 hr. Saturated NaHCO₃ is added to the reaction mixture to quench the reaction. EtOAc is then added to extract the aqueous solution. Dry EtOAc layer over Na₂SO₄. The Na₂SO₄ is filtered off and the filtrate is evaporated to give a brown oil residue. The residue is purified by silica gel chromatography (eluting with EtOAc and hexanes) to give desired amide product, compound A7, as a yellow oil.

General Procedure 21

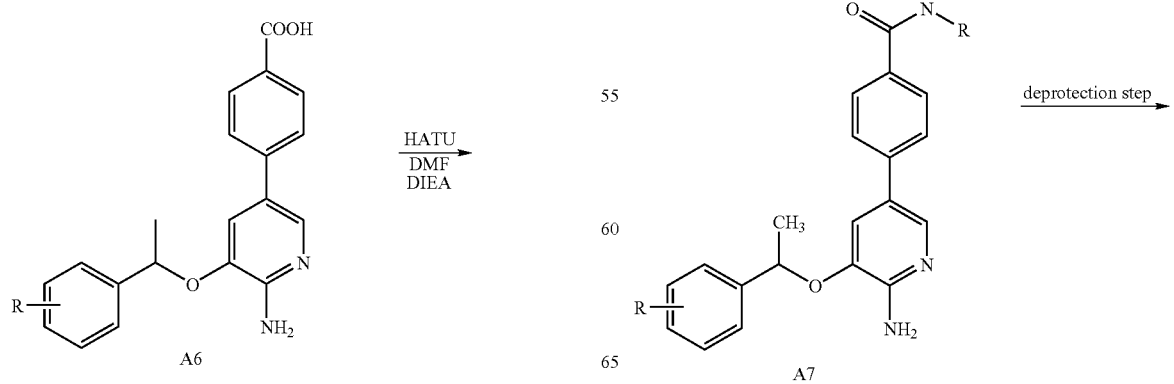

-continued

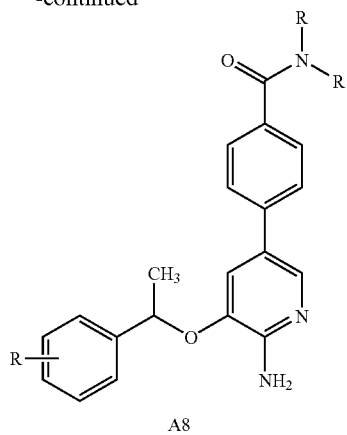

A8

Acid (16 molar equivalent or less) is added to compound A7 (0.13 mmol) at room temperature. The resulting solution is stirred at room temperature or heated to 60° C. for 12 hr. The reaction mixture is evaporated and the residue is purified by silica gel chromatography (eluting with $CH_3OH$, EtOAc and $CH_2Cl_2$) to give desired amide product, compound A8, as a yellowish to white solid.

General Procedure 22

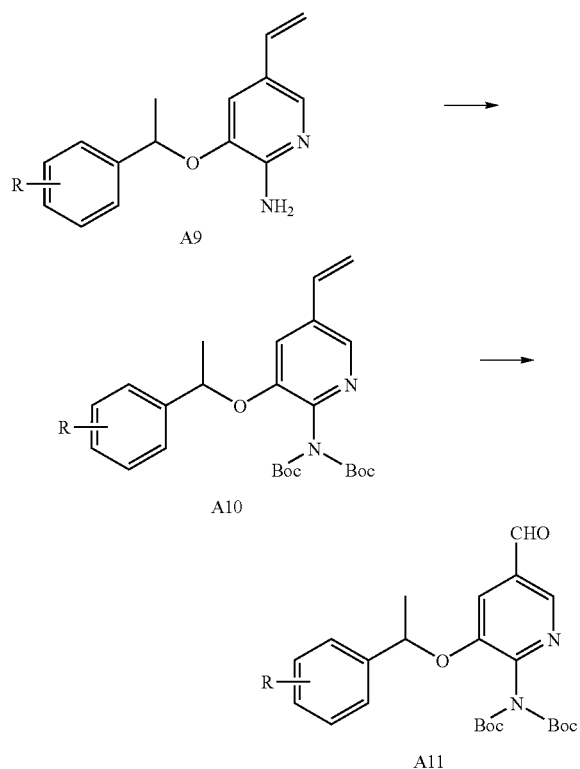

Compound A9 is prepared using general procedure 19. Di-tert-butyl dicarbonate (3 molar equivalent) and 4-(dimethylamino)pyridine (0.14 molar equivalent) are added to a solution of compound A9 (3 mmol) in 20 mL of DMF. The reaction mixture is stirred at room temperature for 12 hr. Water is added to the reaction mixture to quench the reaction. EtOAc is then added to extract the aqueous solution. Dry EtOAc layer over $Na_2SO_4$. The $Na_2SO_4$ is filtered off and the filtrated evaporated to give a brown yellow oil residue. The residue is purified by silica gel chromatography (eluting with 25→30% EtOAc in hexanes) to give desired product, compound A10 as a yellowish oil (87.8% yield). Ozone is bubbled through a solution of compound A10 in 50 mL of $CH_2Cl_2$ at −78° C. and dimethyl sulfide is added to quench the reaction. Saturated sodium chloride is added to the reaction mixture and EtOAc is added to extract the aqueous solution. Combined EtOAc layer is dried over $Na_2SO_4$. The $Na_2SO_4$ is filtered off and the filtrated is evaporated to give a yellow oil residue. The residue is purified by silica gel chromatography (eluting with 35→40% EtOAc in hexanes) to give desired product, compound A11 as a yellowish oil (58.4% yield).

General Procedure 23: Reductive Amination

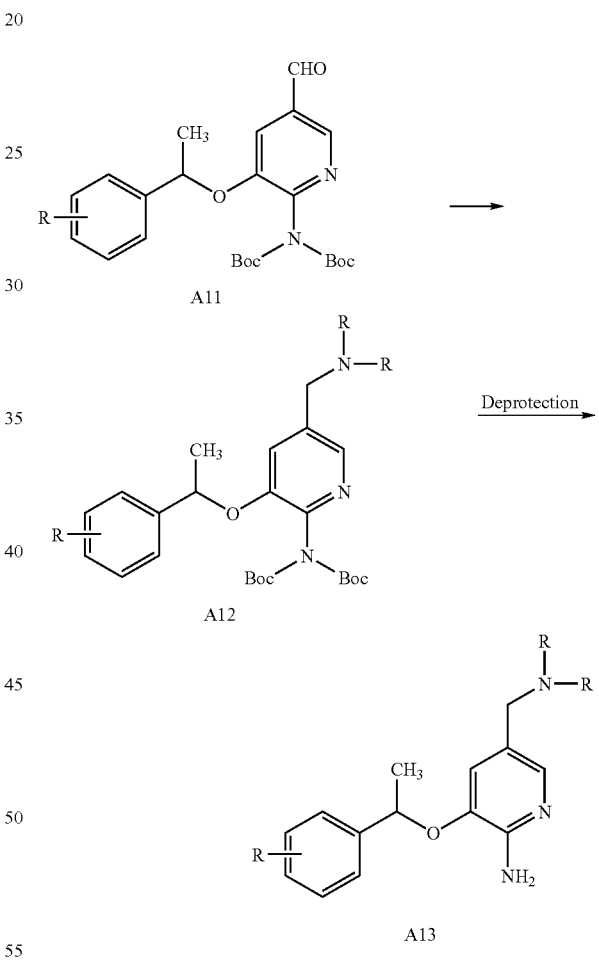

Amine hydrochloride salt (1.2 molar equivalent), sodium acetate (2 molar equivalent to the amine hydrochloride salt) are added to a solution of compound A11 (0.45 mmol) in 4 mL of $CH_3OH$ under a nitrogen atmosphere. Molecular sieve (0.5 g) is added to the reaction mixture and then sodium cyanoborohydride (2 molar equivalent) is added. The resulting mixture is stirred at room temperature for 12 hr under a nitrogen atmosphere. The reaction mixture is filtered through a bed of celite and the filtrate is evaporated and purified by silica gel chromatography (eluting $CH_3OH$, EtOAc, and $CH_2Cl_2$) to give desired product, compound A12 as an oil (52.6% yield). Acid (16 molar equivalent or less) is added to compound A12 (0.17 mmol) at room temperature. The resulting solution is stirred at room temperature or heated to 60° C. for 12 hr. The reaction mixture is evaporated and the residue was purified by silica gel chromatography (eluting with CH₃OH, EtOAc and CH₂Cl₂) to give desired product, compound A13.

General Procedure 24

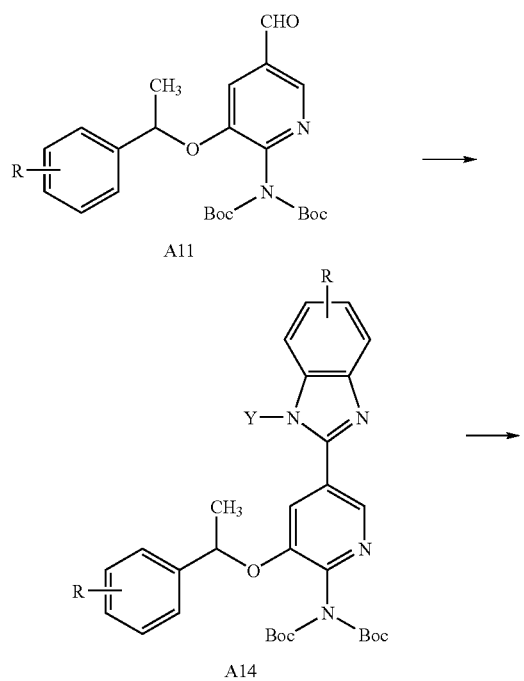

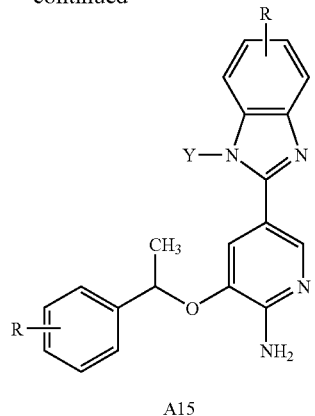

O-phenyldiamines (1.2 molar equivalent) and sodium bisulfite (2.1 molar equivalent) are added to a solution of compound A11 (0.41 mmol) in 5 mL of DMA. The resulting solution is heated to 110° C. for 12 hr. Water is added to the reaction mixture to quench the reaction. EtOAc is then added to extract the aqueous solution. Dry EtOAc layer over Na₂SO₄. The Na₂SO₄ is filtered off and the filtrated is evaporated to give a brown yellow oil residue. The residue is purified by silica gel chromatography (eluting with EtOAc in hexanes) to give desired product, compound A14. Acid (16 molar equivalent or less) is added to compound A14 (0.16 mmol) at room temperature. The resulting solution is stirred at room temperature or heated to 60° C. for 12 hr. The reaction mixture is evaporated and the residue is purified by silica gel chromatography (eluting with CH₃OH, EtOAc and CH₂Cl₂) to give desired amide product, compound A15.

General Procedure 25

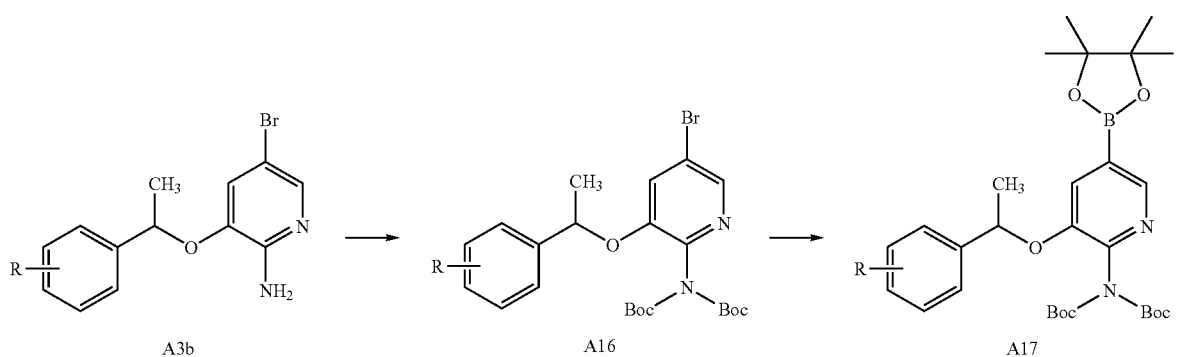

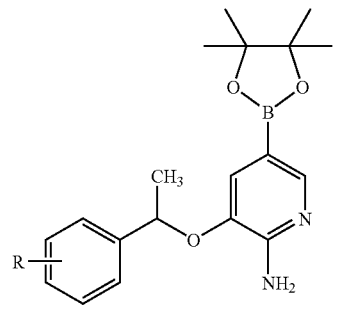

A18

Di-tert-butyl dicarbonate (3 molar equivalent), 4-(dimethylamino)pyridine (0.14 molar equivalent) are added to a solution of compound A3b (2 mmol) in 10 mL of DMF. The reaction mixture is stirred at room temperature for 12 hr. Water is added to the reaction mixture to quench the reaction. EtOAc is then added to extract the aqueous solution. Dry EtOAc layer over Na$_2$SO$_4$. The Na$_2$SO$_4$ is filtered off and the filtrated is evaporated to give a brown yellow oil residue (compound a16). The residue is used without further purification.

Bis(pinacolato)diboron (1.2 molar equivalent) and potassium acetate (3.4 molar equivalent) are added to a solution of compound a16 in 4 mL of DMSO. The mixture is purged with nitrogen several times and then dichlorobis(triphenylphosphino) palladium (II) (0.05 molar equivalent) is added. The resulting solution is heated to 80° C. for 12 hr. Water is added to the reaction mixture to quench the reaction. EtOAc is then added to extract the aqueous solution. Dry EtOAc layer over Na$_2$SO$_4$. The Na$_2$SO$_4$ is filtered off and the filtrated is evaporated to give a dark brown oil residue. The residue is purified by silica gel chromatography (eluting with 30% EtOAc in hexanes) to give desired product, compound A17 (76% yield). HCl (5 molar equivalent) is added to a solution of compound A17 (0.43 mmol) in 4 mL of CH$_2$Cl$_2$. The resulting mixture is heated to 50° C. for 12 hr. Saturated NaHCO$_3$ is added to the reaction mixture to neutralize the reaction. EtOAc is then added to extract the aqueous solution. Dry EtOAc layer over Na$_2$SO$_4$. The Na$_2$SO$_4$ is filtered off and the filtrated is evaporated to give the desired product (compound A18) as a yellow solid (75% yield).

General Procedure 26

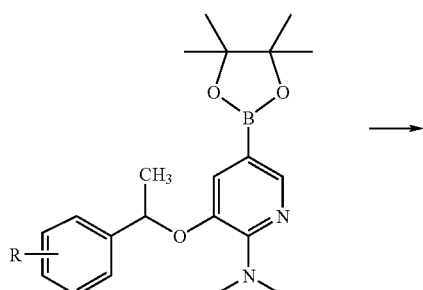

A17

-continued

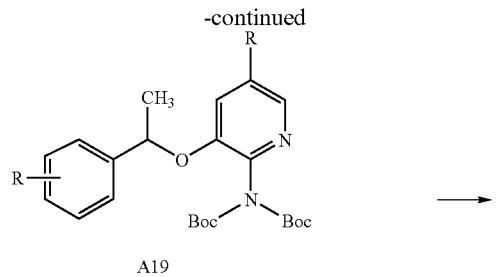

A19

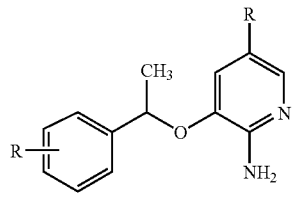

A20

Compound A17 (1.3 molar equivalent) is added to a solution of aryl halide (0.36 mmol) in 3 mL of DME. The mixture is purged with nitrogen several times and then dichlorobis(triphenylphosphino) palladium (II) (0.05 molar equivalent) is added. Sodium carbonate (3 molar equivalent) in 0.8 mL of H$_2$O is added to the reaction mixture and the resulting solution is heated to 85° C. for 12 hr. Water is added to the reaction mixture to quench the reaction. EtOAc is then added to extract the aqueous solution. Dry EtOAc layer over Na$_2$SO$_4$. The Na$_2$SO$_4$ is filtered off and the filtrated is evaporated to give a dark brown oil residue. The residue is purified by silica gel chromatography (eluting with EtOAc in hexanes) to give desired product, compound A19 (74.4% yield). HCl (5 molar equivalent) is added to a solution of compound A19 (0.26 mmol) in 10 mL of isopropyl alcohol. The resulting mixture is heated to 50° C. for 12 hr. The solvent is evaporated to give the desired product, compound A20.

General Procedure 27

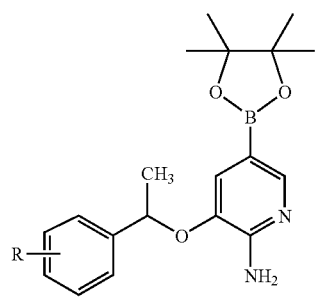

A18

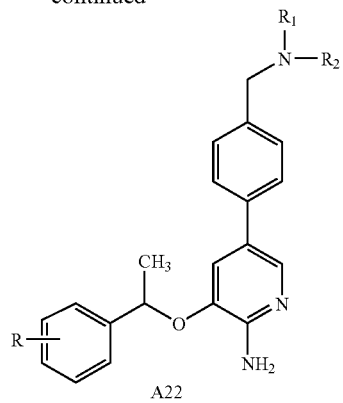

A22

Compound A18 (1.3 molar equivalent) is added to a solution of aryl halide (0.21 mmol) in 3 mL of DME. The mixture is purged with nitrogen several times and then dichlorobis (triphenylphosphino) palladium (II) (0.05 molar equivalent) is added. Sodium carbonate (3 molar equivalent) in 0.6 mL of $H_2O$ is added to the reaction mixture and the resulting solution is heated to 85° C. for 12 hr. Water is added to the reaction mixture to quench the reaction. EtOAc is then added to extract the aqueous solution. Dry EtOAc layer over $Na_2SO_4$. The $Na_2SO_4$ is filtered off and the filtrated is evaporated to give a dark brown oil residue. The residue is purified by silica gel chromatography (eluting with $CH_3OH$, $CH_2Cl_2$, EtOAc, and hexanes) to give desired product, compound A21.

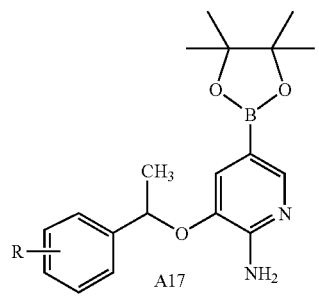

A21

General Procedure 28

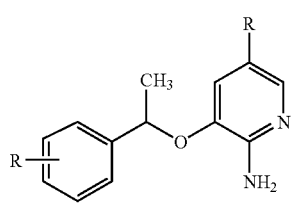

A17    A23

X = I, Br, Cl

Amine (1.5 molar equivalent) and $K_2CO_3$ (1.5 molar equivalent) are added to a solution of 4-halobenzyl halide (1.0 molar equivalent) in 2 mL of toluene. The resulting mixture is microwaved using Smithsynthesizer (150° C., 1 hr). Water is added to the reaction mixture to quench the reaction. EtOAc is then added to extract the aqueous solution. Dry EtOAc layer over $Na_2SO_4$. The $Na_2SO_4$ is filtered off and the filtrated is evaporated to give the desired product, compound A23. The residue is used in procedure 11 without further purification to synthesize compound A22.

General Procedure 29

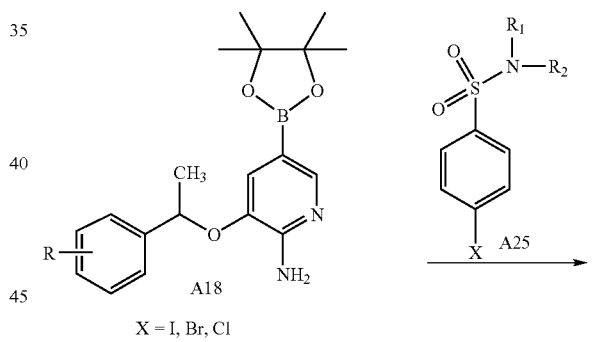

A18       A25

X = I, Br, Cl

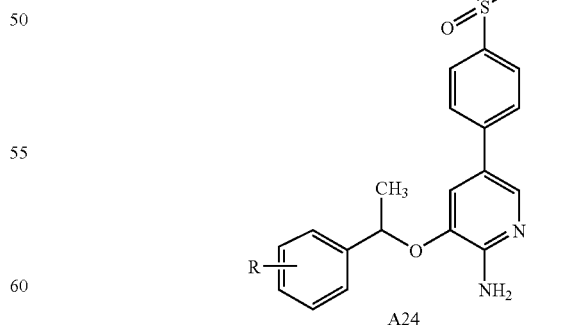

A24

Amine (1.2 molar equivalent) and diisopropylamine (5 molar equivalent) are added to a solution of 4-bromobenzenesulfonyl chloride (0.77 mmol) in 5 mL of $CHCl_3$ under a nitrogen atmosphere. The resulting mixture is stirred at room temperature for 4 hr. Water is added to the reaction mixture to quench the reaction. EtOAc is then added to extract the aqueous solution. Dry EtOAc layer over Na₂SO₄. The Na₂SO₄ is filtered off and the filtrated is evaporated to give the desired product, compound A25. The residue is used in procedure 11 without further purification to synthesize compound A24.

General Procedure 30

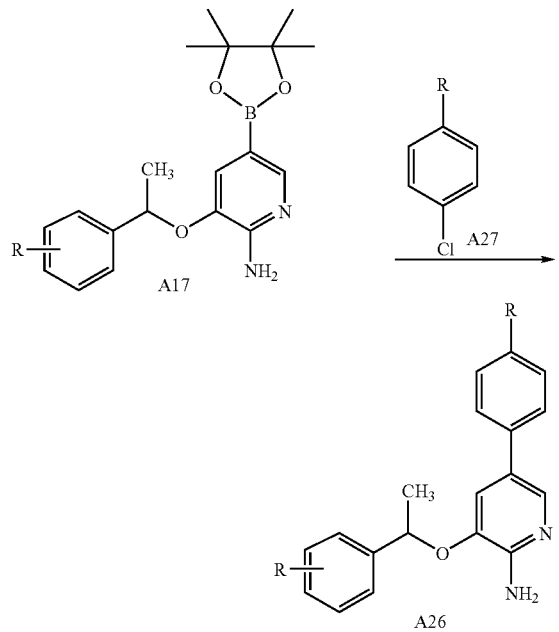

Boronic ester or boronic acid (1.2 molar equivalent) is added to a solution of 1-chloro-4-iodobenzene (0.84 mmol) in 10 mL of (DME) under a nitrogen atmosphere. The mixture is purged with nitrogen several times and then dichlorobis(triphenylphosphino) palladium (II) (0.05 molar equivalent) is added. Sodium carbonate (3 molar equivalent) in 1.8 mL of H₂O is added to the reaction mixture and the resulting solution is heated to 85° C. for 12 hr. Water is added to the reaction mixture to quench the reaction. EtOAc is then added to extract the aqueous solution. Dry EtOAc layer over Na₂SO₄. The Na₂SO₄ is filtered off and the filtrated is evaporated to give a dark brown oil residue. The residue is purified by silica gel chromatography (eluting with CH₃OH, CH₂Cl₂, EtOAc, and hexanes) to give desired product, compound A27. Compound A27 is used in procedure 11 to synthesize compound A26.

General Procedure 31 for Chiral Separation of Racemates

The racemic sample is purified using preparative supercritical fluid chromatography SFC-MS. Exemplary purification conditions: column-Chiralpak AD-H, 250×21 mm, 5 micron, 100A column (Column #:ADH0CJ-C1003); column temperature 35° C.; mobile phase 35% methanol (with 0.1% isopropylamine)-modified CO₂; preparative flow rate 52 mL/min; isobaric pressure at 120 bar.

General Procedure 32: Using (4-{6-Amino-5-[1-(3-trifluoromethyl-phenyl)-ethoxy]-pyridin-3-yl}-phenyl)-(3,5-dimethyl-piperazin-1-yl)-methanone

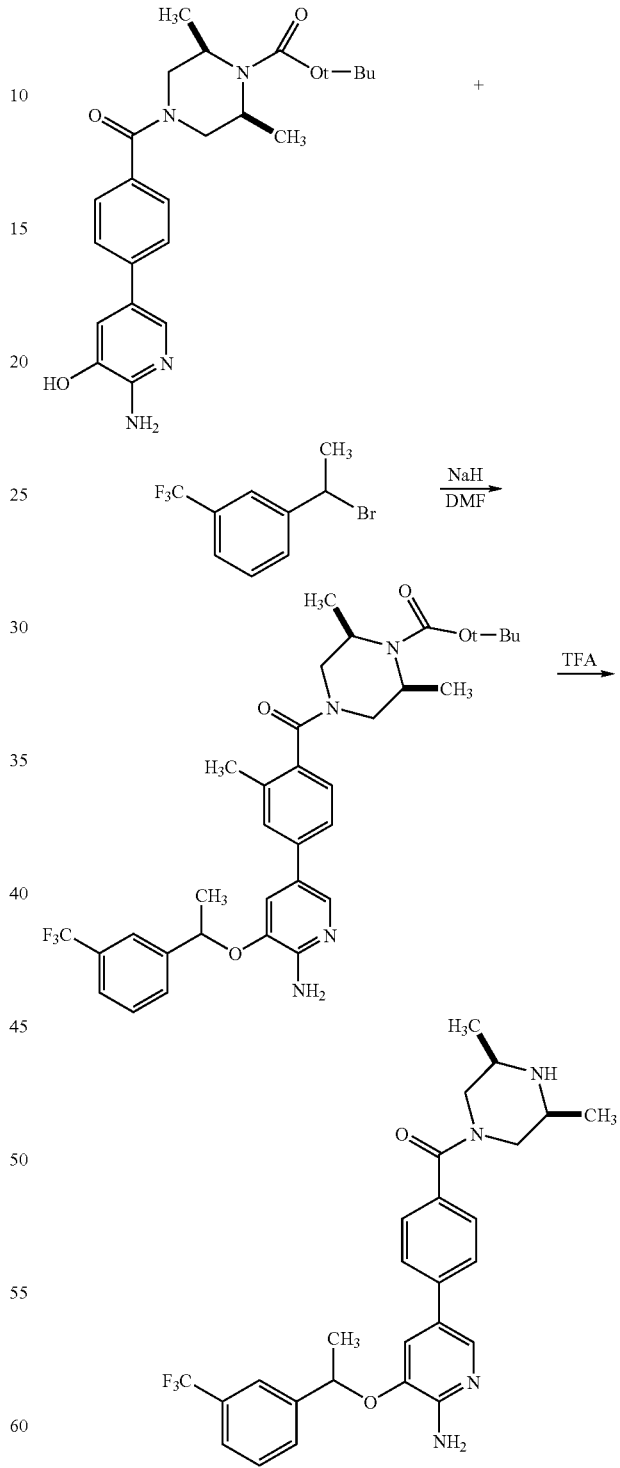

To a mixture of 4-[4-(6-Amino-5-hydroxy-pyridin-3-yl)-benzoyl]-2,6-dimethyl-piperazine-1-carboxylic acid tert-butyl ester (100 mg, 0.23 mmol) and 1-(1-bromo-ethyl)-3-trifluoromethyl-benzene (64 mg, 0.25 mmol) in DMF (2 ml) was added NaH (12 mg, 0.47 mmol) at 0° C. The mixture was stirred overnight. LCMS showed that the reaction was completed, DMF and water were removed. TFA (2 mL) was added to the residue and stirred at room temperature for 3 hr. TFA was removed followed by addition of methanol. The residue was purified by prep-HPLC to afford (4-{6-Amino-5-[1-(3-trifluoromethyl-phenyl)-ethoxy]-pyridin-3-yl}-phenyl)-(3,5-dimethyl-piperazin-1-yl)-methanone (30 mg, yield 25.7%).

General Procedure 33: Using (4-{6-amino-5-[1-(2-trifluoromethyl-phenyl)-ethoxy]-pyridin-3-yl}-phenyl)-(3,5-dimethyl-piperazin-1-yl)-methanone

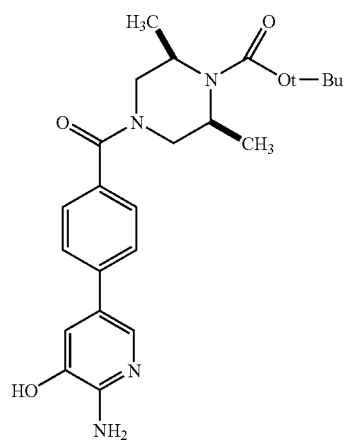

+

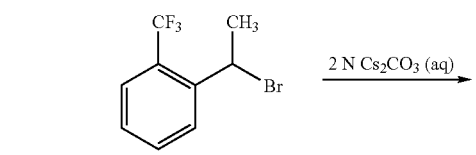

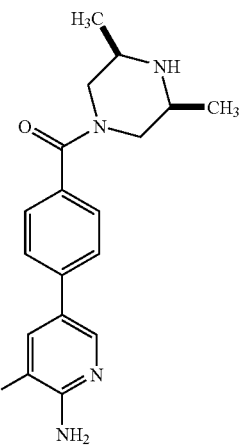

To a mixture of 4-[4-(6-Amino-5-hydroxy-pyridin-3-yl)-benzoyl]-2,6-dimethyl-piperazine-1-carboxylic acid tert-butyl ester (50 mg, 0.12 mmol) and 1-(1-bromo-ethyl)-2-trifluoromethyl-benzene (32 mg, 0.12 mmol) in DMF (2 ml) was added 2 M Cs$_2$CO$_3$ (0.18 mL, 0.35 mmol), followed by water (0.5 mL), the mixture was stirred overnight then heated at 70° C. for 8 hr, LCMS showed that the reaction was completed. The DMF and water were removed. TFA (2 mL was added to the residue and stirred at room temperature for 3 hr. The TFA was removed, followed by addition of methanol. The residue was purified by prep-HPLC to afford (4-{6-amino-5-[1-(2-trifluoromethyl-phenyl)-ethoxy]-pyridin-3-yl}-phenyl)-(3,5-dimethyl-piperazin-1-yl)-methanone (20 mg, yield 34.2%).

General Procedure 34: Using {4-[6-Amino-5-(2-methyl-benzyloxy)-pyridin-3-yl]-phenyl}-(3,5-dimethyl-piperazin-1-yl)-methanone

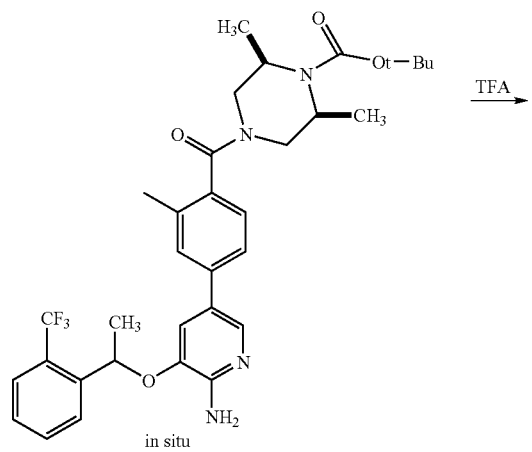

-continued

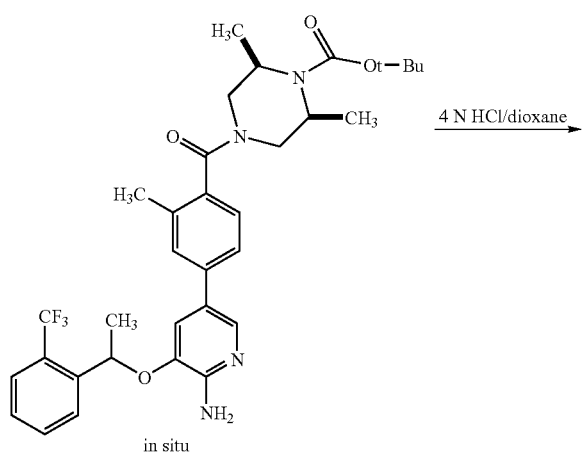

in situ

↓ 4 N HCl/dioxane

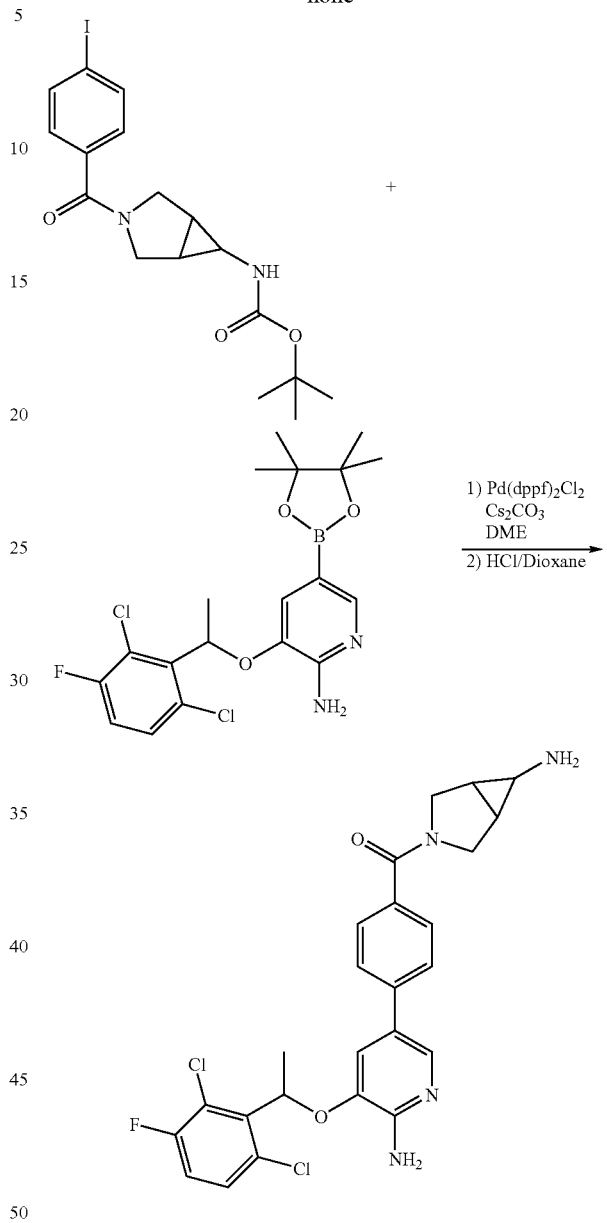

General Procedure 35: Using (6-amino-3-aza-bicyclo [3.1.0]hex-3-yl)-(4-{6-amino-5-[1-(2,6-dichloro-3-fluoro-phenyl)-ethoxy]-pyridin-3-yl}-phenyl)-methanone To a mixture of (2R,6S)-4-[4-(6-Amino-5-hydroxy-pyridin-3-yl)-benzoyl]-2,6-dimethyl-piperazine-1-carboxylic acid tert-butyl ester (100 mg, 0.23 mmol) and 1-bromomethyl-2-methyl-benzene (47 mg, 0.25 mmol) in DMF (2 mL) was added 2 M Cs$_2$CO$_3$ (0.35 mL, 0.7 mmol) followed by water (0.5 mL). The mixture was stirred at room temperature overnight. LCMS showed the reaction was completed, DMF was removed, followed by addition of 4 N HCl in dioxane (2 mL) and the reaction was stirred at room temperature for 3 hr. The volatiles were removed followed by addition of methanol. This solution was purified by prep-HPLC to afford {4-[6-Amino-5-(2-methyl-benzyloxy)-pyridin-3-yl]-phenyl}-(3,5-dimethyl-piperazin-1-yl)-methanone (47 mg, yield 46.6%).

To a mixture of [3-(4-iodo-benzoyl)-3-aza-bicyclo[3.1.0] hex-6-yl]-carbamic acid tert-butyl ester (100 mg, 0.234 mmol) and 3-[1-(2,6-dichloro-3-fluoro-phenyl)-ethoxy]-5-(4,4,5,5-tetramethyl-[1,3,2]dioxaborolan-2-yl)-pyridin-2-ylamine (100 mg, 0.234 mmol) in DME (2 mL) was added Pd(dppf)$_2$Cl$_2$·CH$_2$Cl$_2$ (10 mg, 0.012 mmol) and Cs$_2$CO$_3$ (351 mg, 0.702 mmol). The mixture was bubbled with nitrogen for 10 min then microwaved at 150° C. for 30 min. LCMS checked that the reaction was completed. The crude reaction mixture was diluted with ethyl acetate followed by washings with water and brine. The solution was dried over MgSO$_4$. Purification by prep-HPLC afforded a solid. The solid was stirred with 4 N HCl/dioxane (3 mL) for 3 hr at room temperature. Removal of the volatiles led to a residue that was purified by prep-HPLC to afford (6-amino-3-aza-bicyclo

[3.1.0]hex-3-yl)-(4-{6-amino-5-[1-(2,6-dichloro-3-fluoro-phenyl)-ethoxy]-pyridin-3-yl}-phenyl)-methanone (30 mg, yield 26%).

General Procedure 36: Using 5-[1-(2,6-Dichloro-3-fluoro-phenyl)-ethoxy]-6'-(2-morpholin-4-yl-ethoxy)-[3,3']bipyridinyl-6-ylamine

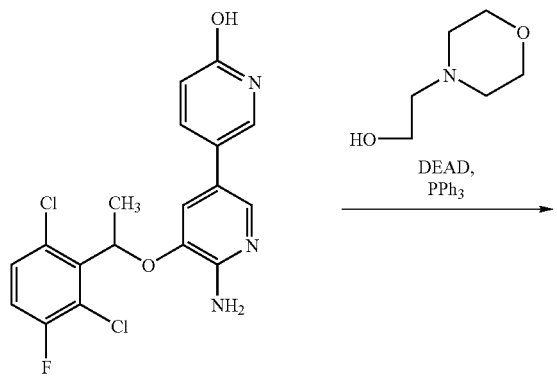

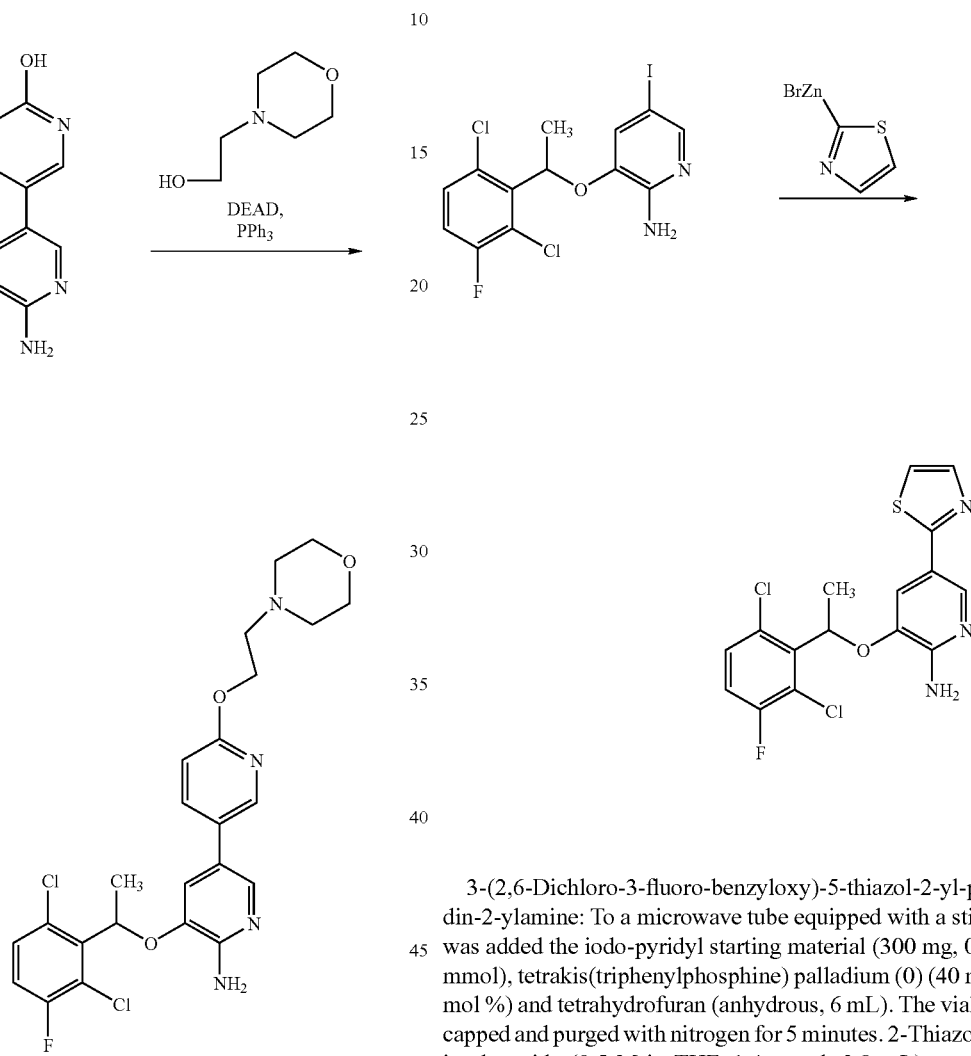

To a mixture of 6'-amino-5'-[1-(2,6-dichloro-3-fluoro-phenyl)-ethoxy]-[3,3']bipyridinyl-6-ol (78 mg, 0.20 mmol), triphenylphosphine (63 mg, 0.24 mmol) and 2-morpholin-4-yl-ethanol (0.026 mL, 0.22 mmol) was added DEAD (0.034 mL, 0.22 mmol). After stirring overnight more PPh$_3$ (63 mg, 0.24 mmol) and more DEAD (0.034 mL, 0.22 mmol) were added. After several hours, more alcohol (0.026 mL, 0.22 mmol) was added. After several more hours, more PPh$_3$ (63 mg, 0.24 mmol) and more DEAD (0.034 mL, 0.22 mmol) were added. After stirring overnight, the mixture was partitioned between dichloromethane and half-saturated brine. The phases were separated and the aqueous phase was extracted with dichloromethane. The combined organic phases were dried over Na$_2$SO$_4$ and concentrated by rotary evaporation. The residue was purified by silica gel chromatography using gradient elution of dichloromethane, metha-nol to afford 5-[1-(2,6-Dichloro-3-fluoro-phenyl)-ethoxy]-6'-(2-morpholin-4-yl-ethoxy)-[3,3']bipyridinyl-6-ylamine (53 mg, 53%).

General Procedure 37: Using Example I-650 of U.S. patent application Ser. No. 10/786,610 (PCT/US2004/005495)

3-(2,6-Dichloro-3-fluoro-benzyloxy)-5-thiazol-2-yl-pyridin-2-ylamine: To a microwave tube equipped with a stir bar was added the iodo-pyridyl starting material (300 mg, 0.702 mmol), tetrakis(triphenylphosphine) palladium (0) (40 mg, 5 mol %) and tetrahydrofuran (anhydrous, 6 mL). The vial was capped and purged with nitrogen for 5 minutes. 2-Thiazolylzinc bromide (0.5 M in THF, 1.4 mmol, 2.8 mL) was then added via syringe. The vial was heated to 120° C. in the microwave for 10 minutes. TLC (1:1 ethyl acetetate:methylene chloride) showed a large amount of starting material remaining. Additional 2-thiazolylzinc bromide (0.5 M in THF, 500 µL) was added and the vial was heated to 120° C. in the microwave for 20 minutes. TLC (1:1 ethyl actetate:methylene chloride) showed a large amount of starting material still remaining. Additional 2-thiazolylzinc bromide (0.5 M in THF, 500 µL) was added and the vial was heated to 120° C. in the microwave for 60 minutes. TLC (1:1 ethyl actetate:methylene chloride) still showed a large amount of starting material still remaining but also had become very messy. The vial contents were poured into a sat. NH$_4$Cl solution (10 mL) and this solution extracted with ethyl acetate (2×30 mL). The combined ethyl acetate layers were dried over Na$_2$SO$_4$, filtered and concentrated in vacuo. The crude product was loaded onto a 10 g prepacked silica gel column and 1:1 ethyl acetate:methylene chloride used to elute the desired product. (40 mg, 15%).

General Procedure 38: Using Example I-652 of U.S. patent application Ser. No. 10/786,610 (PCT/US2004/005495)

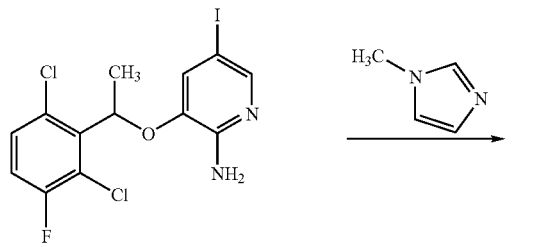

3-[1-(2,6-Dichloro-3-fluoro-phenyl)-ethoxy]-5-(1-methyl-1H-imidazol-2-yl)-pyridin-2-ylamine: N-methyl imidazole (92 mg, 1.1 mmol) was dissolved in tetrahydrofuran (anhydrous, 4 mL) in a 50 mL round bottom flask. The flask was cooled with a dry-ice/acetone bath under nitrogen atmosphere. N-butyl lithium (2.5 M, 562 μL, 1.4 mmol) was added via syringe in 100 μL portions over 5 minutes. The reaction was stirred at −70° C. for 30 minutes. Solid zinc chloride (anhydrous, 383 mg, 2.8 mmol) was added and the reaction stirred for 15 minutes. The ice bath was then removed and the reaction allowed to warm to room temperature. Once all of the zinc chloride was in solution and the reaction at room temperature, iodo scaffold (400 mg, 0.936 mmol) was added in tetrahydrofuran (anhydrous, 4 mL), followed by tetrakis (triphenylphosphine) palladium (0) (108 mg, 10 mol %) and the reaction heated to reflux. The reaction was monitored by LC/MS until all of the starting iodo scaffold was consumed. The reaction was allowed to cool and then diluted with a sat. NH$_4$Cl solution (20 mL). This solution was extracted with ethyl acetate (2×50 mL). The combined ethyl acetate layers were dried over Na$_2$SO$_4$, filtered and concentrated in vacuo. The crude product was loaded onto a 10 g prepacked silica gel column and 10% methanol:ethyl acetate was used to elute the desired product (25 mg, 7%).

General Procedure 39: Using Example I-657 of U.S. patent application Ser. No. 10/786,610 (PCT/US2004/005495)

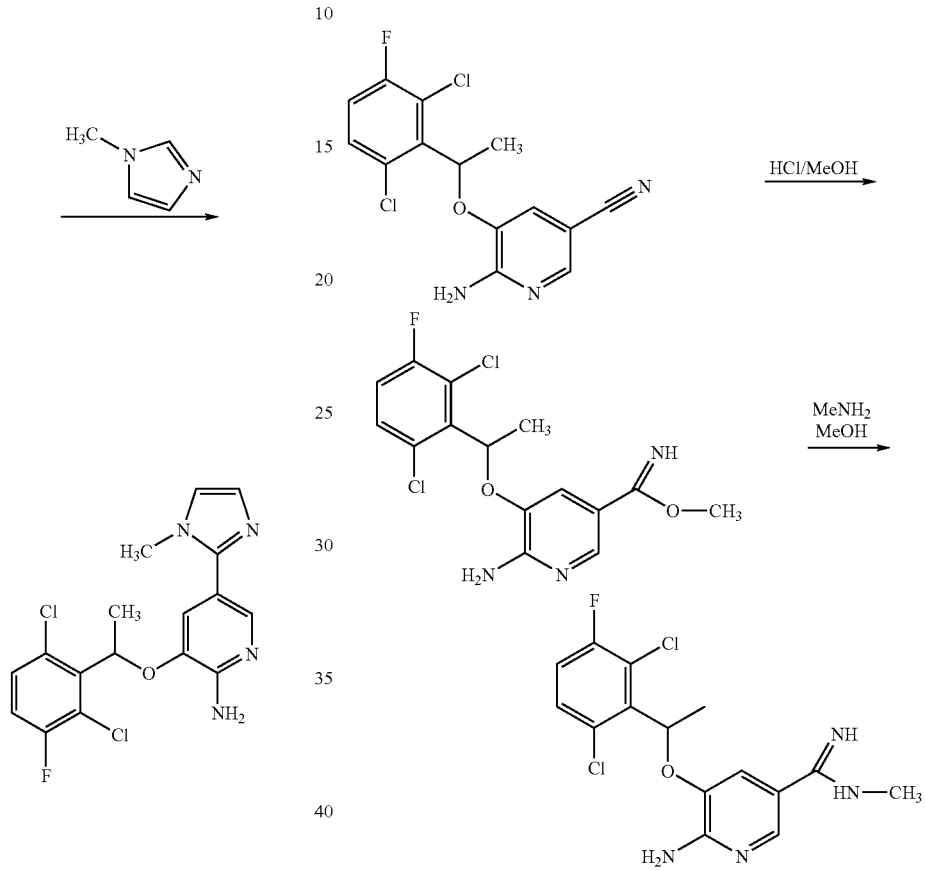

To 6-Amino-5-[1-(2,6-dichloro-3-fluoro-phenyl)-ethoxy]-nicotinonitrile (400 mg, 1.23 mmol) in 70 mL dry methanol at 0° C. was bubbled HCl gas for 3 minutes. Stirred overnight at 3° C. Removed volatiles and washed the solids with diethyl ether to yield quantitatively the imidate. To 200 mg of the imidate in 4 mL methanol at 0° C. was added 2N methylamine in THF (837 μL). Let stir at 0° C. for about 1 hr then let warm to rt overnight. The volatiles were removed and the residue was chromatographed with 10-20% methanol/dichloromethane to yield 70 mg of product.

General Procedure 40

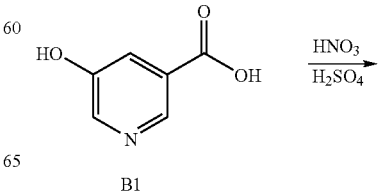

B1

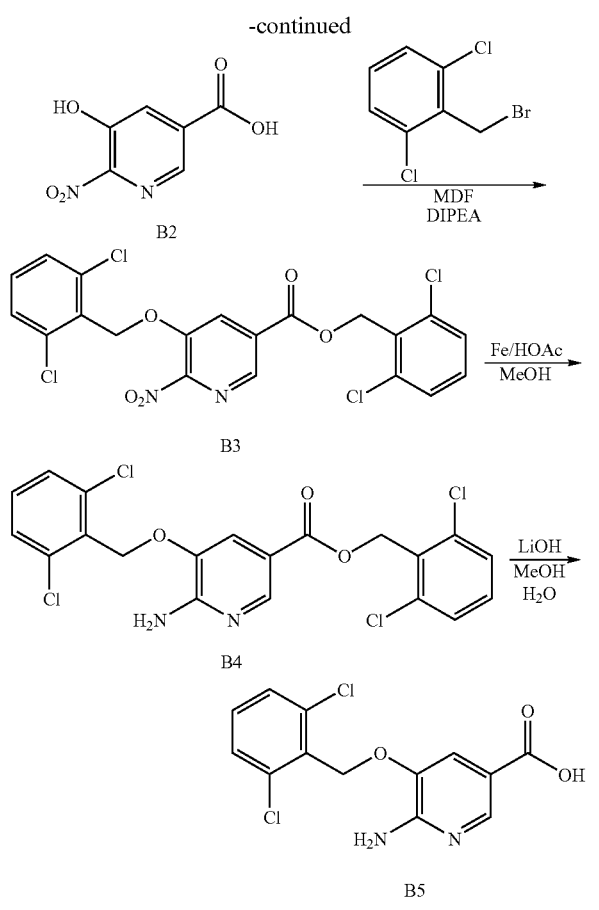

and ammonium hydroxide (30%) was added to neutralize the mixture. Minimum amount of DMF was added to dissolve the reaction mixture, which was purified by flash column chromatograph (eluent: EtOAc-EtOH, 9:1) to give 4.5 g (87%) of B4 as a pale yellow solid. MS (APCI) (M+H)$^+$ 473.

4. 6-Amino-5-[(2,6-dichlorobenzyl)oxy]nicotinic acid (B5): A mixture of 2,6-dichlorobenzyl-6-amino-5-[(2,6-dichlorobenzyl)oxy]nicotinate (B4) (3.5 g, 7.4 mmol), lithium hydroxide (0.41 g, 17 mmol), water (22 mL) and methanol (30 mL) was stirred and reflux at 85° C. for 5 hr. The mixture was concentrated to dryness under reduced pressure. The resulting residue was dissolved in water, extracted with a mixture of Et$_2$O/hexane (1:1, 4×25 mL), neutralized with 1N HCl to form white precipitation, which was filtered and dried under reduced pressure to provide 1.83 grams (79%) of B5 as a white solid. MS (APCI) (M+H)$^+$ 313. $^1$HNMR (DMSO-d$_6$) δ 5.26 (s, 2H, ArCH$_2$O), 6.37 (s, 2H, NH$_2$), 7.43-7.48 (t, 1H, Ar—H), 7.54 (s, 2H, Ar—H), 7.56 (s, 1H, Ar—H), 8.18 (s, 1H, Ar—H).

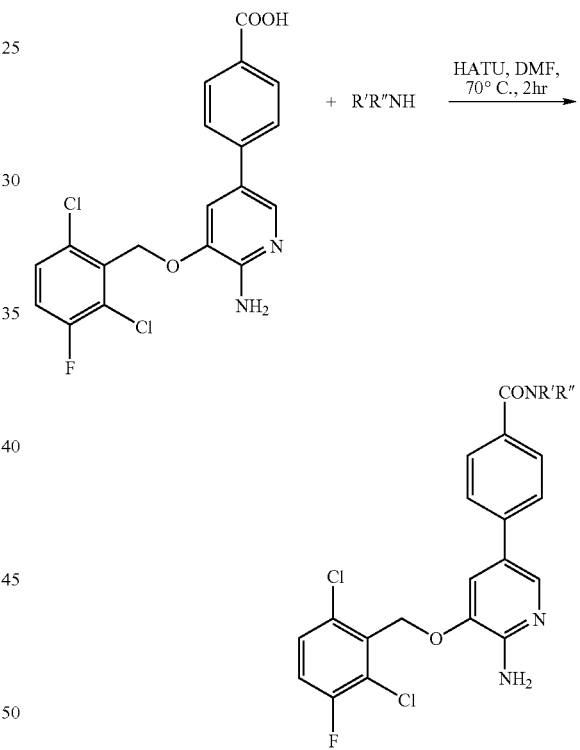

1. 6-Nitro-5-hydroxynicotinic acid (B2): To a solution of 5-hydroxynicotinic acid (B1) (7.0 g, 50 mmol) in concentrated H$_2$SO$_4$ was added 9 mL of fuming HNO$_3$ (90%) (9 mL). The reaction mixture was stirred at 55-60° C. in a sealed tube for four days. The mixture was then poured into ice and the pH was adjusted to 3 with 50% NaOH. MgSO$_4$ was added to saturate the aqueous mixture, which was then extracted with isopropyl alcohol (4×45 mL). After the removal of isopropyl alcohol under reduced pressure, 5.93 g (64% yield) of B2 was obtained as a yellow solid. MS (APCI), (M+H)$^+$ 185. $^1$HNMR (DMSO-d$_6$) δ 8.01 (d, 1H, Ar—H), 8.41 (d, 1H, Ar—H).

2. 2,6-Dichlorobenzyl-6-nitro-5-[(2,6-dichlorobenzyl)oxy]nicotinate (B3): 6-nitro-5-hydroxynicotinic acid (B2) (3.4 g, 18.5 mmol), 2,6-dichlorobenzyl bromide (8.88 g, 37 mmol), DIPEA (5.5 g, 42.5 mmol) were dissolved in DMF (25 mL) in a 250 mL round bottomed flask and the reaction was stirred at room temperature for 4.5 hr and then concentrated under reduced pressure. The resulting mixture was poured into ice and the filtered. The solid collected was dried under reduced pressure to give 4.25 g (46% yield) of B3. MS (APCI) (M+H)$^+$ 503. $^1$HNMR (DMSO-d$_6$) δ 5.47 (s, 2H, ArCH$_2$O), 5.71 (s, 2H, ArCH$_2$O), 7.24-7.43 (m, 6H, Ar—H), 8.26 (d, 1H, Ar—H), 8.66 (d, 1H, Ar—H).

3. 2,6-Dichlorobenzyl-6-amino-5-[(2,6-dichlorobenzyl)oxy]nicotinate (B4): A mixture of 2,6-dichlorobenzyl-6-nitro-5-[(2,6-dichlorobenzyl)oxy]nicotinate (B3) (5.5 g, 10.96 mmol), iron powder (0.92 g, 16.43 mmol), glacial acetic acid (20 mL) and methanol (17 mL) was stirred at 85° C. for three hr. The reaction mixture was concentrated to near dryness, To an array of 400 μL of 0.2 M solution of different amines in DMF in a 96-well plate was added 400 μL (0.2 M in DMF) of 4-[6-amino-5-(2,6-dichloro-3-fluoro-benzyloxy)-pyridin-3-yl]-benzoic acid, 80 μL of triethylamine (1M in DMF) and 160 μL of HATU (0.5 M in DMF) and the reactions were stirred at 70° C. for 2 hr. The solvent was removed using the SpeedVac apparatus and the crude reaction mixtures were redissolved in DMSO and transferred using a liquid handler to a 1 mL 96-well plate to give a final theoretical concentration of ~10 mM. The reactions were analyzed and positive product identification was made using LC/MS. The mother stock solution was diluted to 50 nM and assayed for percent inhibition of c-MET at 50 nM.

General Procedure 41

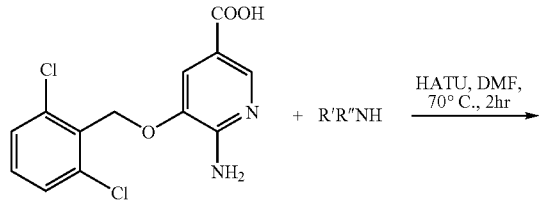

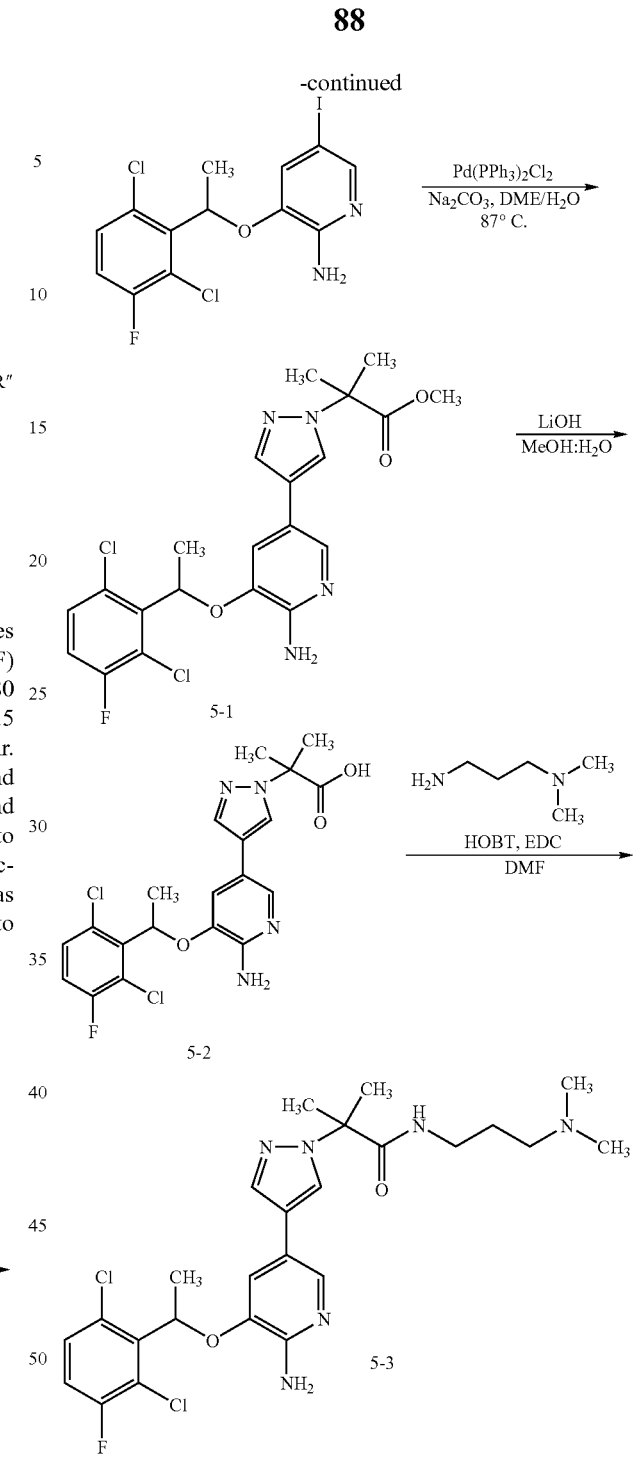

To an array of 400 μL of 0.2 M solution of different amines in DMF in a 96-well plate was added 400 μL (0.2 M in DMF) of 6-Amino-5-[(2,6-dichlorobenzyl)oxy]nicotinic acid, 80 μL of triethylamine (1M in DMF) and 160 μL of HATU (0.5 M in DMF) and the reactions were stirred at 70° C. for 2 hr. The solvent was removed using the SpeedVac apparatus and the crude reaction mixtures were redissolved in DMSO and transferred using a liquid handler to a 1 mL 96-well plate to give a final theoretical concentration of ~10 mM. The reactions were analyzed and positive product identification was made using LC/MS. The mother stock solution was diluted to 1 μM and assayed

General Procedure 42 using 2-(4-{6-amino-5-[1-(2,6-dichloro-3-fluoro-phenyl)-ethoxy]-pyridin-3-yl}-pyrazol-1-yl)-N-(3-dimethylamino-propyl)-isobutyramide

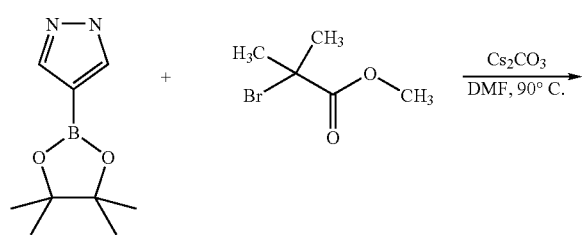

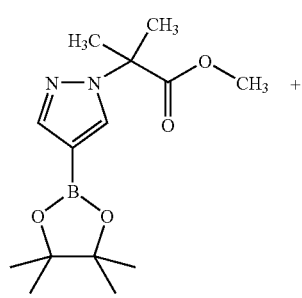

To a solution of 4-(4,4,5,5-tetramethyl-[1,3,2]dioxaborolan-2-yl)-1H-pyrazole (5 g, 25.77 mmol) and 2-bromo-2-methyl-propionic acid methyl ester (12.6 g, 27.06 mmol) in DMF (85 mL), was added $Cs_2CO_3$ (12.6 g, 38.65 mmol). The reaction mixture was heated to 90° C. in an oil bath overnight. The reaction solution was cooled to room temperature, and partitioned between water and ethyl acetate. The combined ethyl acetate solution was washed with water five times, dried over $Na_2SO_4$, and concentrated to give the product 2-methyl-2-[4-(4,4,5,5-tetramethyl-[1,3,2]dioxaborolan-2-yl)-pyrazol-1-yl]propionic acid methyl ester (4.776 g, 63% yield).

To a solution of 3-[1-(2,6-dichloro-3-fluoro-phenyl)-ethoxy]-5-iodo-pyridin-2-ylamine (6.363 g, 14.901 mmol) and 2-methyl-2-[4-(4,4,5,5-tetramethyl-[1,3,2]dioxaborolan-2-yl)-pyrazol-1-yl]propionic acid methyl ester (4.6 g, 15.64 mmol) in DME (27 mL) was added a solution of CsF (6.79 g, 44.7 mmol) in water (9.3 mL). The reaction mixture was degassed 3 times with $N_2$. Pd(dppf)$CH_2Cl_2$ was added and the reaction mixture was degassed 3 times with $N_2$. The reaction was heated to 120° C. in the microwave (subsequent Pd was added in intervals of 30 minutes until the reaction was complete). Water was added and the reaction was extracted with EtOAc, dried over $Na_2SO_4$, and concentrated to give 2-(4-{6-amino-5-[1-(2,6-dichloro-3-fluoro-phenyl)-ethoxy]-pyridin-3-yl}-pyrazol-1-yl)-2-methyl-propionic acid methyl ester. The crude product was purified by a silica gel column chromatography with a gradient of 25%-50% EtOAc/hexanes to provide 2-(4-{6-Amino-5-[1-(2,6-dichloro-3-fluoro-phenyl)-ethoxy]-pyridin-3-yl}-pyrazol-1-yl)-2-methyl-propionic acid methyl ester (1.46 g, 21% yield) with a $R_f$ 0.11 (50% EtOAc/hexanes).

To a solution of the methyl ester (2.92 g, 6.25 mmol) in MeOH (31 mL) was added a solution of LiOH (450 mg, 18.76 mmol) in water (6.25 mL). The reaction was heated to 60° C. until LCMS showed complete hydrolysis (about 45 minutes). The MeOH was removed in vacuo and MeOH (2.5 mL) and water (1 mL) was added. The pH was adjusted to pH 5 with 1N HCl, in which the product precipitated out. The 2-(4-{6-amino-5-[1-(2,6-dichloro-3-fluoro-phenyl)-ethoxy]-pyridin-3-yl}-pyrazol-1-yl)-2-methyl-propionic acid product was obtained after filtration (2.825 g, quant.).

To a solution of 2-(4-{6-amino-5-[1-(2,6-dichloro-3-fluoro-phenyl)-ethoxy]-pyridin-3-yl}-pyrazol-1-yl)-2-methyl-propionic acid (1.00 g, 2.20 mmol) in DMF (5.5 mL) were added HOBT (300 mg, 2.20 mmol), EDC (633 mg, 3.30 mmol), and N,N-dimethyl-propane-1,3-diamine (225 mg, 2.20 mmol). The reaction was stirred overnight at room temperature. The reaction was then purified by reversed phase C-18 prep HPLC eluting with acetonitrile/water with 0.1% acetic acid to afford 2-(4-{6-amino-5-[1-(2,6-dichloro-3-fluoro-phenyl)-ethoxy]-pyridin-3-yl}-pyrazol-1-yl)-N-(3-dimethylamino-propyl)-isobutyramide (170 mg, 14% yield).

General Procedure 43 using 3-[1-(2,6-dichloro-3-fluoro-phenyl)-ethoxy]-5-(3-methyl-pyrazol-1-yl)-pyridin-2-ylamine -continued

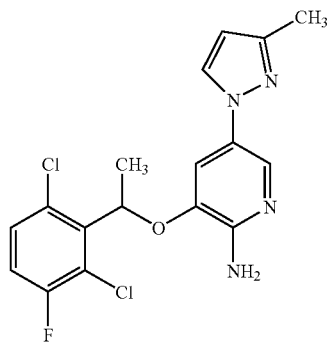

To a stirred solution of 3-[1-(2,6-dichloro-3-fluoro-phenyl)-ethoxy]-5-iodo-pyridin-2-ylamine (100 mg, 0.23 mmol) and 3-methyl-1H-pyrazole (59 mg, 0.70 mmol) in DMSO (1 mL was added $K_3PO_4$ (101 mg, 0.47 mmol), dodecane (0.015 mL, 0.05 mmol), cyclohexanediamine (0.009 mL, 0.07 mmol) and copper iodide (CuI) (14 mg, 0.07 mmol). The solution was bubbled with nitrogen for 5 minutes, then radiated with microwave at 150° C. for 2 hours, LCMS checked that the reaction was completed, the mixture was purified by prep-HPLC to leave 3-[1-(2,6-dichloro-3-fluoro-phenyl)-ethoxy]-5-(3-methyl-pyrazol-1-yl)-pyridin-2-ylamine (30 mg), yield 34.2%

General Procedure 44

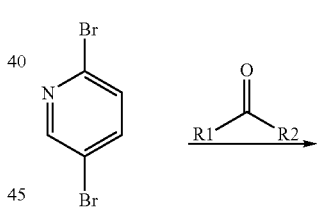

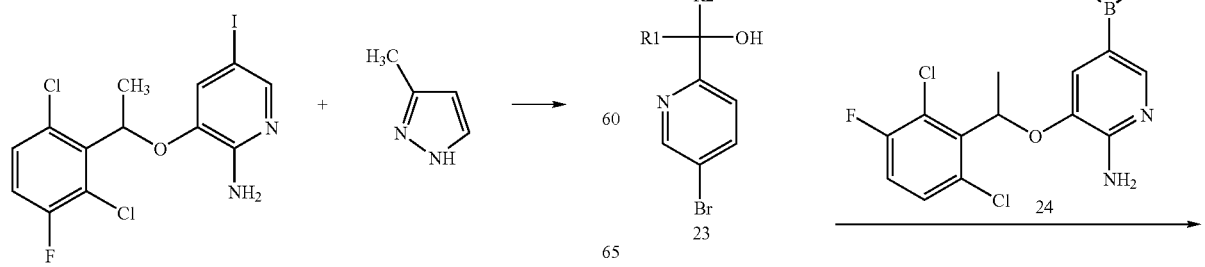

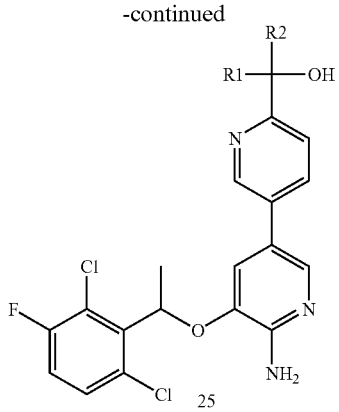

2,5-dibromopyridine (1 molar eq.) was dissolved in anhydrous toluene (0.085 M) and cooled to −78° C. n-BuLi (1.2 molar eq.) was slowly added over 5 minutes and then the resulting mixture allowed to stir at −78° C. After 2 h, $R_1COR_2$ (1.3 molar eq.) was added and the solution kept at −78° C. After 1 h, saturated aqueous $NH_4Cl$ was added and the solution was warmed to room temperature. The product was extracted with EtOAc (3×) and the organic extracts were combined, dried ($Na_2SO_4$), concentrated, and purified by column chromatography (10% EtOAc/Hexanes-100% EtOAc) to afford crude product. It was used directly in General Procedure 27 to afford 25.

General Procedure 45

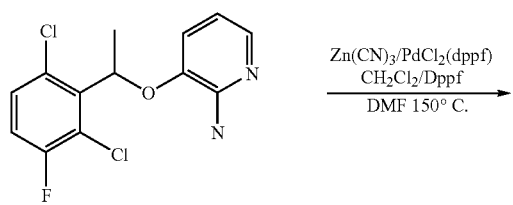

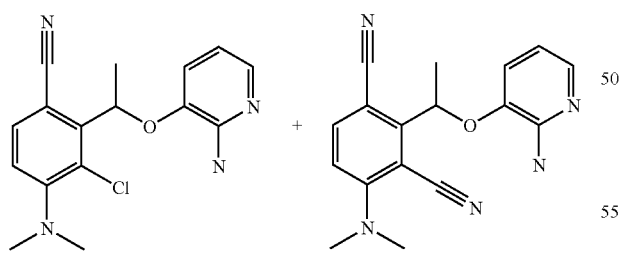

To a solution of 3-[1-(2,6-dichloro-3-fluoro-phenyl)-ethoxy]-pyridin-2-ylamine (1.8 g, 6.04 mmol), zinc cyanide, 98% (2.07 g, 12.07 mmol) and 1,1′-bis(diphenylphosphino)-ferrocene, 97% (0.4 g, 0.712 mmol) in DMF (48 mL) was added [1,1′-bis(diphenylphosphino)-ferrocene]dichloropalladium(II) complex with dichloromethane (1:1) (0.25 g, 0.30 mmol). The reaction mixture was heated to 150° C. for overnight under nitrogen atmosphere. The reaction was diluted with EtOAc (50 mL), washed with 4:1:4 saturated $NH_4Cl$/28% $NH_4OH/H_2O$ (2×28 mL), dried over $Na_2SO_4$. The crude mixture was purified with a silica gel column eluting with a linear gradient of 25%-50% (EtOAc/hexanes) to provide 2-[1-(2-amino-pyridin-3-yloxy)-ethyl]-3-chloro-4-dimethylamino-benzonitrile as a yellow solid (37% yield) and 2-[1-(2-amino-pyridin-3-yloxy)-ethyl]-4-dimethylamino-isophthalonitrile as a dark brown solid (33% yield).

General Procedure 46

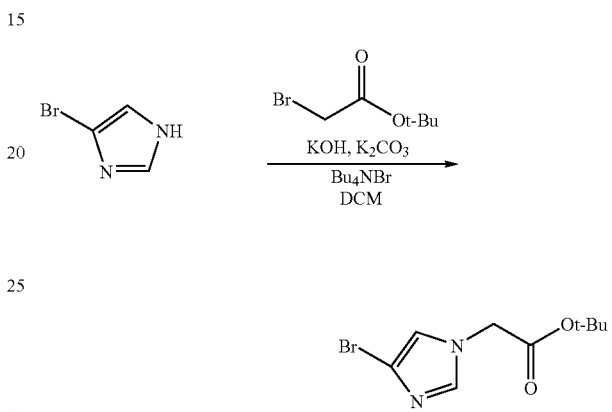

To a mixture of 4-bromo-imidazole (995 mg, 6.77 mmol), potassium hydroxide (380 mg, 6.77 mmol), potassium carbonate (936 mg, 6.77 mmol) and tetra-n-butyl ammonium bromide (109 mg, 0.339 mmol) in dichloromethane (7 mL) was added tert-butyl bromo acetate (0.50 mL, 3.4 mmol). After stirring overnight the reaction was filtered. The filtrate was dried over sodium sulphate, filtered and concentrated by rotary evaporation. The residue was purified by silica gel chromatography using gradient elution of dichloromethane, ethyl acetate to afford (4-Bromo-imidazol-1-yl)-acetic acid tert-butyl ester (696 mg, 79%).

General Procedure 47

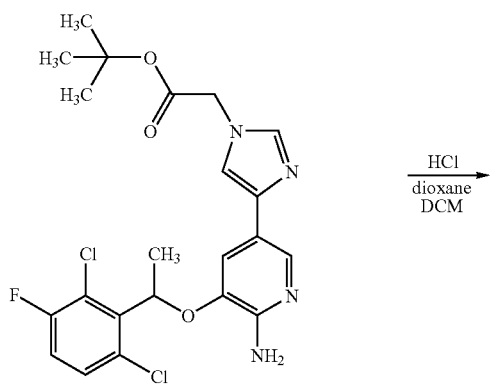

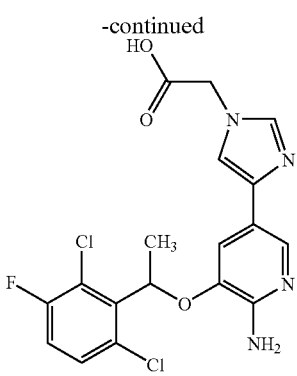

A 4 M solution of hydrochloric acid in dioxane (0.22 mL, 0.89 mmol) was added to a solution of (4-{6-Amino-5-[1-(2,6-dichloro-3-fluoro-phenyl)-ethoxy]-pyridin-3-yl}-imidazol-1-yl)-acetic acid tert-butyl ester (86 mg, 0.18 mmol) in dichloromethane (2 mL). After stirring for two days the reaction was concentrated by rotary evaporation and the residue was dissolved in a minimum amount of methanol. This solution was added dropwise to ether and the resulting mixture allowed to stand overnight. The mixture was filtered and the precipitate was washed with ether and air dried to give (4-{6-Amino-5-[1-(2,6-dichloro-3-fluoro-phenyl)-ethoxy]-pyridin-3-yl}-imidazol-1-yl)-acetic acid (83 mg, 93%).

General Procedure 48

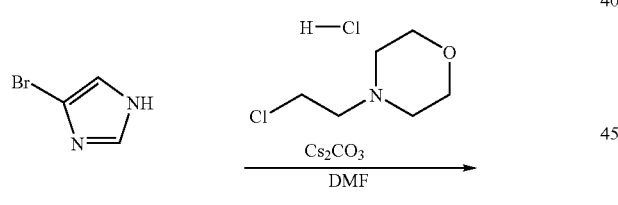

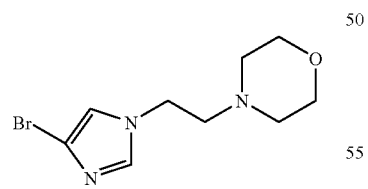

A mixture of 4-bromo-imidazole (217 mg, 1.48 mmol) and cesium carbonate (875 mg, 2.69 mmol) in dimethylformamide (5 mL) was stirred for 30 minutes. 4-(2-Chloro-ethyl)-morpholine hydrochloride (250 mg, 1.34 mmol) was added and the mixture was heated to 50° C. After heating overnight the reaction was concentrated by rotary evaporation. The residue was suspended in a mixture of dichloromethane and methanol and filtered. The filtrate was concentrated by rotary evaporation. The residue was purified by silica gel chromatography using gradient elution of dichloromethane, methanol to afford 4-[2-(4-Bromo-imidazol-1-yl)-ethyl]-morpholine (148 mg, 42%).

General Procedure 49

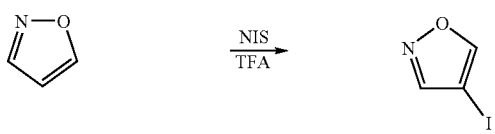

Isoxazole (0.64 mL, 10 mmol) was added to a solution of N-iodosuccinimide (2.3 g, 10 mmol) in trifluoroacetic acid (20 mL). After stirring overnight, water (50 mL), hexanes (50 mL) and sodium bisulfite were added to the reaction. The phases were separated and the organic phase was dried over $Na_2SO_4$, filtered and concentrated by rotary evaporation to give 4-iodo-isoxazole (218 mg, 11%).

General Procedure 50

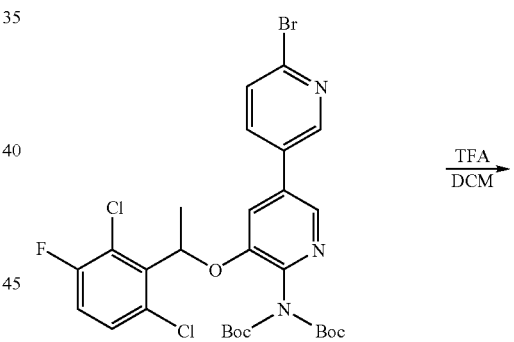

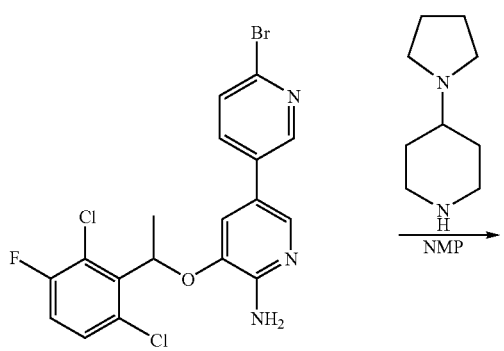

-continued

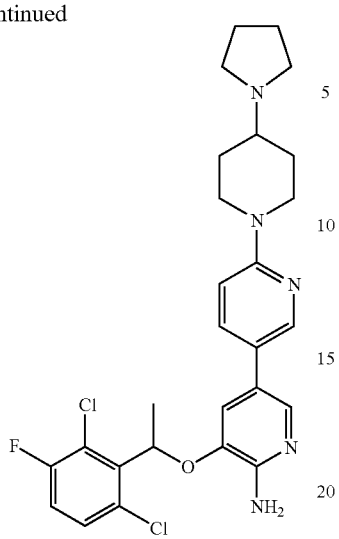

Trifluoroacetic acid (5 mL) was added to a solution of 6'-bromo-5-[1-(2,6-dichloro-3-fluoro-phenyl)-ethoxy]-[3,3'] bipyridinyl-6-yl-bis-(tert-butoxycarbonyl)-amine (1.3 g, 2.0 mmol) in dichloromethane (15 mL). After 3 hours, equal portions of water and saturated aqueous sodium bicarbonate were added. The phases were separated and the aqueous phase was extracted with dichloromethane. The combined organic phases were dried over $Na_2SO_4$ and concentrated by rotary evaporation to give 6'-bromo-5-[1-(2,6-dichloro-3-fluoro-phenyl)-ethoxy]-[3,3']bipyridinyl-6-ylamine (968 mg, 106%).

A tube was charged with 6'-bromo-5-[1-(2,6-dichloro-3-fluoro-phenyl)-ethoxy]-[3,3']bipyridinyl-6-ylamine (92 mg, 0.20 mmol), 4-pyrrolidin-1-yl-piperidine (0.62 g, 4.0 mmol) and N-methylpyrrolidinone (0.8 mL). The tube was sealed and the mixture was heated at 80° C. overnight. The temperature was increased to 100° C. for 5.5 hours and then heating was ceased. The reaction was partitioned between ethyl acetate and water. The phases were separated and the aqueous phase was extracted with ethyl acetate. The combined organic phases were dried over $MgSO_4$ and concentrated by rotary evaporation. The residue was purified by silica gel chromatography using gradient elution of dichloromethane, methanol, ammonium hydroxide to afford 5"-[1-(2,6-dichloro-3-fluoro-phenyl)-ethoxy]-4-pyrrolidin-1-yl-3,4,5,6-tetrahydro-2H-[1,2';5',3"]terpyridin-6"-ylamine (53 mg, 50%).

General Procedure 51

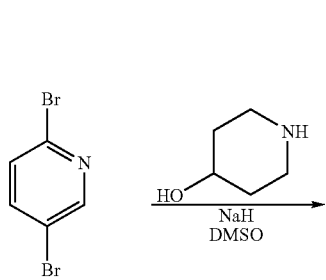

Sodium hydride (56 mg, 2.3 mmol) was added to a solution of piperidin-4-ol (214 mg, 2.11 mmol) in DMSO (8 mL). After stirring for 30 minutes, 2,5-dibromopyridine was added. After stirring for 24 hours, sodium hydride (56 mg, 2.3 mmol) was added. After stirring for another 24 hours the reaction was partitioned between ethyl acetate and water. The phases were separated and the aqueous phase was extracted with ethyl acetate. The combined organic phases were dried over $MgSO_4$ and concentrated by rotary evaporation. The residue was purified by silica gel chromatography using gradient elution of dichloromethane, methanol, ammonium hydroxide to afford 5-bromo-2-(piperidin-4-yloxy)-pyridine (316 mg, 58%).

General Procedure 52

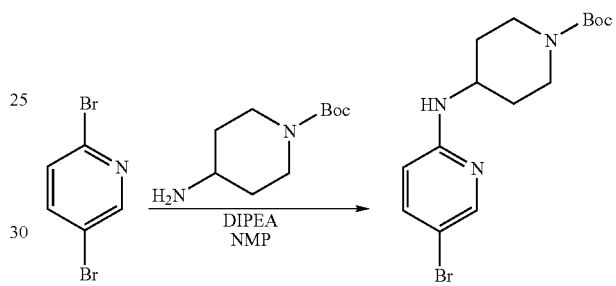

A tube was charged with 2,5-dibromopyridine (0.24 g, 1.0 mmol), 4-Amino-piperidine-1-carboxylic acid tert-butyl ester (0.22 g, 1.1 mmol), di-isopropylethylamine (0.19 mL, 1.1 mmol) and N-methylpyrrolidinone (1.0 mL). The tube was sealed and the mixture was heated at 80° C. overnight. The temperature was increased to 120° C. and heated overnight. The reaction was partitioned between ethyl acetate and water. The phases were separated and the aqueous phase was extracted with ethyl acetate. The combined organic phases were dried over $MgSO_4$ and concentrated by rotary evaporation. The residue was purified by silica gel chromatography using gradient elution of ethyl acetate and hexanes to afford 4-(5-bromo-pyridin-2-ylamino)-piperidine-1-carboxylic acid tert-butyl ester (36 mg, 10%).

General Procedure 53

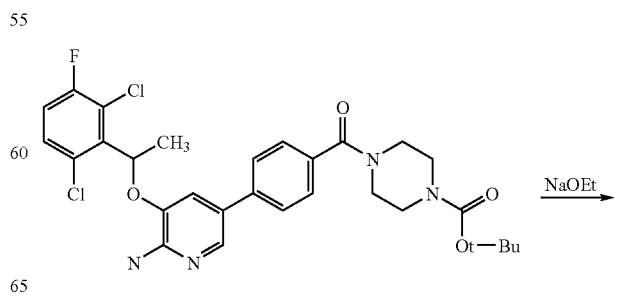

-continued

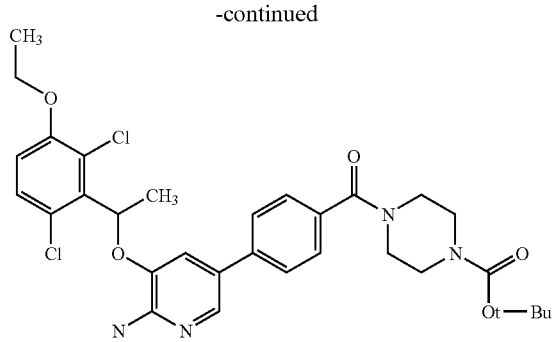

4-(4-{6-Amino-5-[1-(2,6-dichloro-3-ethoxy-phenyl)-ethoxy]-pyridin-3-yl}-benzoyl)-piperazine-1-carboxylic acid tert-butyl ester: To 4 mL of DMSO was added 0.124 ml ethanol followed by 32 mg NaH. After stirring for 30 minutes 250 mg of 250 mg 4-(4-{6-Amino-5-[1-(2,6-dichloro-3-fluoro-phenyl)-ethoxy]-pyridin-3-yl}-benzoyl)-piperazine-1-carboxylic acid tert-butyl ester was added and the reaction was heated to 40° C. After three hours the reaction was cooled and poured into water to precipitate. After neutralization to pH 6, 200 mg of a tan solid was isolated, 77%.

General Procedure 54

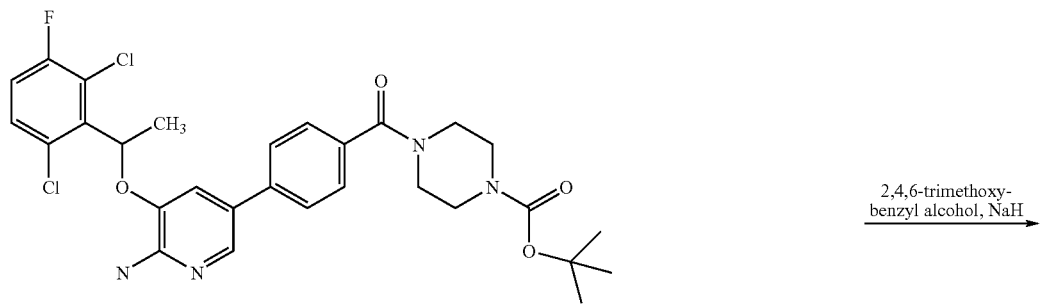

2,4,6-trimethoxy-benzyl alcohol, NaH →

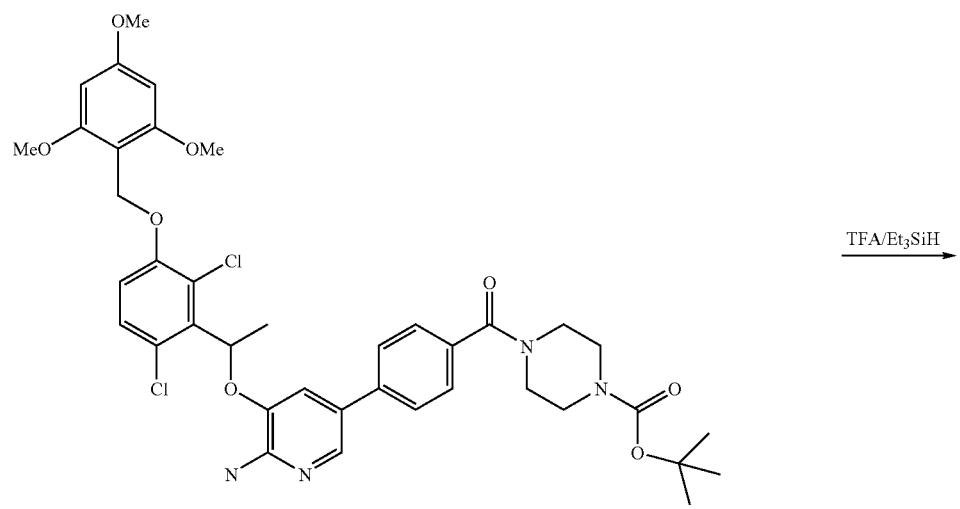

TFA/Et$_3$SiH →

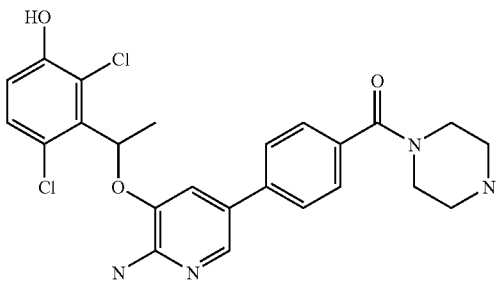

(4-{6-Amino-5-[1-(2,6-dichloro-3-hydroxy-phenyl)-ethoxy]-pyridin-3-yl}-phenyl)-piperazin-1-yl-methanone:
To 140 mg 4-[4-(6-Amino-5-{1-[2,6-dichloro-3-(2,4,6-trimethoxy-benzyloxy)-phenyl]-ethoxy}pyridin-3-yl)-benzoyl]-piperazine-1-carboxylic acid tert-butyl ester (from general procedure 53) was added 1 mL TFA, the solution turned reddish immediately followed by addition of 100 μL triethyl silane 3 seconds later. The solution turned to yellow. After stirring for four hours 5 mL of toluene were added and the solvent was removed in vacuo. Chromatography with 10% MeOH/CH$_2$Cl$_2$ to 0.5% to 1% NH$_4$OH/9.5 to 9% MeOH/90% CH$_2$Cl$_2$ led to 55 mg of a white solid, 62% yield.

General Procedure 55

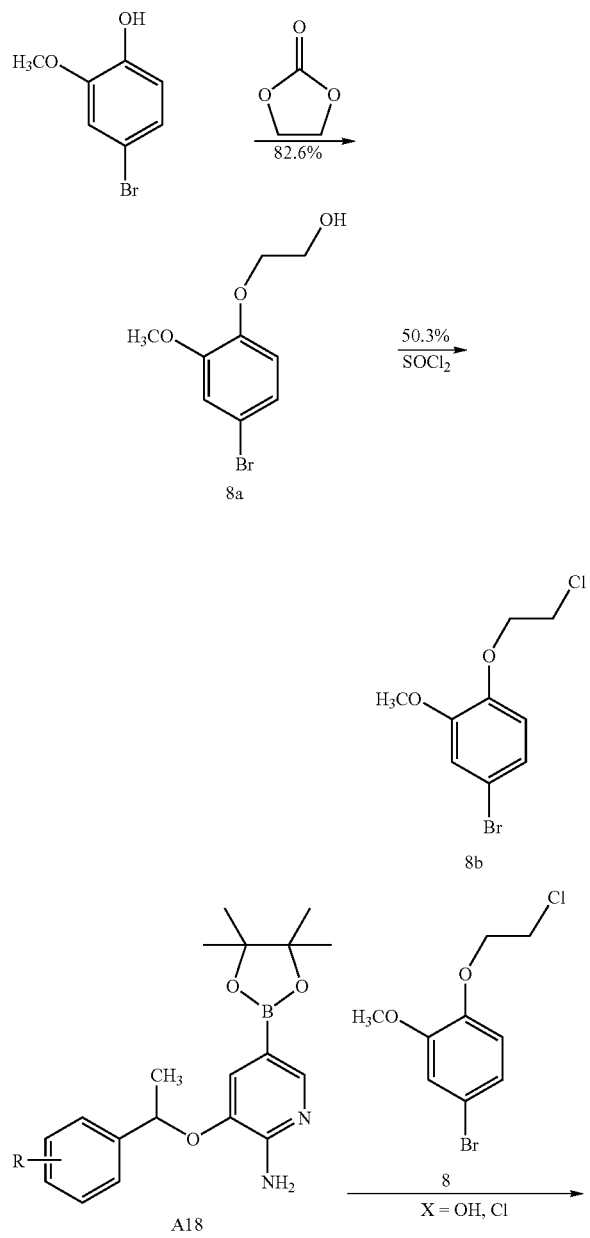

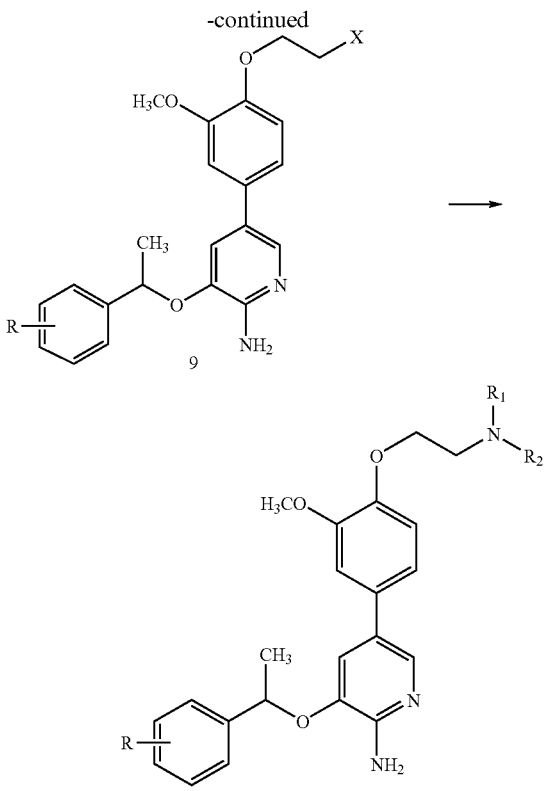

2-(4-bromo-2-methoxyphenoxy)ethanol (8a): Potassium carbonate (1.4 g, 10 mmol) was added to a solution of ethylene carbonate (1.8 g, 20 mmol) and 4-bromo-2-methoxyphenol (1.05 g, 5 mmol) in 5 mL of toluene under an inert atmosphere. The reaction was heated at 115° C. for 12 h. Water (50 mL) and ethyl acetate (2×100 mL) were added to the reaction mixture to stir. The organic layers were combined, dried, filtered, and evaporated to get a yellow oil residue. The residue was purified by flash chromatography (eluting with 40→45% EtOAc in hexanes) to give compound 8a as a light brown yellow oil (1 g; 4.13 mmol; 82.6% yield); MS (APCI) (M+H)$^+$ 246. $^1$H NMR (400 MHz, chloroform-D) δ ppm 2.83 (t, J=6.3 Hz, 1H) 3.84 (s, 3H) 3.89-4.01 (m, 2H) 4.03-4.13 (m, 2H) 6.78 (d, J=8.3 Hz, 1H) 6.99 (d, 1H) 7.02 (d, 1H).

4-bromo-1-(2-chloroethoxy)-2-methoxybenzene (8b): Thionyl chloride (0.3 mL) was added to solution of compound 1 in 1 mL of pyridine in an ice bath. The reaction was stirred in the ice bath for 10 minutes then heated to 100° C. for 2 h. The reaction was cooled to room temperature and neutralized with dilute HCl (1 M). CH$_2$Cl$_2$ (2×100 mL) was added to extract the aqueous solution. The combined organic layers were dried over Na$_2$SO$_4$ then concentrated under vacuum. The residue was purified by flash chromatography (eluting with 10→15% EtOAc in hexanes) to give compound 8b as a colorless oil (485 mg; 1.84 mmol; 50.3% yield); MS (APCI) (M+H)$^+$ 264. $^1$H NMR (400 MHz, chloroform-D) δ ppm 3.81 (t, J=6.2 Hz, 2H) 3.85 (s, 3H) 4.23 (t, J=6.2 Hz, 2H) 6.78 (d, J=8.6 Hz, 1H).

Compound 9: Compounds of formula 9 can be formed by the following exemplary procedure: Compound A18 (1.3 molar equivalent) is added to a solution of aryl halide (0.51 mmol) in 7 mL of DME. The mixture is purged with nitrogen several times and then dichlorobis(triphenylphsophino) palladium (II) (0.05 molar equivalent) is added. Sodium carbonate (3 molar equivalent) in 1.5 mL of $H_2O$ is added to the reaction mixture and the resulting solution is heated to 85° C. for 12 h. Water (20 mL) is added to the reaction mixture to quench the reaction. EtOAc (50 mL×2) is then added to extract the aqueous solution. Dry EtOAc layer over $Na_2SO_4$. The $Na_2SO_4$ is filtered off and the filtrated is evaporated to give a dark brown oil residue. The residue is purified by silica gel chromatography (eluting with $CH_3OH$, $CH_2Cl_2$, EtOAc, and hexanes) to give desired product, compound 9.

Compound 10: Compounds of formula 10 can be formed by the following exemplary procedure: Amine (7 molar equivalent) is added to a solution of compound 9 (0.17 mmol) in 3 mL of 2-methoxyethanol. The resulting solution is heated to 85° C. for 12 h. Water (20 mL) is added to the reaction mixture to quench the reaction. EtOAc (50 mL×2) is then added to extract the aqueous solution. The EtOAc layer is dried over $Na_2SO_4$. The $Na_2SO_4$ is filtered off and the filtrated is evaporated to give a light brown oil residue. The residue is purified by silica gel chromatography (eluting with $CH_3OH$, $CH_2Cl_2$, EtOAc, and hexanes) to give desired product, compound 10.

General Procedure 56

30 min and then 5-bromo-2-chloropyrimidine (1 molar equivalent) is added. The resulting solution is heated to 75° C. for 12 h. Water (20 mL) is added to the reaction mixture to quench the reaction. EtOAc (50 mL×2) is then added to extract the aqueous solution. Dry EtOAc layer over $Na_2SO_4$. The $Na_2SO_4$ is filtered off and the filtrated is evaporated to give an oil residue. The residue is purified by silica gel chromatography (eluting with EtOAc in hexanes) to give desired product, compound 14.

Compound 11: Compound A18 (1.3 molar equivalent) is added to a solution of 5-bromo-2-chloropyrimidine or compound 14 (1 mmol) in 24 mL of DME. The mixture is purged with nitrogen several times and then dichlorobis(triphenylphosphino) palladium (II) (0.05 molar equivalent) is added. Sodium carbonate (3 molar equivalent) in 3 mL of $H_2O$ is added to the reaction mixture and the resulting solution is heated to 85° C. for 12 h. Water (50 mL) is added to the reaction mixture to quench the reaction. EtOAc (100 mL×2) is then added to extract the aqueous solution. Dry EtOAc layer over $Na_2SO_4$. The $Na_2SO_4$ is filtered off and the filtrated is evaporated to give a dark brown oil residue. The residue is purified by flash chromatography (eluting with 40→55% EtOAc in hexanes) to give compound 11.

Compound 12: Amine (2 molar equivalent) is added to a solution of compound 11 in 3 mL of n-butanol. The reaction

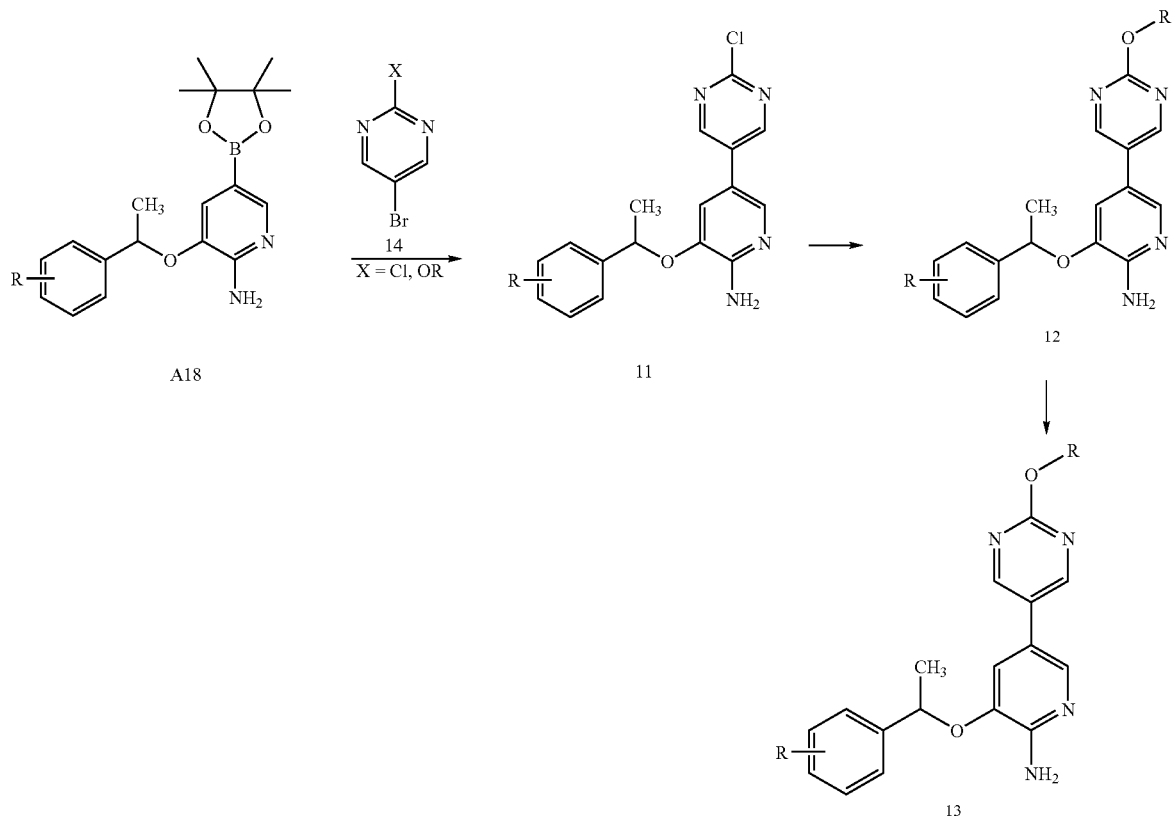

Compound 14: Compounds of formula 14 can be formed by the following exemplary procedure: Lithium hexamethyldisilazide (1.2 molar equivalent; 1M in THF) is added to a solution of alcohol (1 mmol) in 2 mL of THF. The mixture is stirred at room temperature under a nitrogen atmosphere for mixture is irradiated in microwave at 120° C. for 30 min. The resulting mixture is poured into a mixture of $H_2O$ and EtOAc (100 mL; v:v: 1:1). The organic layer is dried, filtered, and evaporated to give a light brown oil residue. The residue is purified by silica gel chromatography (eluting with $CH_3OH$, CH$_2$Cl$_2$, EtOAc, and hexanes) to give desired product, compound 12.

Compound 13: Acid (16 molar equivalent or less) is added to compound 12 (0.14 mmol) at room temperature. The resulting solution is stirred at room temperature or heated to 60° C. for 12 h. The reaction mixture is evaporated and the residue is purified by silica gel chromatography (eluting with CH$_3$OH, EtOAc and CH$_2$Cl$_2$) to give desired amide product, compound 13, as a yellowish to white solid.

General Procedure 57

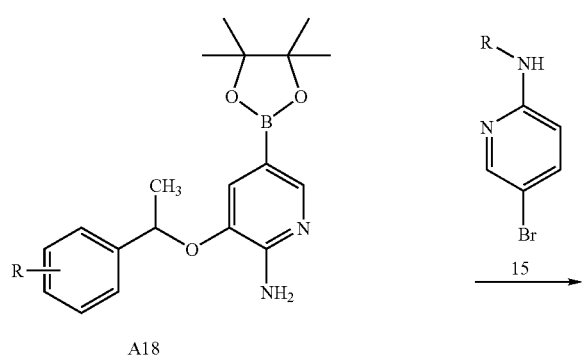

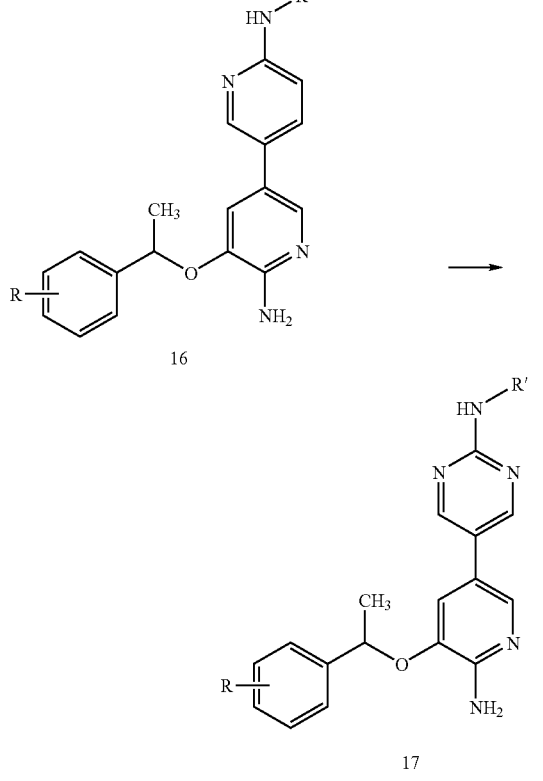

Compound 15: Sodium hydride (1.3 molar equivalent) and RX (1.1 molar equivalent) were added to a solution of 2-amino-5-bromopyridine (0.84 mmol) in 3 mL of DMF. The reaction mixture is irradiated in microwave at 100° C. for 20 min. The resulting mixture is poured into a mixture of H$_2$O and EtOAc (100 mL; v:v: 1:1). The organic layer is dried, filtered, and evaporated to give a light brown oil residue. The residue is purified by silica gel chromatography (eluting with CH$_3$OH, CH$_2$Cl$_2$, EtOAc, and hexanes) to give desired product, compound 15.

Compound 16: Compound A18 (1.3 molar equivalent) is added to a solution of compound 15 (0.25 mmol) in 5 mL of DME. The mixture is purged with nitrogen several times and then dichlorobis(triphenylphosphino) palladium (II) (0.05 molar equivalent) is added. Sodium carbonate (3 molar equivalent) in 0.8 mL of H$_2$O is added to the reaction mixture and the resulting solution is heated to 85° C. for 12 h. Water (50 mL) is added to the reaction mixture to quench the reaction. EtOAc (100 mL×2) is then added to extract the aqueous solution. Dry EtOAc layer over Na$_2$SO$_4$. The Na$_2$SO$_4$ is filtered off and the filtrated is evaporated to give a dark brown oil residue. The residue is purified by flash chromatography (eluting with CH$_3$OH, CH$_2$Cl$_2$, EtOAc, and hexanes) to give desired product, compound 16.

Compound 17: Acid (16 molar equivalent or less) is added to compound 16 (0.114 mmol) at room temperature. The resulting solution is stirred at room temperature or heated to 60° C. for 12 h. The reaction mixture is evaporated and the residue is purified by silica gel chromatography (eluting with CH$_3$OH, EtOAc and CH$_2$Cl$_2$) to give desired amide product, compound 17, as a yellowish to white solid.

General Procedure 58

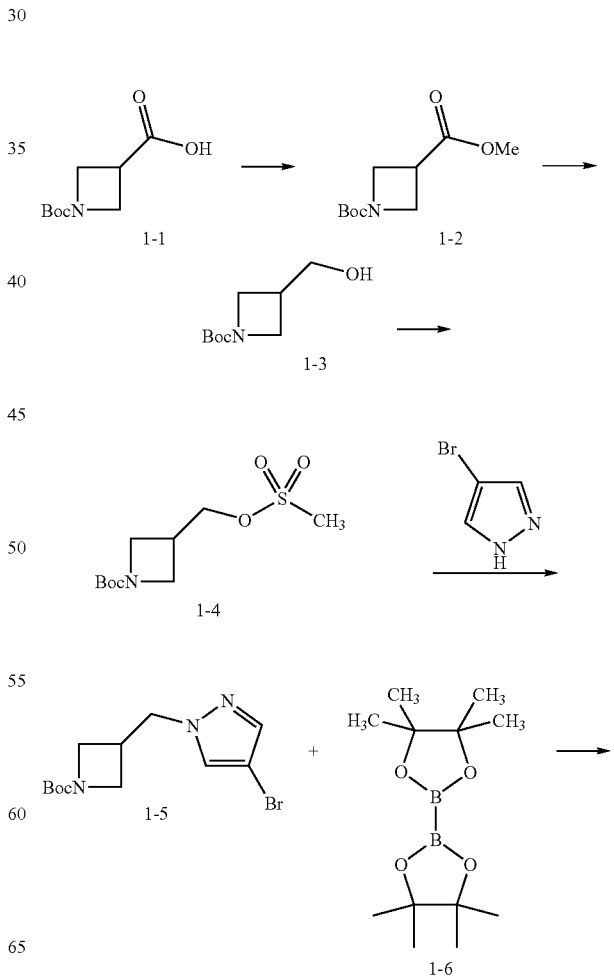

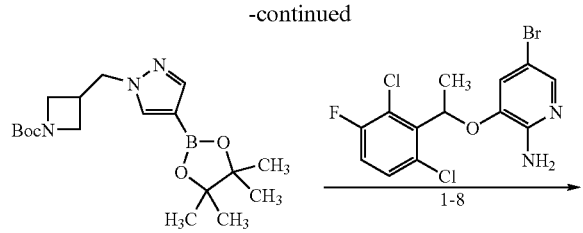

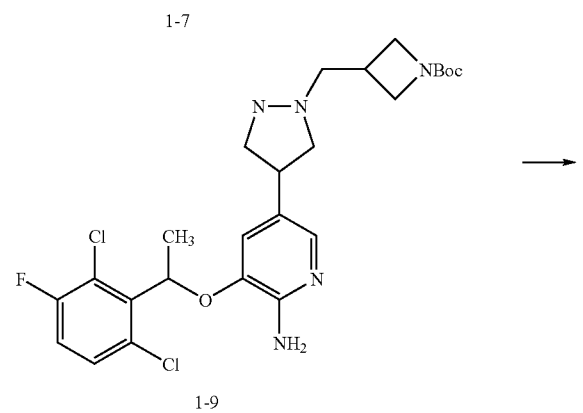

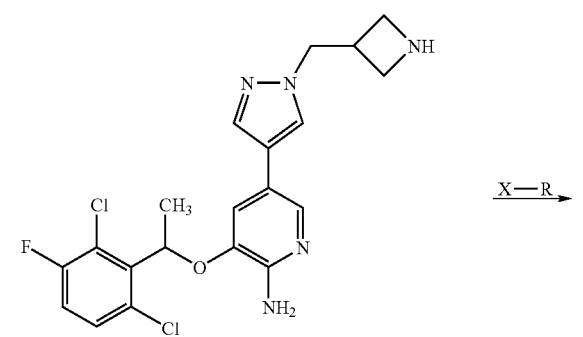

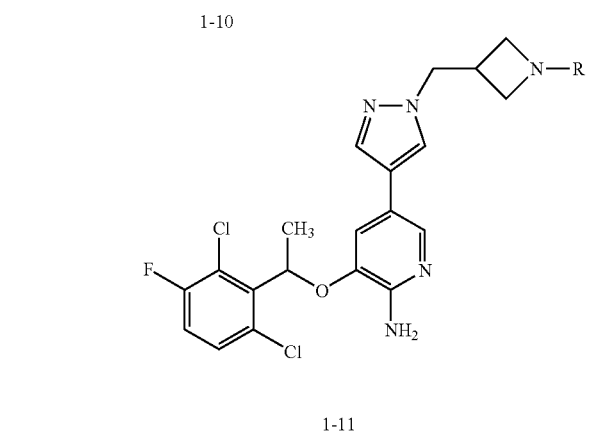

1-(t-butoxycarbonyl) azetidine-3-carboxylic acid (1-1) (AXL016917, 1000 mg, 4.97 mmol) was dissolved in MeOH (5 mL)/Toluene (20 mL) and then cooled to 0° C. TMSCHNN (trimethylsilyldiazomethane) (7.45 mmol) was then added drop-wise over 15 minutes with some bubbling observed. The color started clear and slowly turned yellow. The solution was stirred for 10 minutes at 0° C. and then warmed to room temperature over 30 minutes. The solution was then concentrated and pumped on to remove toluene to afford 1.055 g of 1-t-butyl 3-methyl azetidine-1,3-dicarboxylate (1-2) that was used directly in the next step without being purified (99% crude yield).

1-tert-butyl 3-methyl azetidine-1,3-dicarboxylate (1055 mg, 4.90 mmol) was dissolved in THF (17 mL) and then cooled to 0° C. MeOH (0.397 mL, 9.80 mmol) and LiBH$_4$ (14.7 mmol) were added sequentially. The reaction was warmed to room temperature over 3 h. Then 10% aqueous potassium sodium tartrate tetrahydrate (Rochelle's Salt) (30 mL) and EtOAc (30 mL) were added and the solution stirred at room temperature over 30 minutes. The organic layer was separated and then dried (Na$_2$SO$_4$) and concentrated to afford 674 mg of t-butyl 3-(hydroxymethyl) azetidine-1-carboxylate (1-3) as a crude product (clear oil). The product was used directly in the next step without purification.

t-butyl 3-(hydroxymethyl) azetidine-1-carboxylate (674 mg, 3.60 mmol) was dissolved in CH$_2$Cl$_2$ (13 mL, 0.25M) and then Et$_3$N (1.0 mL, 7.20 mmol), DMAP (44 mg, 0.360 mmol), and methanesulfonyl chloride (0.31 mL, 3.96 mmol) were added sequentially at 0° C. with the MsCl addition being done slowly. The solution was warmed to rt over 1 h. After 15 h, saturated aqueous NaHCO$_3$ (50 mL) was added and then the product was extracted with CH$_2$Cl$_2$ (2×50 mL) and the combined organic extracts were washed with brine (50 mL), dried (Na$_2$SO$_4$), concentrated, and purified by flash chromatography (Biotage Horizon—10% EtOAc/hexanes—100% EtOAc) to afford 962 mg of (1-4) as an oil (quantitative).

NaH (95%, 96 mg, 3.99 mmol) was combined in DMF (10 mL) under N$_2$ at rt. 4-Bromopyrazole (533 mg, 3.63 mmol) was then added and the mixture stirred at rt. After 30 minutes (1-4) was added and the solution heated to 95° C. After 2 h, saturated aqueous NH$_4$Cl (50 mL) was added and then EtOAc (50 mL). The organic extract was dried (Na$_2$SO$_4$) and concentrated, and then run through a short pad of silica gel with 50% EtOAc/Hexanes to afford 846 mg of crude (1-5) that was used directly in the next step (74% crude yield).

(1-5) (846 mg, 2.68 mmol), (1-6) (815 mg, 3.21 mmol), [1,1'-bis(diphenylphosphino)-ferrocene) dichloropalladium (108 mg, 0.133 mmol), and KOAc (893 mg, 9.10 mmol) were combined in DMSO (10 mL, purged with N$_2$ for 10 minutes) and then the solution was warmed to 80° C. After 16 h, the solution was filtered through Celite and then H$_2$O (50 mL) and EtOAc (50 mL) was added. The organic phase was extracted and dried (Na$_2$SO$_4$), concentrated, and then passed through a silica plug with 50% EtOAc/Hexane. The solvent was concentrated to afford 1.22 g of crude (1-7) used directly in the next step.

The boronic ester (1-7) (4144 mg, 11.4 mmol), (1-8) (2890 mg, 7.60 mmol), dichlorobis(triphenylphosphine)palladium (II) (534 mg, 0.760 mmol), DME (40 mL, De-gassed for 30 minutes with N$_2$), and 1N Na$_2$CO$_3$ (40 mL, De-gassed for 30 minutes with N$_2$) were combined and heated to 80° C. After 16 h, the reaction was cooled to rt and EtOAc (80 mL) was added. The solution was filtered through celite and then water (80 mL) was added. The organic layer was separated, dried (Na$_2$SO$_4$), and concentrated. The product was purified by flash chromatography to afford 1486 mg of (1-9) as a tan solid (36%).

1 gram of DOWEX 50WX2-400 ion-exchange resin was prepared by washing it with H$_2$O (500 mL), 1:1H$_2$O/MeOH, MeOH (5×250 mL), CH$_2$Cl$_2$ (500 mL), and hexanes (500 mL). The DOWEX was then dried in a vacuum oven at 40° C. for 1 day. (1-9) was dissolved in MeOH and then DOWEX (588 mg, 1.096 mmol) was added. The solution was stirred at rt for 2 h. The solution was then filtered and the resin was washed with MeOH (3×200 mL) and the wash was discarded. The resin was then washed with 3.5M NH$_3$/MeOH and collected. The solution was then concentrated to afford 374 mg of (1-10) as a gummy solid (78%).

To form compounds of formula (1-11), the following exemplary procedure can be followed. 1 molar equivalent of (1-10) is dissolved in DMF or CH$_2$Cl$_2$ and then base (3 molar equivalents) and/or coupling reagent (1.5 molar equivalents) is added. To the solution is added X-R (1.1 molar equivalent), where X is, for example, Cl, Br, I, OMs, COCl, CO, COOH, ethylene or carbonate and R is a desired group such as those shown in the examples herein or similar groups. The resultant solution is stirred at rt for 4 h. H$_2$O and EtOAc are added and the organic phase extracted, dried (Na$_2$SO$_4$), and concentrated. The crude product can purified by purified by preparative HPLC or other methods well known in the art to afford the product (1-11).

General Procedure 59

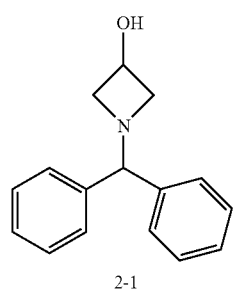

2-1

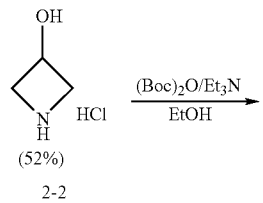 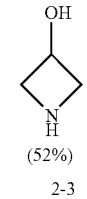

2-2  2-3

2-4

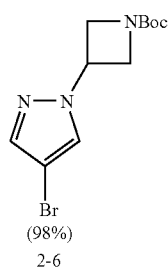

2-6

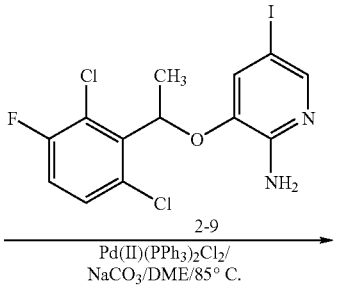

(97%)
2-8

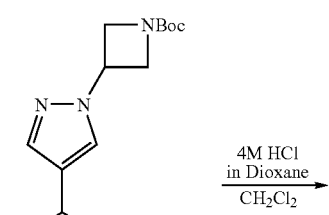

2-9

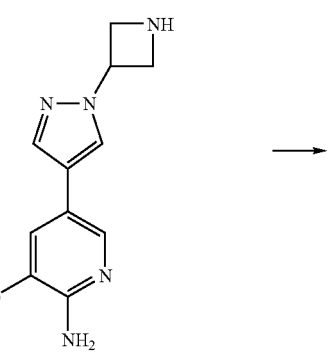

(63%)
2-10

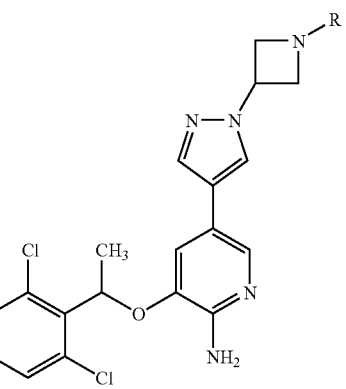

(85%)
2-11

2-12

3-Azetidinol (2-2): A reaction mixture of N-benzhydrylazetidin-3-ol HCl salt (2.76 g, 10.0 mmol) with palladium hydroxide, 20% Pd (dry base) on C (400 mg) in 50 mL of MeOH was hydrogenated at 55 psi for 48 h. The reaction mixture was filtered through Celite pad and washed well with MeOH. The filtrate was concentrated under vacuum at room temperature water bath. The residue was treated with ether (3×30 ml) and the solvent is decanted. The solid was air dried to give 571 mg of HCl salt product (2-2) as white solid (52% yield). $^1$H NMR (400 MHz, DMSO-D6) δ ppm 3.33 (s, 1H) 3.63-3.80 (m, 2H) 3.93-4.09 (m, 2H) 4.40-4.58 (m, 1H) 6.18 (d, J=6.32 Hz, 1H).

3-Hydroxy-azetidine-1-carboxlic acid tert-butyl ester (3-3): To a cold (0° C. bath) stirred solution of compound (2-2) (570 mg, 5.20 mmol) in 10 mL of EtOH was added Et$_3$N (1.8 mL, 13.0 mmol) and di-tert-butyldicarbonate (1.702 g, 7.38 mmol). The resulting mixture of clear solution was stirred at room temperature overnight. The reaction mixture was concentrated by vacuum. The residue was portioned between EtOAc (200 mL) and 0.5N citric acid solution (30 mL; brine (30 mL). The organic layer was dried (Na$_2$SO$_4$), then concentrated by vacuum to give 899 mg (2-3) as clear oil (52%). $^1$H NMR (400 MHz, chloroform-D) δ ppm 1.42 (s, 9H) 3.78 (dd, J=9.47, 4.42 Hz, 2H) 4.13 (dd, J=9.35, 6.57 Hz, 2H) 4.49-4.63 (m, 1H).

3-Methanesulfonyloxy-azetidine-1-carboxylic acid tert-butyl ester (2-4): To a solution of compound (2-3) (466 mg; 2.69 mmol) with Et$_3$N (0.75 mL; 5.38 mmol) and 4-(dimethylamino)-pyridine (33 mg, 0.269 mmol) in 10 mL of CH$_2$Cl$_2$ at 0° C. was added methanesulfonyl chloride (0.25 mL 3.23 mmol). The resulting mixture of brown color solution was stirred at 0° C. to room temperature for overnight. The reaction mixture was quenched with NaHCO$_3$, then partitioned between CH$_2$Cl$_2$ (200 mL) and saturated NaHCO$_3$ solution (50 mL). The organic layer was dried (Na$_2$SO$_4$), then filtered through silica gel pad, eluted with hexane: EtOAc/1:1; the filtrate was concentrated by vacuum to give 614 mg (2-4) as yellow oil (91% yield). $^1$H NMR (400 MHz, chloroform-D) δ ppm 1.43 (s, 9H) 3.05 (s, 3H) 4.08 (dd, J=10.36, 4.29 Hz, 2H) 4.26 (dd, J=10.36, 6.82 Hz, 2H) 5.11-5.26 (m, 1H).

1-(3-Azetidine-1-carboxylic acid tert-butyl ester)-4-bromoprazole (2-6): A 5 mL microwave tube was charge with compound (2-4) (304 mg, 1.21 mmol); 4-bromopyrazole (2-5, 178 mg, 1.21 mmol) and NaH 60% in mineral oil (73 mg, 1.82 mmol.) with 2 mL of DMF. The resulting mixture was microwaved at 110° C. for 30 minutes. The reaction mixture was partitioned between EtOAc (200 mL) and saturated NaHCO$_3$ solution (2×50 mL); brine (50 mL). The organic layer was dried (Na$_2$SO$_4$), then concentrated by vacuum to afford 360 mg of (2-6) as yellow oil (98%). $^1$H NMR (400 MHz, DMSO-D6) δ ppm 1.36-1.43 (m, 9H) 4.08 (s, 2H) 4.18-4.31 (m, 2H) 5.12-5.22 (m, 1H) 7.67 (s, 1H) 8.14 (s, 1H).

tert-Butyl 3-[4-(4,4,5,5-tetramethyl-1,3-dioxoborolan-2-yl)-1H-pyrazol-1-yl]azetidine-1-carboxylate (2-8): A reaction mixture of compound (2-6) (225 mg, 0.74 mmol) and bis(pinacolate)diboron (2-7, 227 mg, 0.89 mmol) with KOAc (247 mg, 2.52 mmol) in 3 mL of DMSO was purged with N$_2$ for 15 minutes, then PdCl$_2$(dppf)$_2$CH$_2$Cl$_2$ (30 mg, 2.52 mmol) was added. The resulting mixture was stirred at 80° C. under N$_2$ for overnight. After it cooled down to room temperature, the mixture was filtered through Celite pad and washed well with EtOAc. The filtrate was extracted with H$_2$O (2×50 mL), brine (50 mL). The organic layer was dried (Na$_2$SO$_4$), then concentrated by vacuum. The residue was then filtered through silica gel pad, eluted with hexane: EtOAc/3:2. The filtrate was concentrated by vacuum to give 250 mg of 2-8) as a clear oil (97% yield). $^1$H NMR (400 MHz, chloroform-D) δ ppm 1.18-1.27 (m, 9H) 1.28-1.34 (m, 6H) 1.41-1.49 (m, 6H) 4.22-4.33 (m, 2H) 4.36 (t, J=8.59 Hz, 2H) 4.98-5.13 (m, 1H) 7.83 (s, 2H).

tert-Butyl 3-(4-{6-amino-5-[1-(2,6-dichloro-3-fluorophenyl)ethoxy]pyridin-3-yl}-1H-pyrazol-1-yl)azetidine-1-carboxylate (2-10): A reaction mixture of compound (2-8) (459 mg; 1.31 mmol) and 3-[1-(2,6-dichloro-3-fluorophenyl)ethoxy]-5-iodopyridin-2-amine (2-9) (374 mg; 0.88 mmol) in 13 mL of ethylene glycol dimethylether, anhydrous (DME) was purged with N$_2$ for 15 minutes, then Pd(II)(PPh$_3$)$_2$Cl$_2$ (46 mg, 0.07 mmol) was added and continued to purge with N$_2$ for another 15 minutes. Another 1.0 N Na$_2$CO$_3$ solution (3.9 mL; 3.9 mmol) was added after purging with N$_2$ for 15 minutes. The resulting mixture was stirred at 85° C. under N$_2$ for overnight. The reaction mixture was filtered through Celite pad and washed well with MeOH. The filtrate was concentrated by vacuum. The residue was partitioned between EtOAc (200 mL) and saturated NaHCO$_3$ solution (2×50 mL); brine (50 mL). The organic layer was dried (Na$_2$SO$_4$), then concentrated by vacuum. The residue was purified by Biotage system (25 M, 100% CH$_2$Cl$_2$; 100% CH$_2$Cl$_2$ to 90% CH$_2$Cl$_2$ with 10% MeOH) to collect the desired fraction to afford 421 mg of (2-10) as a brown color grease (92% yield). $^1$H NMR (400 MHz, chloroform-D) δ ppm 1.17-1.26 (m, 9H) 1.80-1.87 (m, 3H) 4.04-4.18 (m, 2H) 4.20-4.33 (m, 2H) 4.34-4.41 (m, 1H) 4.79 (s, 2H) 5.02 (d, J=7.58 Hz, 1H) 7.04 (t, J=8.46 Hz, 1H) 7.33-7.41 (m, 1H) 7.44-7.52 (m, 1H) 7.53-7.58 (m, 1H) 7.59-7.65 (m, 1H) 7.72-7.78 (m, 1H); LCMS calcd for C$_{24}$H$_{26}$Cl$_2$FN$_5$O$_3$ (M+H) 523, found 523.

5-(1-Azetidin-3-yl-1H-pyrazol-4-yl)-3-[1-(2,6-dichloro-3-fluorophenyl)ethoxy]yridin-2-amine (2-11): A reaction mixture of compound (2-10) (421 mg; 0.81 mmol) with 4.0 M HCl in dioxane (2.0 mL; 8.1 mmol) in 5 mL of CH$_2$Cl$_2$ was stirred at room temperature for 2.0 hours. The reaction mixture was concentrated by vacuum. The residue was treated with EtOAc. The precipitated solid was filtered off and washed well with EtOAc, hexane, then dried under vacuum to give 275 mg of (2-11) as a sand color solid of HCl salt (81% yield). $^1$H NMR (400 MHz, DMSO-D6) δ ppm 1.79-1.89 (m, 3H) 3.56 (s, 1H) 4.35 (s, 4H) 5.40 (s, 1H) 6.23 (d, J=6.57 Hz, 2H) 7.09 (s, 1H) 7.40-7.54 (m, 1H) 7.59 (dd, J=8.84, 5.05 Hz, 1H) 7.73-7.83 (m, 1H) 7.86 (s, 1H) 8.12 (s, 1H) 9.20 (s, 1H). LCMS calcd for C$_{19}$H$_{18}$Cl$_2$FN$_5$O (M+H) 423, found 423.

Compounds of formula 2-12 can be prepared by the following exemplary procedure: To a reaction mixture of compound (2-11) (1.0 eq.) with Et$_3$N (2.0 eq.) in 2.0 mL of DMF at room temperature is added alkyl bromide (1.1 eq.). The resulting mixture is stirred under N$_2$ at room temperature for overnight. The reaction mixture is partitioned between EtOAc (200 mL) and saturated NaHCO$_3$ solution (2×50 mL); brine (50 mL). The organic layer is dried (Na$_2$SO$_4$), then concentrated by vacuum. The residue is purified by Dionex system (5% to 95% MeCN:H$_2$O w 0.1% HOAc buffer) to collect the desired fraction to afford (2-12).

Alternatively, compounds of formula 2-12 can be prepared by the following exemplary procedure: To a reaction solution of alkyl amine (1.0 eq.) with iPr$_2$EtN (diisopropylethylamine) (3.0 eq.) in 2.0 mL of DMF is added HATU (1.5 eq.). After stirring for 30 minutes, compound (2-11) (1.0 eq.) is added. The resulting mixture is stirred at room temperature for overnight. The reaction mixture is partitioned between EtOAc (200 mL) and saturated NaHCO$_3$ solution (2×50 mL) and brine (50 mL). The organic layer is dried (Na$_2$SO$_4$) and concentrated by vacuum. The residue is purified by Dionex System (5% to 95% MeCN:H$_2$O w 0.1% HOAc) to collect the desired product to afford (2-12).

General Procedure 60

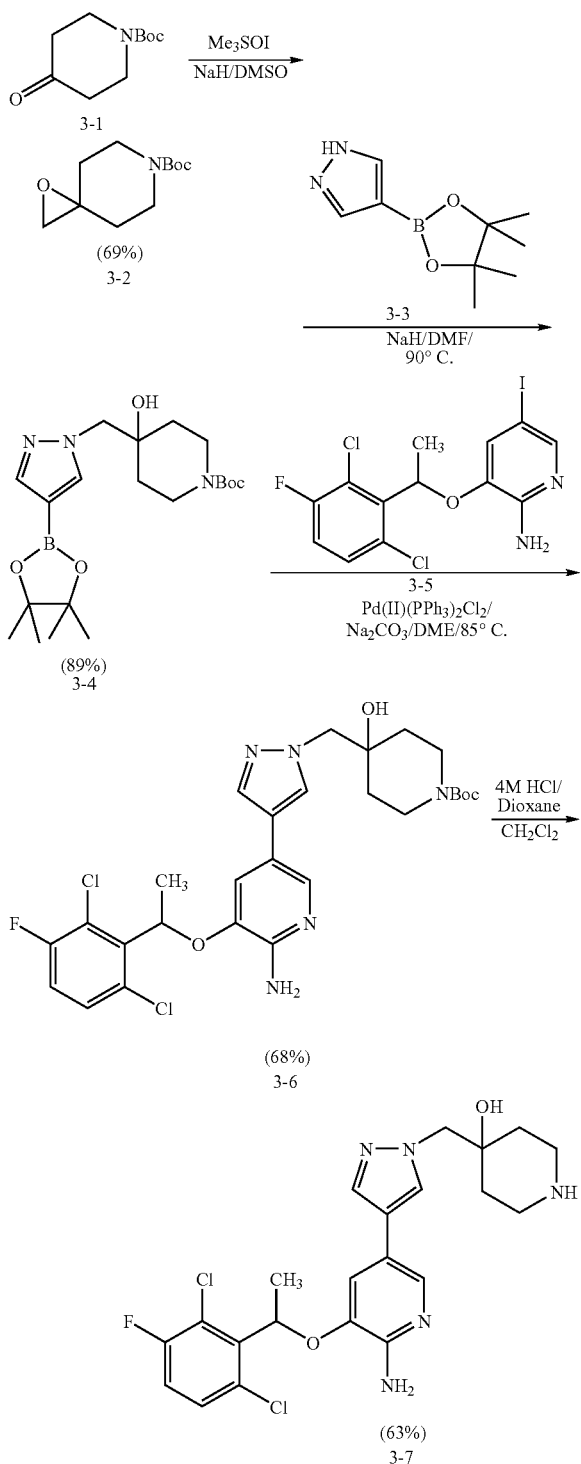

tert-Butyl 1-oxa-6-azaspiro[2.5]octane-6-carboxylate (3-2): A solution of dimethylsulfoxonium methylide was prepared under N$_2$ from NaH 60% dispersion in mineral oil (440 mg; 11.0 mmol) and trimethylsulfoxonium iodide (2.421 g; 11.0 mmol) in 5 ml of anhydrous DMSO. Another solution of 1-Boc-4-oxo-1-piperidincarboxylate (3-1, 1.993 g; 10.0 mmol) in 5 mL of DMSO was added dropwise. The resulting mixture was stirred at 55° C. for 6 hours. The cooled reaction mixture was poured into ice-H$_2$O and extracted with EtOAc (2×200 mL). The combined organic layers were washed with H$_2$O (50 mL); brine (50 mL) and then dried (Na$_2$SO$_4$), then concentrated by vacuum to give 1.4791 g of (3-2) as a yellow oil (69% yield). $^1$H NMR (400 MHz, chloroform-D) δ ppm 1.37-1.52 (m, 11H) 1.71-1.84 (m, 2H) 2.63-2.72 (m, 2H) 3.35-3.49 (m, 2H) 3.62-3.78 (m, 2H).

tert-Butyl 4-hydroxy-4-{[4-(4,4,5,5-tetramethyl-1,3,2-dioxaborolan-2-yl)-1H-pyrazol-1-yl]methyl}piperidine-1-carboxylate (3-4): A reaction mixture of compound (3-2) (214 mg; 1.0 mmol) and 4-(4,4,5,5-tetramethyl-1,3,2-dioxaborolan-2-yl)-1H-pyrazole (3-3, 194 mg; 1.0 mmol) with NaH 60% dispersion in mineral oil (60 mg; 1.5 mmol) in 3 mL of DMF was stirred at 90° C. for 3 hours. The reaction mixture was partitioned between EtOAc (200 mL) and saturated NaHCO$_3$ solution (50 mL) and brine (50 mL). The organic layer was dried (Na$_2$SO$_4$) and concentrated by vacuum to give 361 mg of (3-4) as a yellow grease (89% yield). $^1$H NMR (400 MHz, chloroform-D) δ ppm 1.21-1.34 (m, 12H) 1.39-1.50 (m, 9H) 1.56-1.78 (m, 4H) 3.14 (s, 2H) 3.72-3.91 (m, J=32.34 Hz, 2H) 4.05 (s, 2H) 7.65 (s, 1H) 7.80 (s, 1H) 8.00 (s, 1H). LCMS calcd for C$_{20}$H$_{34}$BN$_3$O$_5$ (M+H) 408, found 408. HPLC purity 85%.

tert-Butyl 4-[(4-{6-amino-5-[1-(2,6-dichloro-3-fluorophenyl)ethoxy]pyridin-3-yl}-H-pyrazol-1-yl)methyl]4-hydroxypiperidine-1-carboxylate (3-6): A reaction mixture of compound (3-4) (361 mg; 0.89 mmol) and 3-[1-(2,6-dichloro-3-fluorophenyl)ethoxy]-5-iodopyridin-2-amine (3-5) (378 mg; 0.89 mmol) in 9.0 mL of ethylene glycol dimethylether, anhydrous (DME) was purged with N$_2$ for 15 minutes, then Pd(II)(PPh$_3$)$_2$Cl$_2$ (32 mg, 0.05 mmol) was added and continued to purge with N$_2$ for another 15 minutes. Another 1.0 N Na$_2$CO$_3$ solution (3.9 mL; 3.9 mmol) was added after purging with N$_2$ for 15 minutes. The resulting mixture was stirred at 85° C. under N$_2$ for overnight. The reaction mixture was filtered through Celite pad and washed well with MeOH. The filtrate was concentrated by vacuum. The residue was partitioned between EtOAc (200 mL) and saturated NaHCO$_3$ solution (2×50 mL); brine (50 mL). The organic layer was dried (Na$_2$SO$_4$), then concentrated by vacuum. The residue was purified by Dionex system (25% to 95% MeCN:H$_2$O w 0.1% HOAc buffer) to collect the desired fraction to afford 147 mg of (3-6) as a white solid (28% yield). $^1$H NMR (400 MHz, DMSO-D6) δ ppm 1.34-1.39 (m, 9H) 1.70-1.77 (m, 2H) 1.79 (d, J=6.57 Hz, 3H) 3.06 (d, J=12.63 Hz, 2H) 3.62 (s, 2H) 4.03 (s, 2H) 4.79 (s, 1H) 5.66 (s, 2H) 6.08 (d, J=6.82 Hz, 1H) 6.86 (d, J=1.52 Hz, 1H) 7.44 (t, J=8.72 Hz, 1H) 7.51-7.58 (m, 2H) 7.58-7.65 (m, 2H) 7.73 (d, J=1.52 Hz, 1H) 7.78 (s, 1H). LCMS calcd for C$_{27}$H$_{32}$Cl$_2$FN$_5$O$_4$ (M+H) 581, found 581. HPLC purity 87%.

4-[(4-{6-amino-5-[1-(2,6-dichloro-3-fluorophenyl)ethoxy]pyridin-3-yl}-1H-pyrazol-1-yl)methyl]piperidin-4-ol (3-7): A reaction mixture of compound (3-6) (145 mg; 0.25 mmol) with 4.0 M HCl in dioxane (2.0 mL; 8.1 mmol) in 5 mL of CH$_2$Cl$_2$ was stirred at room temperature for 2.0 hours. The reaction mixture was concentrated by vacuum. The residue was purified by Dionex system (5% to 95% MeCN:H$_2$O w 0.1% HOAc buffer) to collect the desired fraction to afford 76 mg of (3-7) as a yellow grease (63% yield). $^1$H NMR (400 MHz, DMSO-D6) δ ppm 1.41-1.55 (m, 2H) 1.59-1.71 (m, 2H) 1.81 (d, J=6.57 Hz, 3H) 2.88-3.00 (m, 2H) 3.02-3.14 (m, 2H) 4.08 (s, 2H) 5.17 (s, 2H) 6.14-6.27 (m, J=6.57 Hz, 1H)

7.05 (s, 1H) 7.40-7.49 (m, J=8.72, 8.72 Hz, 1H) 7.51-7.60 (m, J=9.09, 4.80 Hz, 1H) 7.63 (s, 1H) 7.76 (s, 1H) 7.91 (s, 1H) 8.51 (s, 1H) 8.81 (s, 1H). LCMS calcd for $C_{22}H_{24}Cl_2FN_5O_2$ (M+H) 481, found 481. HPLC purity 98%. Anal. ($C_{22}H_{24}Cl_2FN_5O_2 \times 2.2HOAc \times 2.3H_2O$) C, H, N.

General Procedure 61

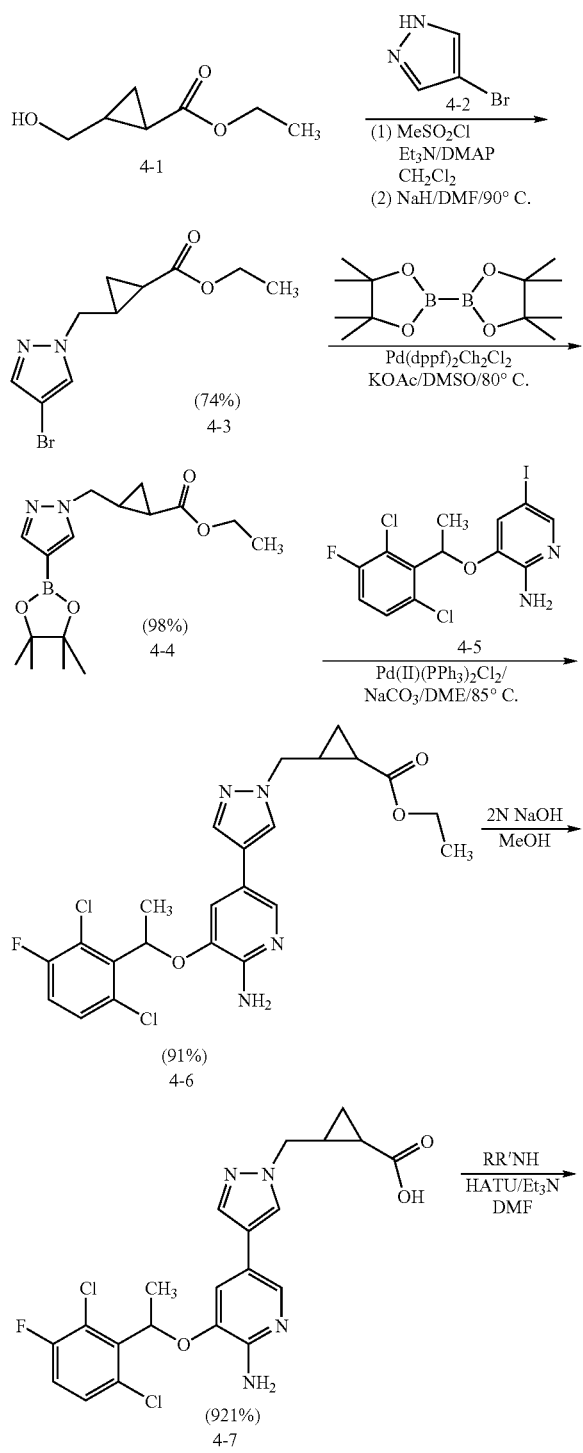

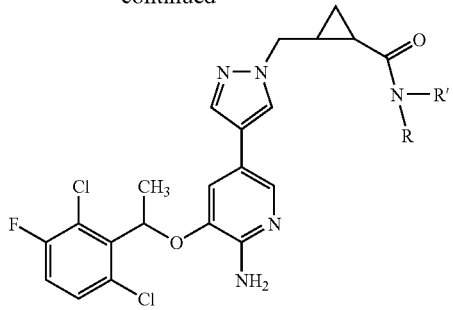

Ethyl 2-[(4-bromo-1H-pyrazol-1-yl)methyl]cyclopropanecarboxylate (4-3): To a reaction solution of ethyl 2-(hydroxymethyl)cyclopropanecarboxylate (4-1) (577 mg; 4.0 mmol) with $Et_3N$ (1.1 mL; 8.0 mmol) and DMAP (49 mg; 0.4 mmol) in 12 mL of $CH_2Cl_2$ at 0° C. was added methanesulfonyl chloride (0.4 mL; 4.8 mmol). The resulting mixture of brown color suspension was stirred at 0° C. to room temperature under $N_2$ for overnight. The reaction mixture was quenched with $NaHCO_3$, then partitioned between $CH_2Cl_2$ (200 mL) and saturated $NaHCO_3$ solution (50 mL); brine (50 mL). The organic layer was dried ($Na_2SO_4$), then filtered through silica gel pad, eluted with hexane:EtOAc/1:1. The filtrate was concentrated by vacuum to give 880 mg of ethyl 2-{[(methylsulfonyl)oxy]methyl}cyclopropanecarboxylate as a yellow oil (99% yield). $^1$H NMR (400 MHz, chloroform-D) δ ppm 0.91-1.02 (m, 1H) 1.26 (q, J=6.99 Hz, 3H) 1.29-1.36 (m, 1H) 1.63-1.74 (m, 1H) 1.79-1.92 (m, 1H) 3.02 (s, 3H) 3.99-4.24 (m, 4H).

A reaction mixture of ethyl 2-{[(methylsulfonyl)oxy]methyl}cyclopropanecarboxylate (880 mg; 4.0 mmol), 4-bromopyrazole (4-2, 588 mg, 4.0 mmol) and NaH 60% in mineral oil (240 mg, 6.0 mmol) with 3.0 mL of DMF was formed. The resulting mixture was stirred at 90° C. under $N_2$ for four hours. The reaction mixture was partitioned between EtOAc (200 mL) and saturated $NaHCO_3$ solution (2×50 mL); brine (50 mL). The organic layer was dried ($Na_2SO_4$), then concentrated by vacuum to afford 812 mg of (4-3) as a yellow oil (74%). $^1$H NMR (400 MHz, chloroform-D) δ ppm 0.85 (dd, J=7.96, 3.16 Hz, 1H) 0.88-0.98 (m, 1H) 1.18-1.29 (m, 3H) 1.56-1.71 (m, 1H) 1.79-1.94 (m, 1H) 3.96-4.08 (m, 2H) 4.07-4.17 (m, 2H) 7.45 (d, J=3.79 Hz, 2H). LCMS calcd for $C_{10}H_{13}BrN_2O_2$ (M+H) 274, found 274. HPLC purity 95%.

Ethyl 2-{[4-(4,4,5,5-tetramethyl-1,3-dioxoborolan-2-yl)-1H-pyrazol-1-yl]methyl}cyclopropanecarboxylate (4-4): A reaction mixture of compound (4-3) (812 mg, 2.97 mmol) and bis(pinacolate)diboron (906 mg, 3.57 mmol) with KOAc (991 mg, 10.10 mmol) in 10.0 mL of DMSO was purged with $N_2$ for 15 minutes, then $PdCl_2(dppf)_2CH_2Cl_2$ (122 mg, 0.15 mmol) was added. The resulting mixture was stirred at 80° C. under $N_2$ for overnight. After cooling down to room temperature, the mixture was filtered through Celite pad and washed well with EtOAc. The filtrate was extracted with $H_2O$ (2×50 mL), brine (50 mL). The organic layer was dried ($Na_2SO_4$), then concentrated by vacuum. The residue was then filtered through silica gel pad, and eluted with hexane:EtOAc/3:1. The filtrate was concentrated by vacuum to give 945 mg of (4-4) as a yellow oil (98% yield). $^1$H NMR (400 MHz, chloroform-D) δ ppm 0.85 (dd, J=7.83, 3.03 Hz, 1H) 0.90-0.96 (m, 1H) 1.20-1.24 (m, 3H) 1.29-1.34 (m, 12H) 1.62-1.71 (m, 1H) 1.84-1.97 (m, 1H) 3.96-4.07 (m, 1H) 4.06-4.14 (m, 2H) 4.15-4.23 (m, J=14.27, 6.44 Hz, 1H) 7.73 (s, 1H) 7.77 (s, 1H).

Ethyl 2-[(4-{6-amino-5-[1-(2,6-dichloro-3-fluorophenyl)ethoxy]pyridin-3-yl}-1H-pyrazol-1-yl)methyl]cyclopropanecarboxylate (4-6): A reaction mixture of compound (4-4) (643 mg; 2.01 mmol) and 3-[1-(2,6-dichloro-3-fluorophenyl)ethoxy]-5-iodopyridin-2-amine (4-5) (572 mg; 1.34 mmol) in 20.0 mL of ethylene glycol dimethylether, anhydrous (DME) was purged with $N_2$ for 15 minutes, then $Pd(II)(PPh_3)_2Cl_2$ (71 mg, 0.1 mmol) was added and continued to purge with $N_2$ for another 15 minutes. Another 1.0 N $Na_2CO_3$ solution (6.0 mL; 6.0 mmol) was added after purging with $N_2$ for 15 minutes. The resulting mixture was stirred at 85° C. under $N_2$ for overnight. The reaction mixture was filtered through Celite pad and washed well with MeOH. The filtrate was concentrated by vacuum. The residue was partitioned between EtOAc (200 mL) and saturated $NaHCO_3$ solution (2×50 mL); brine (50 mL). The organic layer was dried ($Na_2SO_4$), then concentrated by vacuum. The residue was purified by Biotage system (25 M $CH_2Cl_2$ 100%; $CH_2Cl_2$ 100% to 90% $CH_2Cl_2$: 10% MeOH) to collect the desired fraction to afford 600 mg of (4-6) as a brown color grease (91% yield). $^1H$ NMR (400 MHz, DMSO-D6) δ ppm 0.96-1.10 (m, 2H) 1.15 (t, J=7.07 Hz, 2H) 1.74 (s, 3H) 1.79 (d, J=6.57 Hz, 3H) 3.95-4.14 (m, 4H) 5.66 (s, 2H) 6.08 (d, J=6.57 Hz, 1H) 6.88 (s, 1H) 7.43 (t, J=8.72 Hz, 1H) 7.49-7.62 (m, 2H) 7.73 (s, 1H) 7.88 (s, 1H). LCMS calcd for $C_{23}H_{23}Cl_2FN_4O_3$ (M+H) 494, found 494. HPLC purity 95%.

2-[(4-{6-amino-5-[1-(2,6-dichloro-3-fluorophenyl)ethoxy]pyridin-3-yl}-1H-pyrazol-1-yl)methyl]cyclopropanecarboxylic acid (4-7): To a reaction solution of compound (4-6) (377 mg, 0.76 mmol) in 5.0 mL of MeOH at room temperature under $N_2$ was added another solution of 2.0 N NaOH (2) (1.5 mL, 3.04 mmol). The resulting mixture was stirred at 80° C. for 3 hours. The reaction mixture was concentrated by vacuum to remove most of the MeOH and acidified by 2 M HCl to pH 4.0. The mixture was extracted with $CH_2Cl_2$ (2×200 mL); the organic layers were washed with brine (50 mL), and dried ($Na_2SO_4$) and concentrated by vacuum to give 324 mg of (4-7) as a yellow solid. (92% yield). $^1H$ NMR (400 MHz, DMSO-D6) δ ppm 0.92-1.04 (m, 2H) 1.57-1.72 (m, 2H) 1.76-1.90 (m, 3H) 3.98-4.18 (m, 2H) 6.46 (s, 2H) 6.89-7.02 (m, 1H) 7.29-7.52 (m, 2H) 7.52-7.63 (m, 2H) 7.73 (d, J=1.52 Hz, 1H) 7.94 (s, 1H) 12.19 (s, 1H). LCMS calcd for $C_{21}H_{19}Cl_2FN_4O_3$(M−H) 463, found 463. HPLC purity 87%.

2-[(4-{6-amino-5-[1-(2,6-dichloro-3-fluorophenyl)ethoxy]pyridin-3-yl}-1H-pyrazol-1-yl)methyl]-N-methylcyclopropanecarboxamide (4-8) (R=Me, R'=H): To a reaction solution of (4-7) (1.0 eq.) with $iPr_2EtN$ (2.0 eq.) in 1.0 mL of DMF was added HATU (1.5 eq.). After stirring for 30 minutes, alkylamine (1.1 eq.) was added. The resulting mixture was stirred at room temperature for overnight. The reaction mixture was partitioned between EtOAc (200 mL) and saturated $NaHCO_3$ solution (2×50 mL) and brine (50 mL). The organic layer was dried ($Na_2SO_4$) and concentrated by vacuum. The sample was free based by partitioning between EtOAc (200 mL) and saturated $NaHCO_3$ solution (50 mL) and brine (50 mL). The organic layer was dried ($Na_2SO_4$) and concentrated by vacuum. The residue was treated with 1.0 mL of $H_2O$ and lyophilized to afford (4-8).

General Procedure 62

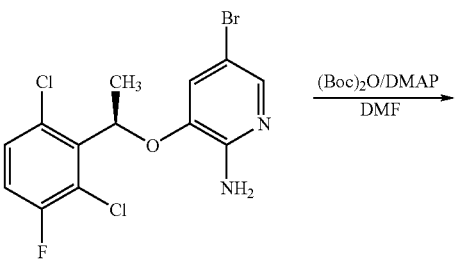

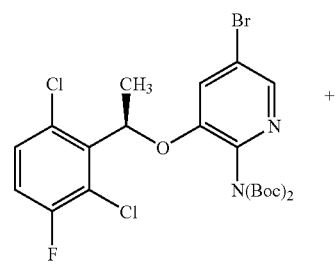

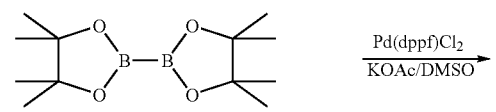

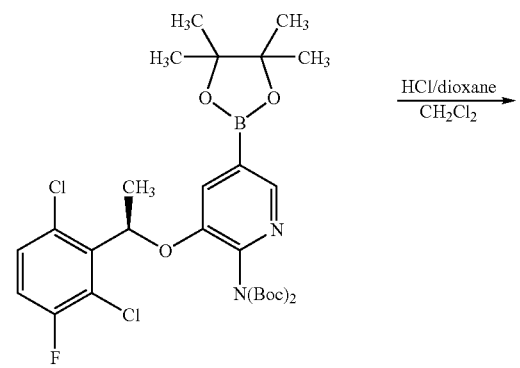

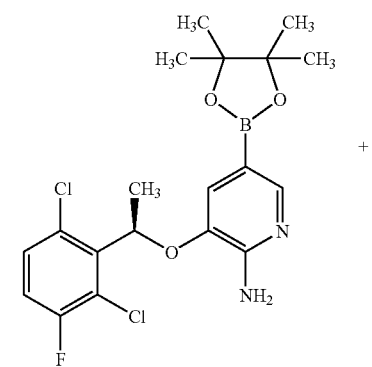

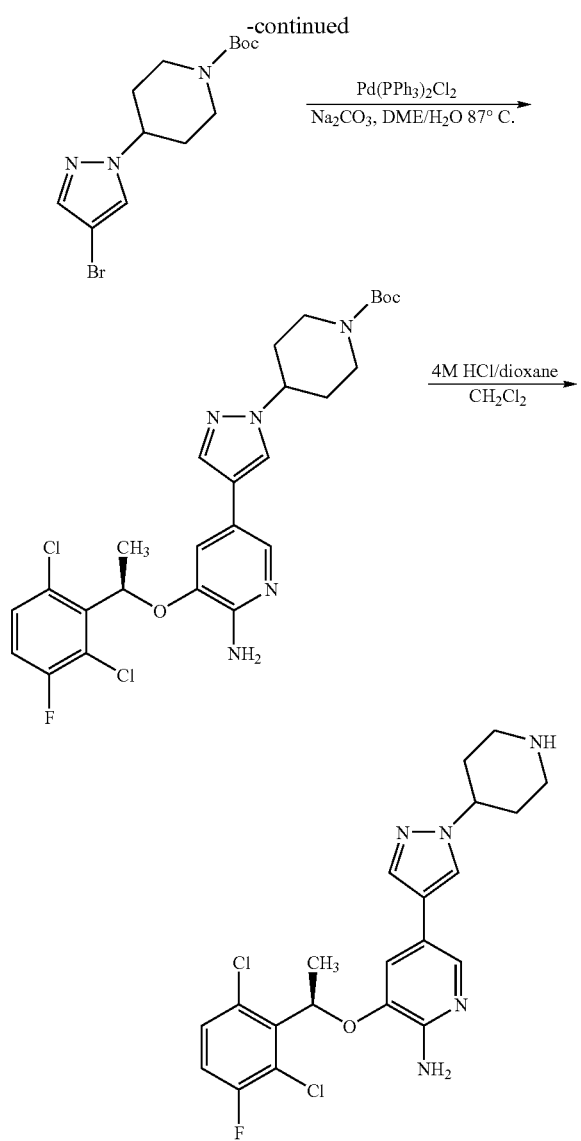

To a solution of 5-bromo-3-[(R)-1-(2,6-dichloro-3-fluoro-phenyl)-ethoxy]-pyridin-2-ylamine (12.83 g, 33.76 mmol) in anhydrous DMF (100 mL) was added di-tert-butyl dicarbonate (21.25 g, 97.35 mmol) and 4-dimethylaminopyridine (0.793 g, 6.49 mmol). The reaction was stirred at ambient temperature for 18 hours under nitrogen. To the mixture was added saturated NaHCO₃ solution (300 mL), and extracted with EtOAc (3×250 mL). The combined extracts were washed with water (5×100 mL), sat. NaHCO₃, and brine, then dried over Na₂SO₄. After filtration, evaporation, and high vacuum drying, di-boc protected 5-bromo-3-[(R)-1-(2,6-dichloro-3-fluoro-phenyl)-ethoxy]-pyridin-2-ylamine was obtained as an off-white foam solid (19.59 g, 100% yield). $^1$H NMR (DMSO-d$_6$, 400 MHz) δ 8.18 (d, 1H), 7.83 (d, 1H), 7.59 (dd, 1H), 7.48 (t, 1H), 6.25 (q, 1H), 1.75 (d, 3H), 1.39 (s, 9H), 1.19 (s, 9H).

To a solution of the di-boc protected 5-bromo-3-[(R)-1-(2,6-dichloro-3-fluoro-phenyl)-ethoxy]-pyridin-2-ylamine (19.58 g, 33.76 mmol) in DMSO (68 mL) was added potassium acetate (11.26 g, 114.78 mmol) and bis(pinacolato)diboron (10.29 g, 40.51 mmol). The mixture was degassed and charged with nitrogen three times, then Pd(dppf)Cl₂·CH₂Cl₂ (1.38 g, 1.69 mmol) was added. The reaction mixture was degassed and charged with nitrogen three times, and then stirred at 80° C. oil bath under nitrogen for 12 hours. The reaction was cooled to ambient temperature, diluted with ethyl acetate (100 mL), and filtered through a celite pad which was washed with ethyl acetate. The combined ethyl acetate solution (700 mL) was washed with water (5×100 mL), brine (100 mL), and dried over Na₂SO₄. After filtration and concentration, the residue was purified on a silica gel column eluting with EtOAc/Hexane (0%-50%) to provide di-boc protected 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine as a foam sold (20.59 g, 97% yield). $^1$H NMR (DMSO-d$_6$, 400 MHz) δ 8.20 (d, 1H), 7.70 (d, 1H), 7.63 (dd, 1H), 7.47 (t, 1H), 6.20 (q, 1H), 1.73 (d, 3H), 1.50-1.13 (m, 30H).

To a solution of di-boc protected 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (20.34 g, 32.42 mmol) in CH₂Cl₂ (80 mL) was added a solution of dry HCl in dioxane (4N, 40.5 mL, 162 mmol). The reaction solution was stirred at 40° C. oil bath under nitrogen for 12 hours. The reaction mixture was cooled to ambient temperature, diluted with EtOAc (400 mL), then washed carefully but quickly with saturated NaHCO₃ until the water layer was basic (pH>8). The organic layer was washed with brine, and dried over Na₂SO₄. After filtration, evaporation, and high vacuum drying, 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine was obtained as an off-white foam solid (13.48 g, 97% yield). $^1$H NMR (DMSO-d$_6$, 400 MHz) δ 8.01 (d, 1H), 7.27 (dd, 1H), 7.17 (d, 1H), 7.03 (t, 1H), 6.12 (q, 1H), 5.08 (bs, 2H), 1.81 (d, 3H), 1.30 (s, 6H), 1.28 (s, 6H).

To a stirred solution of 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (4.2711 g, 10.0 mmol) and 4-(4-bromo-pyrazol-1-yl)-piperidine-1-carboxylic acid tert-butyl ester (see procedure 11) (3.9628 g, 12.0 mmol) in DME (40 mL) was added a solution of Na₂CO₃ (3.1787 g, 30.0 mmol) in water (10 mL). The solution was degassed and charged with nitrogen three times. To the solution was added Pd(PPh₃)₂Cl₂ (351 mg, 0.50 mmol). The reaction solution was degassed and charged with nitrogen again three times. The reaction solution was stirred at 87° C. oil bath for about 16 hours (or until consumption of the borane pinacol ester), cooled to ambient temperature and diluted with EtOAc (200 mL). The reaction mixture was filtered through a pad of celite and washed with EtOAc. The EtOAc solution was washed with brine, dried over Na₂SO₄, and concentrated. The crude product was purified on a silica gel column eluting with EtOAc/hexane system (0% EtOAc to 100% EtOAc) to afford 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (3.4167 g, 65% yield, ~95% purity) with a Rf of 0.15 (50% EtOAc/Hexanes). MS m/e 550 (M+1)⁺.

To a solution of 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (566.7 mg, 1.03 mmol) in methanol (5 mL) or dichloromethane (30 mL) was added 4N HCl/dioxane (15 mL). The solution was stirred for about 1 hour or until the de-protection was complete. The solvents were evaporated and the residue was dissolved in methanol and purified on a reversed phase C-18 preparative HPLC eluting with acetonitrile/water with 0.1% acetic acid from 5% to 30% with a linear gradient. After lyophilization, 3-[(R)-1-

(2,6-dichloro-3-fluoro-phenyl)-ethoxy]-5-(1-piperidin-4-yl-1H-pyrazol-4-yl)-pyridin-2-ylamine acetate was obtained as a white solid (410 mg, 78% yield, 100% HPLC purity, 96.4% ee). $^1$H NMR (DMSO-$d_6$, 400 MHz) δ 7.84 (s, 1H), 7.68 (d, 1H), 7.50 (dd, 1H), 7.46 (s, 1H), 7.37 (t, 1H), 6.83 (d, 1H), 6.02 (q, 1H), 5.57 (bs, 2H), 4.09 (m, 1H), 2.98 (m, 2H), 2.53 (m, 2H), 1.88 (m, 2H), 1.82 (s, 3H), 1.73 (d, 3H), 1.70 (m, 2H). MS m/e 450 (M+1)$^+$.

General Procedure 63

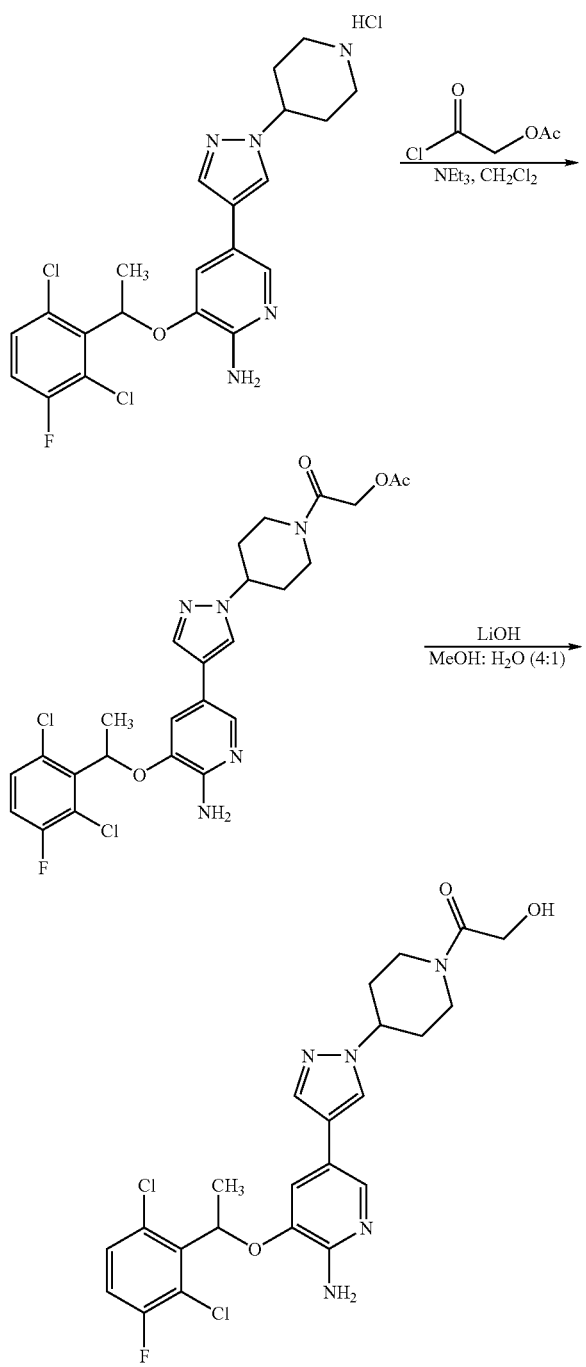

To a suspension of 3-[1-(2,6-Dichloro-3-fluoro-phenyl)-ethoxy]-5-(1-piperidin-4-yl-1H-pyrazol-4-yl)-pyridin-2-ylamine as the HCl salt (procedure 6) (150 mg, 0.288 mmol) in $CH_2Cl_2$ (2 mL) was added $NEt_3$ (0.121 mL, 0.863 mmol) and stirred for 30 minutes at room temperature. The reaction was cooled to 0° C. and acetic acid chlorocarbonylmethyl ester was added and stirred for 1 hour at room temperature. The reaction was monitored by LC-MS and after complete conversion to the desired product, water (2 mL) was added. The reaction was extracted with EtOAc (4×10 mL), dried over $Na_2SO_4$, and concentrated to give quantitative yield of acetic acid 2-[4-(4-{6-amino-5-[1-(2,6-dichloro-3-fluoro-phenyl)-ethoxy]-pyridin-3-yl}-pyrazol-1-yl)-piperidin-1-yl]-2-oxo-ethyl ester (164 mg, quant).

To solution of acetic acid 2-[4-(4-{6-amino-5-[1-(2,6-dichloro-3-fluoro-phenyl)-ethoxy]-pyridin-3-yl}-pyrazol-1-yl)-piperidin-1-yl]-2-oxo-ethyl ester (164 mg, 0.298 mmol) in MeOH (4 mL) was added LiOH (7 mg, 0.298 mmol) dissolved in 1 mL of water. The reaction was stirred for 30 minutes at room temperature in which LC-MS showed complete conversion to the 1-[4-(4-{6-amino-5-[1-(2,6-dichloro-3-fluoro-phenyl)-ethoxy]-pyridin-3-yl}-pyrazol-1-yl)-piperidin-1-yl]-2-hydroxy-ethanone. The product was purified on a reversed phase C-18 preparative HPLC eluting with acetonitrile/water having 0.1% acetic acid from 10% to 40%.

General Procedure 64

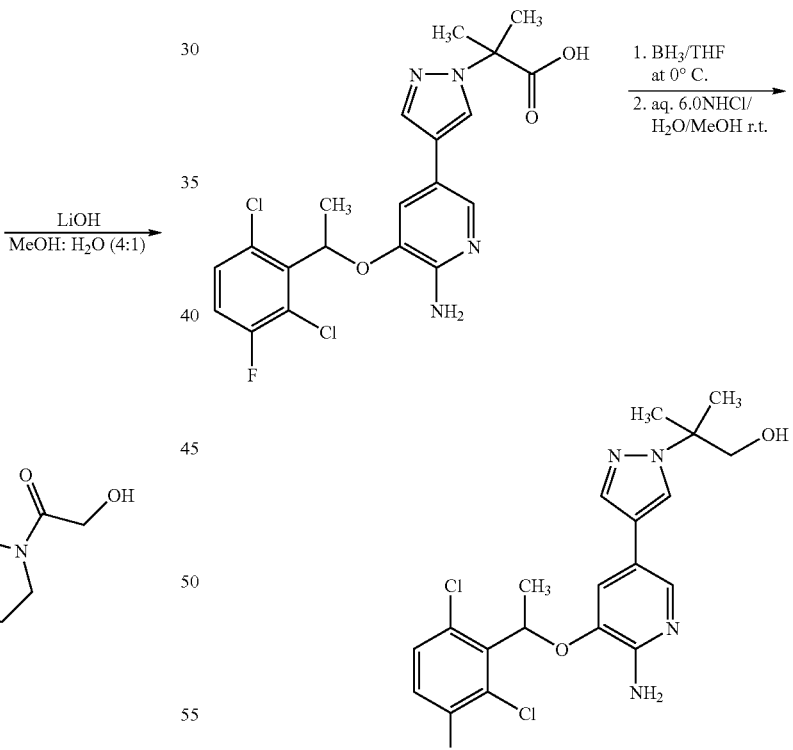

A 100 mL of flask with a stir bar was dried in an oven and cooled in a dry nitrogen atmosphere. The flask was equipped with a rubber syringe cap. The flask was immersed in an ice-water bath under nitrogen, and 1.6 mL (1.6 mmol) of 1.0 M borane solution in THF was introduced. Then 2-(4-{5-Amino-6-[1-(2,6-dichloro-3-fluoro-phenyl)-ethoxy]-pyrazin-2-yl}-pyrazol-1-yl)-2-methyl-propionic acid (procedure 5) (0.1 g, 0.221 mmol) in anhydrous THF (1.0 mL) was introduced. The resulting mixture was stirred at ambient temperature under nitrogen for 5 hours, and 6 N HCl (1.1 mL) was added slowly, and then H₂O (1.1 mL) and MeOH (7.4 mL) were introduced. The reaction mixture was stirred continually overnight. Most of solvents were evaporated in vacuo, and then a 1 N NaOH solution was used to adjust pH to 11. Water was added, and the solution was extracted with EtOAc (3×30 mL) and dried over Na₂SO₄. After filtration and concentration, the crude product was purified with a reverse phase preparative HPLC eluting with acetonitrile/water containing 0.1% acetic acid from 10% to 60%. After lyophilization of the pure fractions, 2-(4-{6-amino-5-[1-(2,6-dichloro-3-fluoro-phenyl)-ethoxy]-pyridin-3-yl}-pyrazol-1-yl)-2-methyl-propan-1-ol acetate was obtained as a white solid (21 mg, 22% yield).

General Procedure 65

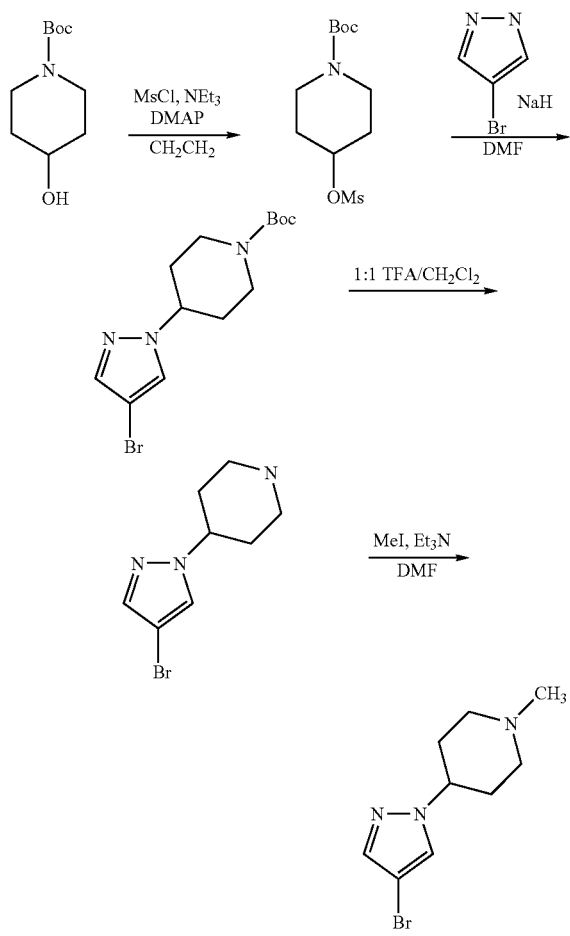

To a stirred solution of 4-hydroxy-piperidine-1-carboxylic acid tert-butyl ester (7.94 g, 39.45 mmol) in CH₂Cl₂ (100 mL), cooled to 0° C., was slowly added NEt₃ (5.54 mL, 39.45 mmol) followed by methane sulfonyl chloride (3.06 mL, 39.45 mmol) and DMAP (48 mg, 0.39 mmol). The mixture was stirred at room temperature overnight. To the mixture was added water (30 mL). Extraction with CH₂Cl₂ (3×30 mL) followed by drying (Na₂SO₄) and removal of the solvent in vacuo afforded 4-methanesulfonyloxy-piperidine-1-carboxylic acid tert-butyl ester as a white solid (11.00 g, >99% yield). ¹H NMR (CDCl₃, 400 MHz) δ 4.89 (m, 1H), 3.69 (m, 2H), 3.31 (m, 2H), 3.04 (s, 3H), 1.95 (m, 2H), 1.83 (m, 2H), 1.46 (s, 9H).

To a stirred solution of 4-bromo-pyrazole (10.44 g, 71.03 mmol) in anhydrous DMF (96 mL), cooled to 0° C., was slowly added NaH (60% in mineral oil) (3.13 g, 78.133 mmol). The solution was stirred for 1 hour at 0° C. 4-Methanesulfonyloxy-piperidine-1-carboxylic acid tert-butyl ester (19.82 g, 71.03 mmol) was added slowly and the reaction was heated to 100° C. overnight or until consumption of the pyrazole by NMR. The reaction was cooled to room temperature and water added (20 mL) followed by extraction with EtOAc. The combined extracts were washed with saturated aqueous NaCl (4×20 mL), dried with Na₂SO₄ and concentrated to afford 4-(4-bromo-pyrazol-1-yl)-piperidine-1-carboxylic acid tert-butyl ester as an orange oil. The oil was purified using silica gel chromatography eluting with 10% EtOAc/hexanes to 25% EtOAc/hexanes to provide 4-(4-bromo-pyrazol-1-yl)-piperidine-1-carboxylic acid tert-butyl ester as a white solid (10.55 g, 45% yield) with a R_f=0.4 (25% EtOAc/hexanes, using iodine as the stain). ¹H NMR (CDCl₃, 400 MHz) δ 7.46 (s, 1H), 7.43 (s, 1H), 4.23 (m, 3H), 2.88 (m, 2H), 2.10 (m, 2H), 1.88 (m, 2H), 1.47 (s, 9H).

To a solution of 4-(4-bromo-pyrazol-1-yl)-piperidine-1-carboxylic acid tert-butyl ester (500 mg, 1.515 mmol) in CH₂Cl₂ (3 mL) was added TFA (3 mL). The reaction was stirred at room temperature until LCMS indicated completion of the reaction. The solvents were removed in vacuo, and the residue was dissolved in MeOH (15 mL). The pH of the solution was adjusted to 9 with hydroxide resin to afford 4-(4-bromo-pyrazol-1-yl)-piperidine.

To a solution of 4-(4-bromo-pyrazol-1-yl)-piperidine (375 mg, 1.63 mmol) in DMF (3.26 mL) was added NEt₃ (230 µL, 1.63 mmol) and stirred for 5 minutes. Methyliodide (MeI) (1.63 mL, 1M MeI in DMF, freshly made) was added and the reaction was stirred overnight at room temperature. Water was added and the solution was extracted with EtOAc (4×10 mL). The organic solution was washed with brine, dried with Na₂SO₄, concentrated, and dried in vacuo to afford 4-(4-bromo-pyrazol-1-yl)-1-methyl-piperidine (251 mg, 63% yield).

General Procedure 66

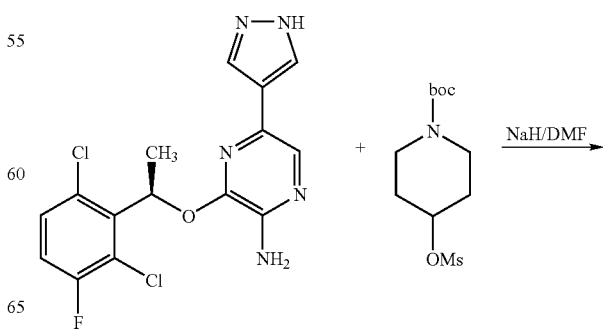

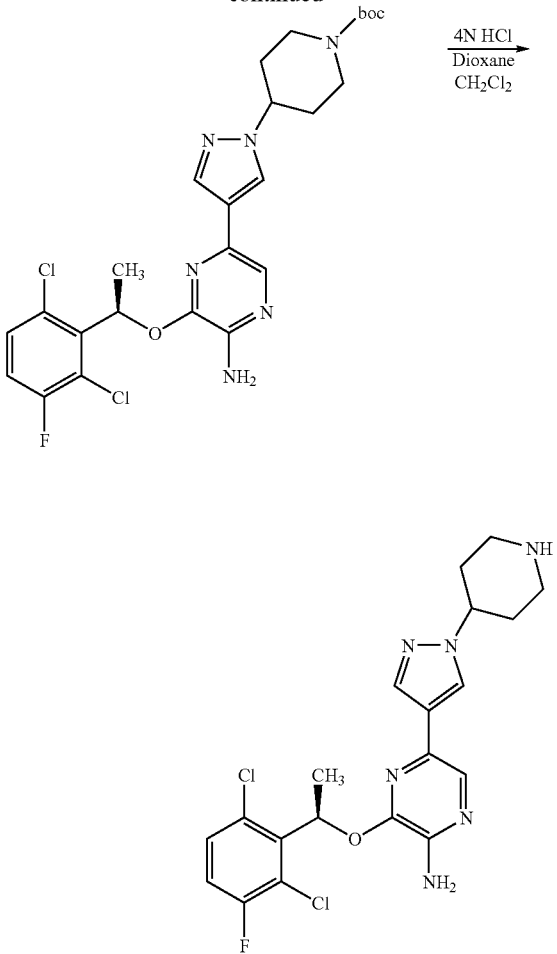

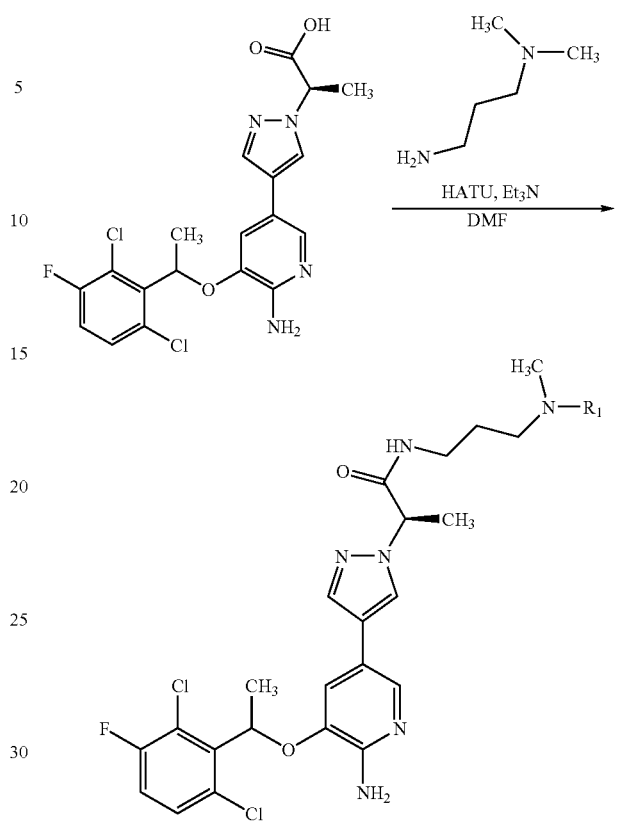

To a solution of 3-[(R)-1-(2,6-dichloro-3-fluoro-phenyl)-ethoxy]-5-(1H-pyrazol-4-yl)-pyrazin-2-ylamine (295 mg, 0.80 mmol) in anhydrous DMF (4 mL) was added NaH (60% in mineral oil, 30.7 mg, 0.80 mmol). The mixture was stirred at ambient temperature under nitrogen for 0.5 h, and then 4-methanesulfonyloxy-piperidine-1-carboxylic acid tert-butyl ester (223.5 mg, 0.80 mmol) was introduced. The reaction mixture was heated to 90° C. oil bath for 0.5 h under nitrogen, and cooled to ambient temperature. Water was added slowly to the mixture, which was extracted with EtOAc, washed with brine, and dried over $Na_2SO_4$. The crude product was purified on a silica gel column to provide 4-(4-{5-amino-6-[(R)-1-(2,6-dichloro-3-fluoro-phenyl)-ethoxy]-pyrazin-2-yl}-pyrazol-1-yl)-piperidine-1-carboxylic acid tert-butyl ester as a white solid (265 mg, 59% yield).

To a solution of 4-(4-{5-amino-6-[1-(2,6-dichloro-3-fluoro-phenyl)-ethoxy]-pyrazin-2-yl}-pyrazol-1-yl)-piperidine-1-carboxylic acid tert-butyl ester (265 mg, 0.48 mmol) in $CH_2Cl_2$ was added 4N HCl/dioxane (4 mL). The mixture was stirred at ambient temperature for one hour. After evaporation, the residue was dissolved in methanol (2.5 mL), and was purified on a reverse phase C-18 reparative HPLC eluting with acetonitrile/water containing 0.1% acetic acid with a linear gradient of 10%-40%. After lyophilization, 3-[(R)-1-(2,6-dichloro-3-fluoro-phenyl)-ethoxy]-5-(1-piperidin-4-yl-1H-pyrazol-4-yl)-pyrazin-2-ylamine acetate was obtained as a white solid (125 mg, 51% yield).

General Procedure 67

O-(7-azabenzotriazol-1-yl)-N,N, N',N'-tetramethyluronium phosphorus pentafluoride (HATU) (66 mg, 0.17 mmol) was added to a solution of 2-(4-{6-Amino-5-[1-(2,6-dichloro-3-fluoro-phenyl)-ethoxy]-pyridin-3-yl}-pyrazol-1-yl)-propionic acid (69 mg, 0.16 mmol), triethylamine (0.024 mL, 0.17 mmol) and 3-dimethylamino-propylamine (0.022 mL, 0.17 mmol) in 1.6 mL of DMF. After stirring for 3 hours, the reaction was concentrated by rotary evaporation. The residue was purified by silica gel chromatography using gradient elution of dichloromethane, methanol, ammonium hydroxide to afford 2-(4-{6-Amino-5-[1-(2,6-dichloro-3-fluoro-phenyl)-ethoxy]-pyridin-3-yl}-pyrazol-1-yl)-N-(3-dimethylamino-propyl)-propionamide. (41 mg, 50%).

General Procedure 68

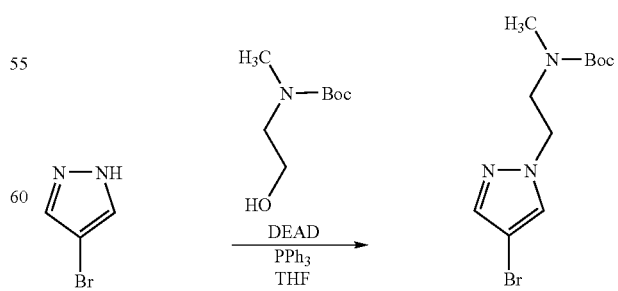

Diethylazodicarboxylate (0.48 mL, 3.1 mmol) was added to a 0° C. solution of triphenylphosphine (0.80 g, 3.1 mmol)

in THF (20 mL). After stirring for 5 minutes, 4-bromopyrazole (0.30 mg, 2.0 mmol) was added. After another 5 minutes of stirring, (2-hydroxyethyl)-methyl-carbamic acid tert-butyl ester (0.45 g, 2.6 mmol) was added. The reaction was allowed to warm to room temperature and stir overnight. The reaction was cooled to 0° C. and filtered. The filtrate was concentrated by rotary evaporation. The residue was purified by silica gel chromatography using gradient elution of dichloromethane, ethyl acetate to afford [2-(4-bromo-pyrazol-1-yl)-ethyl]-methyl-carbamic acid tert-butyl ester (541 mg, 87%).

General Procedure 69

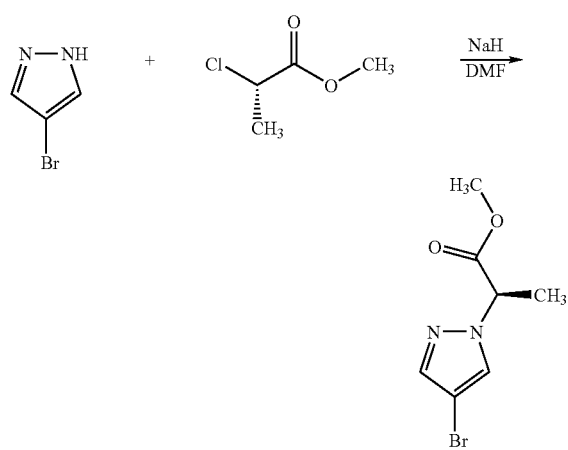

Sodium hydride (0.12 g, 4.9 mmol) was added to a solution of 4-bromo-4H-pyrazole (0.60 g, 4.1 mmol) in DMF (10 mL). After stirring for 10 minutes, a solution of 2-chloro-propionic acid methyl ester in DMF (4 mL) was added. After stirring for 4 hours, the reaction was partitioned between ethyl acetate and water. The phases were separated and the aqueous phase was extracted with ethyl acetate. The combined organic phases were dried over MgSO$_4$ and concentrated by rotary evaporation. The residue was purified by silica gel chromatography using gradient elution of ethyl acetate and hexanes to afford 2-(4-bromo-pyrazol-1-yl)-propionic acid methyl ester (733 mg, 77%).

General Procedure 70

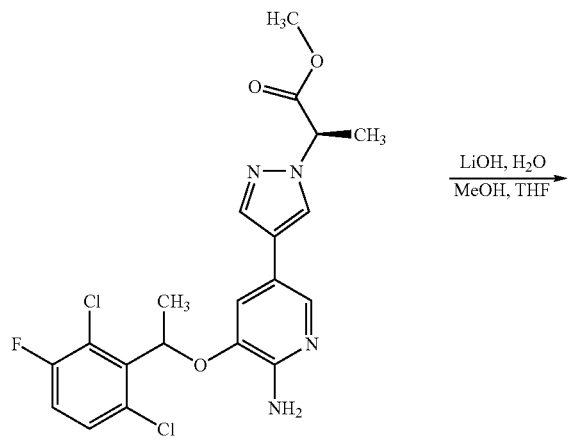

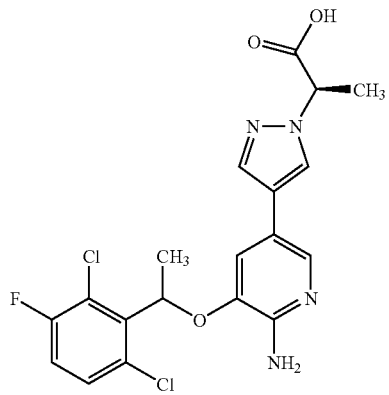

A solution of LiOH (34 mg, 1.4 mmol) in water (0.4 mL) was added to a solution of 2-(4-{6-Amino-5-[1-(2,6-dichloro-3-fluoro-phenyl)-ethoxy]-pyridin-3-yl}-pyrazol-1-yl)-propionic acid methyl ester (70 mg, 0.15 mmol) in a mixture THF (1.5 mL) and MeOH (0.4 mL). After stirring overnight, the reaction was partitioned between dichloromethane and half-saturated brine. A small amount of ethanol was added and the pH was adjusted to 7 with 1 M HCl. The phases were separated and the aqueous phase was extracted with dichloromethane. The combined organic phases were dried over Na$_2$SO$_4$, filtered and concentrated by rotary evaporation to give 2-(4-{6-amino-5-[1-(2,6-dichloro-3-fluoro-phenyl)-ethoxy]-pyridin-3-yl}-pyrazol-1-yl)-propionic acid (69 mg, 100%).

General Procedure 71

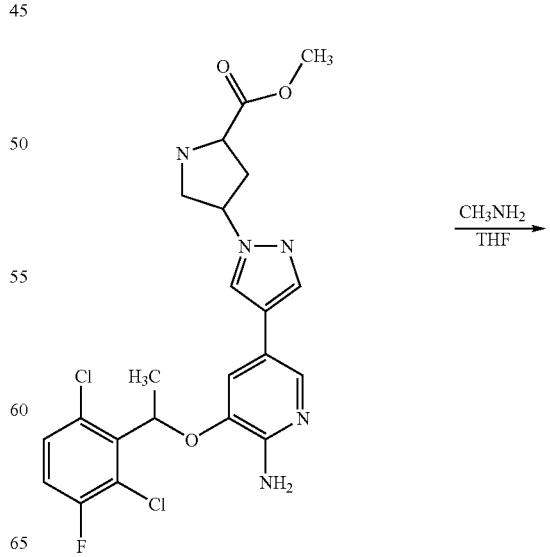

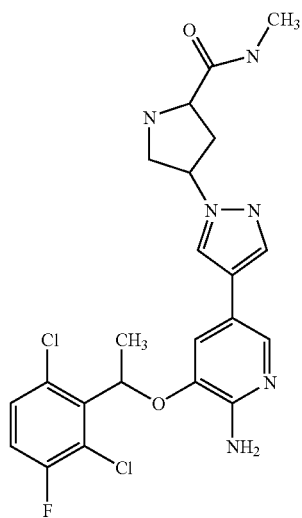

To a stirred solution of 4-(3-{6-Amino-5-[1-(2,6-dichloro-3-fluoro-phenyl)-ethoxy]-pyridin-3-yl}-pyrazol-1-yl)-pyrrolidine-2-carboxylic acid methyl ester (105 mg, 0.21 mmol) in THF (5 mL) was added 2 M $CH_3NH_2$ in THF (1.06 mL, 2.12 mmol), the mixture was stirred and heated at 55° C. for 18 hours, LCMS checked that the reaction was completed, remove THF, the residue was purified by prep-HPLC to leave 4-(4-{6-amino-5-[1-(2,6-dichloro-3-fluoro-phenyl)-ethoxy]-pyridin-3-yl}-pyrazol-1-yl)-pyrrolidine-2-carboxylic acid methylamide (30 mg), yield 28.6%.

General Procedure 72

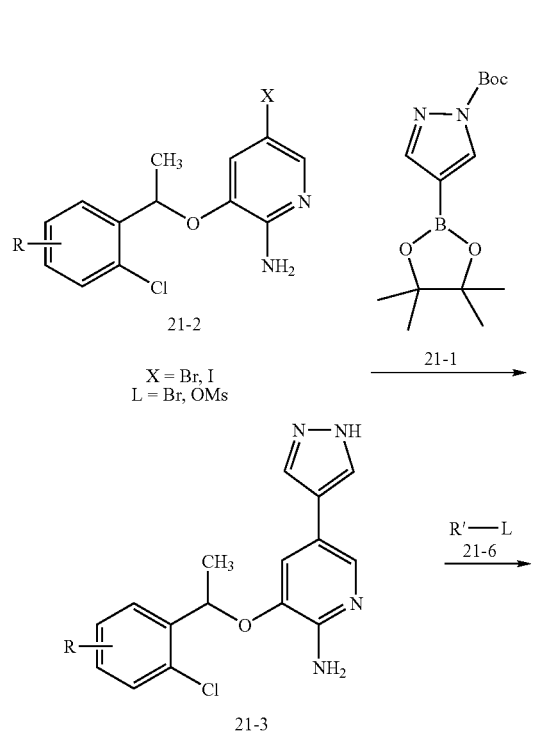

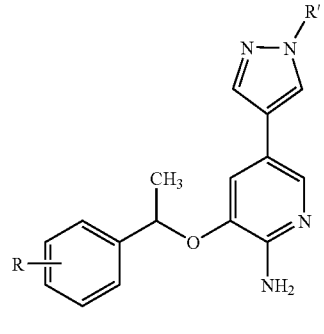

tert-butyl 4-(4,4,5,5-tetramethyl-1,3,2-dioxaborolan-2-yl)-1H-pyrazole-1-carboxylate (21-1): Di-tert-butyl dicarbonate (7.2 molar equivalent), 4-(dimethylamino)pyridine (0.84 molar equivalent) were added to a solution of 4,4,5,5-tetramethyl-2-(1H-pyrazole-4-yl)-1,3,2-dioxaborolane (6 mmol) in 40 mL of DMF. The reaction mixture was stirred at room temperature for 12 h. Water was added to the reaction mixture to quench the reaction. EtOAc was then added to extract the aqueous solution. Dry EtOAc layer over $Na_2SO_4$. The $Na_2SO_4$ was filtered off and the filtrate was evaporated to give a brown yellow oil residue as compound 21-1 (1.32 g; 4.56 mmol; 76%). $^1$H NMR (400 MHz, chloroform-D) δ ppm 1.32 (s, 12H) 1.63 (s, 9H) 7.91 (s, 1H) 8.37 (s, 1H). The residue was used for the next step reaction without further purification.

Compound 21-3, shown with the specific example of 3-[1-(2,6-dichloro-3-fluorophenyl)ethoxy]-5-(1H-pyrazol-4-yl)pyridin-2-amine (21-3a):

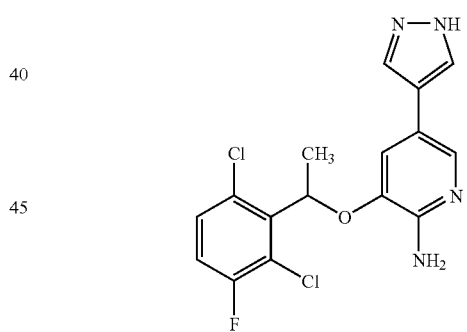

Compound 21-1 (1.0 molar equivalent) was added to a solution of compound 21-2a (Compound 21-2, with R substituents to give 2,6-dichloro-3-fluorophenyl) (1.92 mmol) in 20 mL of DME. The mixture was stirred at room temperature under a nitrogen atmosphere for 30 minutes and then dichlorobis(triphenylphosphino) palladium (II) (0.05 molar equivalent) was added. Sodium carbonate (3 molar equivalent) in 4 mL of $H_2O$ was added to the reaction mixture and the resulting solution was heated to 85° C. for 12 h. Alternative bases used were CsF and $Cs_2CO_3$ in with 1 or 2 equivalents of boronic ester, and at room temperature (CsF) or 80° C. (all). Water was added to the reaction mixture to quench the reaction. EtOAc (150 mL×2) was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with eluting with 0→10% MeOH in ethyl acetate) to give the desired product, compound 21-3a (2.05 g, 53.6% yield). ¹H NMR (400 MHz, chloroform-D) δ ppm 1.60 (s, 1H) 1.84 (d, J=6.57 Hz, 3H) 5.07 (s, 2H) 6.06 (q, J=6.57 Hz, 1H) 6.89 (d, J=1.77 Hz, 1H) 6.96-7.06 (m, 1H) 7.22-7.33 (m, 1H) 7.67 (s, 2H) 7.80 (d, J=1.52 Hz, 1H).

To make compounds of formula 21-4, the following exemplary procedure can be used: sodium hydride (1.2 molar equivalent) is added to a solution of compound 21-3 (0.87 mmol) in 10 mL of DMF. The mixture is stirred at room temperature under a nitrogen atmosphere for 30 min and then compound 21-6 (1 molar equivalent) is added. The resulting solution is heated to 85-90° C. for 12 h. Water (20 mL) is added to the reaction mixture to quench the reaction. EtOAc (50 mL×2) is then added to extract the aqueous solution. Dry EtOAc layer over Na₂SO₄. The Na₂SO₄ is filtered off and the filtrate is evaporated. The residue is purified by silica gel chromatography (eluting with EtOAc in hexanes) to give the desired product, compound 21-4 (20-50% yield).

General Procedure 73

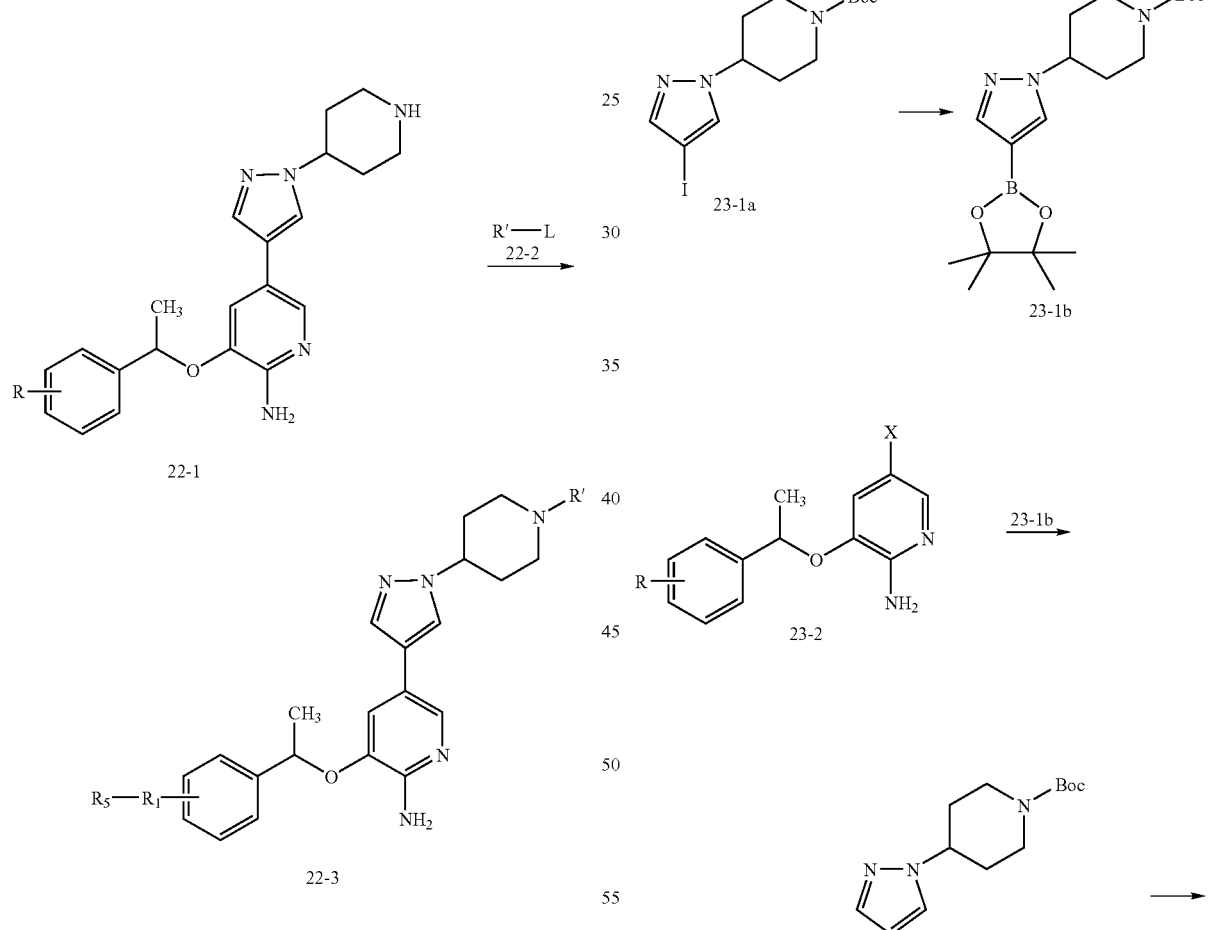

L=Br, Cl, COOH, COCl, OMs, ethylene carbonate, aldehyde

Compounds of formula 22-3 can be prepared by the following exemplary procedure: Compound 22-2 (1.2 molar equivalent) is added to a solution of compound 22-1 (0.24 mmol) and base (3-5 molar equivalent) and/or coupling reagent (1 molar equivalent) in 5 mL of DMF. The mixture is stirred under a nitrogen atmosphere for 12 h. Water (20 mL) is added to the reaction mixture to quench the reaction. EtOAc (50 mL×2) is then added to extract the aqueous solution. Dry EtOAc layer over Na₂SO₄. The Na₂SO₄ is filtered off and the filtrate evaporated. The residue is purified by silica gel chromatography (eluting with CH₃OH, CH₂Cl₂, EtOAc, and hexanes) to give the desired product, compound 22-3.

General Procedure 74

The following procedure can be used to prepare piperidine-pyrazole-2-aminopyridine derivatives.

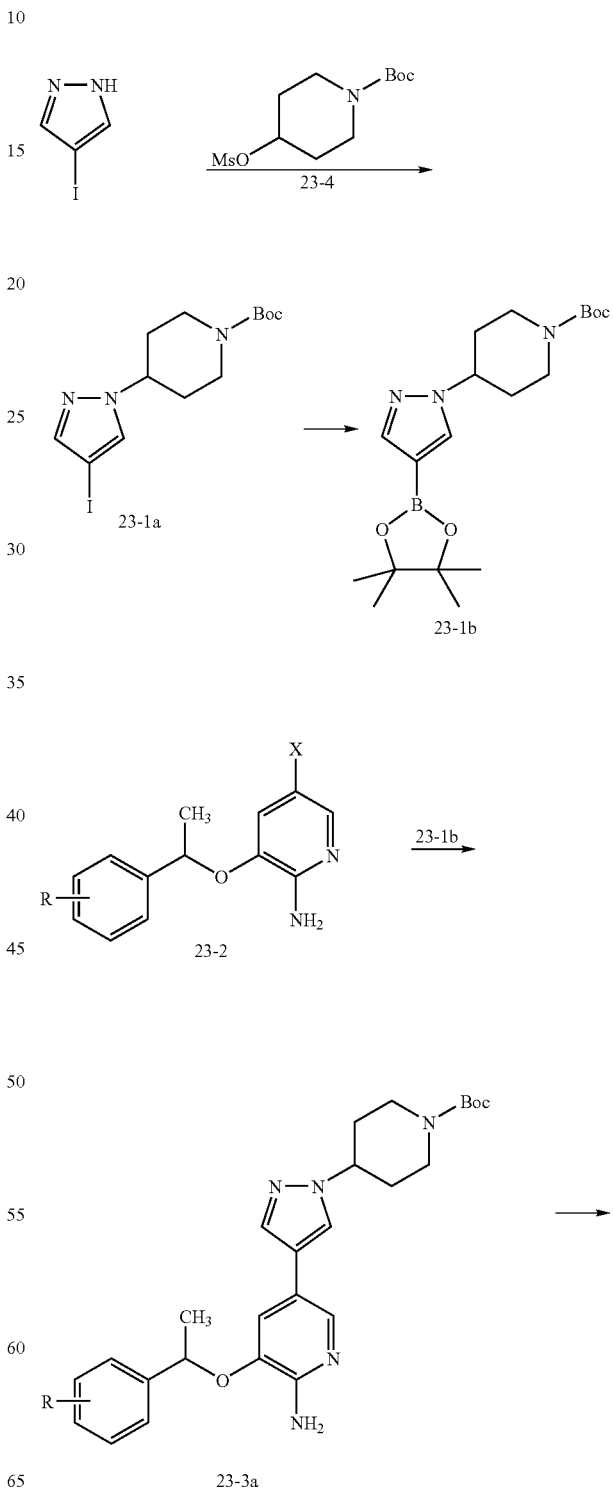

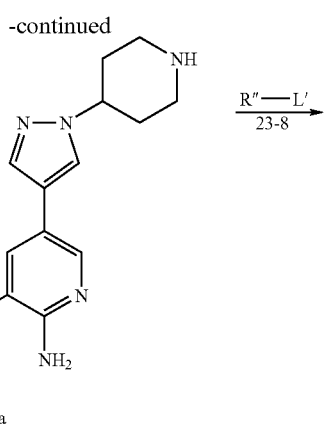

23-5a

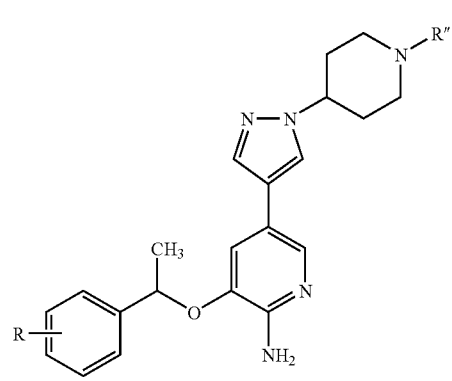

23-7a

L' = Br, Cl, COOH, COCl, OMs, ethylene carbonate, aldehyde tert-butyl 4-(4-iodo-1H-pyrazol-1-yl)piperidine-1-carboxylate (23-1a)

NaH (1.2 eq., 0.68 mmol) was added portionwise to a stirred solution of 4-iodopyrazole (0.57 mmol) in DMF (2 L) at 4° C. The resulting mixture was stirred for 1 hour at 4° C. and compound 23-4 (1.1 eq., 0.63 mmol) was then added. The resulting mixture was heated to 100° C. for 12 h. The reaction was quenched with $H_2O$ and extracted with EtOAc several times. The combined organic layers were dried, filtered, and concentrated to afford an orange oil. The residue was purified by silica gel chromatography (eluting with 5% EtOAc in pentane) to give compound 23-1a as a white solid (140 g, 66%).

tert-butyl-4-[4-(4,4,5,5-tetramethyl-1,3,2-dioxaborolan-2-yl)-1H-pyrazol-1-yl]piperidine-1-carboxylate (23-1b)

Bis(pinacolato)diboron (1.4 eq., 134 g, 0.52 mol) and potassium acetate (4 eq., 145 g, 1.48 mol) were added sequentially to a solution of compound 23-1a (140 g, 0.37 mol) in 1.5 L of DMSO. The mixture was purged with nitrogen several times and dichlorobis(triphenylphosphino) palladium (II) (0.05 eq., 12.9 g, 0.018 mol) was then added. The resulting mixture was heated at 80° C. for 2 h. The reaction mixture was cooled to room temperature and filtered through a bed of celite and washed with EtOAc. The filtrate was washed with saturated NaCl (500 mL×2), dried over $Na_2SO_4$, filtered and concentrated. The residue was purified by silica gel chromatography (eluting with 5% EtOAc in hexanes) to give compound 23-1 b as a white solid (55 g, 40%).

Compound 23-2 (1.0 molar equivalent) was added to a solution of compound 23-1b (1.3 molar equivalent) in 15 mL of DME. The mixture was purged with nitrogen several times and then dichlorobis(triphenylphosphino) palladium (II) (0.05 molar equivalent) was added. Cesium carbonate (3 molar equivalent) in 4 mL of $H_2O$ was added to the reaction mixture and the resulting solution was heated to 85° C. for 12 h. Water (10 mL) was added to the reaction mixture to quench the reaction. EtOAc (150 mL×2) was then added to extract the aqueous solution. Dry EtOAc layer over $Na_2SO_4$. The $Na_2SO_4$ was filtered off and the filtrated was evaporated to give a dark brown oil residue. The residue was purified by silica gel chromatography (eluting with eluting with 75→100% EtOAc in hexanes) to give compound 23-3a (61% yield).

Hydrochloride (19 eq., 12 mmol) was added to a solution of compound 23-3a (0.63 mmol) in MeOH (4 mL). The mixture was stirred at room temperature for 12 h. The solvent was evaporated and $H_2O$ (10 mL) was added. Saturated $NaHCO_3$ (aq) was added to neutralize the solution to pH 7. Ethyl acetate (100 mL×2) was added to extract the aqueous solution. The combined organic layer was dried over $Na_2SO_4$, filtered, and evaporated to give compound 23-5a as a solid reside (0.6 mmol, 95% yield).

Compounds of formula 23-7 can be formed according to the following general procedure: Compound 23-8 (1.2 molar equivalent) is added to a solution of compound 23-5a (0.24 mmol) and base (3-5 molar equivalent) and/or coupling reagent (1 molar equivalent) in 5 mL of DMF. The mixture is stirred under a nitrogen atmosphere for 12 h. Water (20 mL) is added to the reaction mixture to quench the reaction. EtOAc (50 mL×2) is then added to extract the aqueous solution. Dry EtOAc layer over $Na_2SO_4$. The $Na_2SO_4$ is filtered off and the filtrated is evaporated to give an oil residue. The residue is purified by silica gel chromatography (eluting with $CH_3OH$, $CH_2Cl_2$, EtOAc, and hexanes) to give the desired product, compound 23-7a.

General Procedure 75

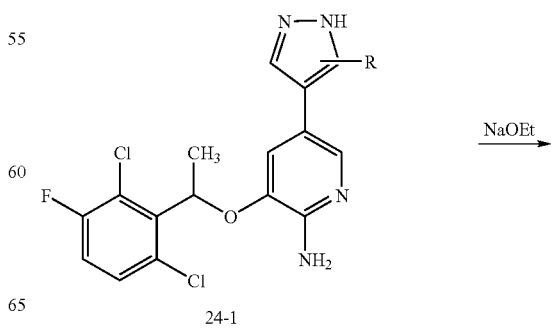

24-1

-continued

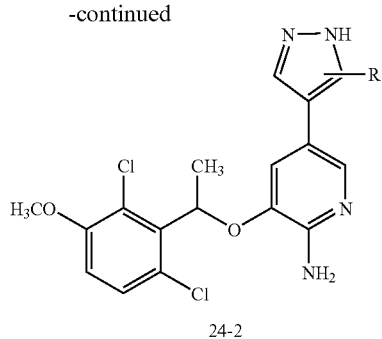

24-2

3-methoxy compounds can be prepared from the corresponding 3-fluoro compounds by the following general procedure. To 4 mL of DMSO is added 0.124 mL ethanol followed by 32 mg NaH. After stirring for 30 minutes 250 mg of 24-1 is added and the reaction heated to 40° C. After three hours the reaction is cooled and poured into water to precipitate. After neutralization to pH 6, the product 24-2 is isolated.

General Procedure 76

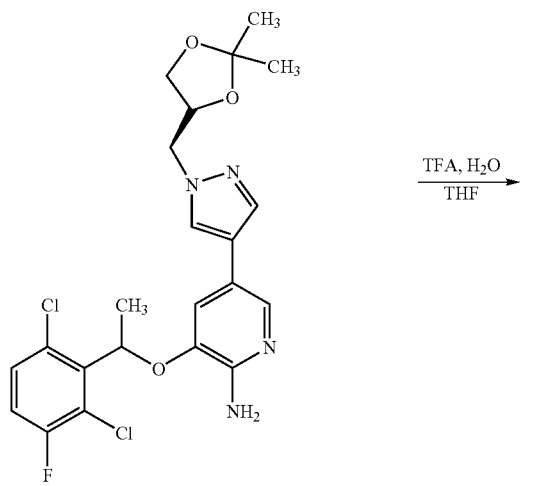

To a stirred solution of 3-[1-(2,6-dichloro-3-fluoro-phenyl)-ethoxy]-5-[1-(2,2-dimethyl-[1,3]dioxolan-4-ylmethyl)-1H-pyrazol-4-yl]-pyridin-2-ylamine (150 mg, 0.31 mmol) in THF (3 mL) and H$_2$O (2 mL) was added TFA (2 mL) at 0° C., the mixture was stirred and warmed to room temperature, then heated at 50° C. for 5 hours, LCMS checked that the reaction was completed, remove THF, the residue was purified by prep-HPLC to leave 3-(4-{6-amino-5-[1-(2,6-dichloro-3-fluoro-phenyl)-ethoxy]-pyridin-3-yl}-pyrazol-1-yl)-propane-1,2-diol (102 mg), yield 74.2%.

General Procedure 77

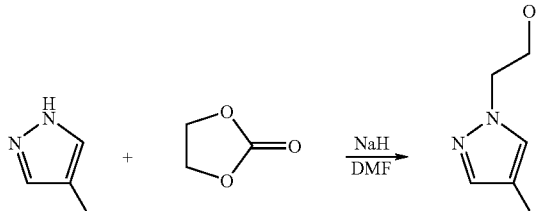

To a stirred solution of 4-bromo-1H-pyrazole in DMF was added sodium hydride at room temperature. The mixture was stirred for 30 minutes, [1,3]dioxolan-2-one was added, the mixture was stirred and slowly warmed to room temperature. The reaction was monitored by TLC. After the reaction was done, EtOAc was added, washed with saturated NaHCO$_3$, water and brine, dried with Na$_2$SO$_4$, filtered and concentrated. The residue was purified by silica gel, eluants EtOAc and DCM 10%, to give 2-(4-Bromo-pyrazol-1-yl)-ethanol 0.22 g, yield 34%. $^1$H NMR (400 MHz, chloroform-D) δ ppm 7.49 (s, 1H) 7.46 (s, 1H) 4.18-4.23 (m, 2H) 3.93-3.98 (m, 2H) 3.09 (s, 1H).

Example 1

5-Bromo-3-[(R)-1-(2,6-dichloro-3-fluoro-phenyl)-ethoxy]-pyrazin-2-ylamine

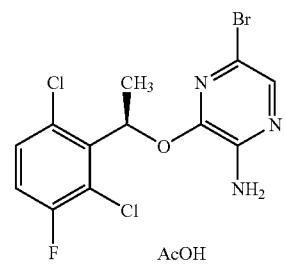

The title compound was prepared according to procedure 2, from (1S)-1-(2,6-dichloro-3-fluorophenyl)ethanol. $^1$H NMR (400 MHz, DMSO-d$_6$) δ 7.53 (s, 1H), 7.48 (m, 1H), 7.39 (t, 1H), 6.48 (s, 2H), 6.41 (q, 1H), 1.74 (d, 3H); LCMS: 381 [M+1]; c-Met Ki: 0.796 µM.

Example 2

4-{5-Amino-6-[(R)-1-(2,6-dichloro-3-fluoro-phenyl)-ethoxy]-pyrazin-2-yl}-benzoic acid

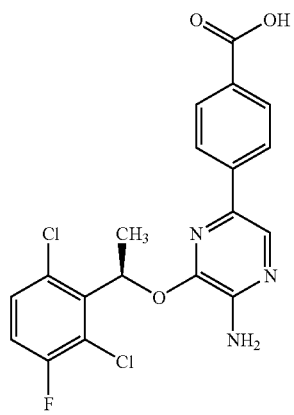

The title compound was prepared according to procedure 3. ¹H NMR (400 MHz, DMSO-d$_6$) δ 8.16 (s, 1H), 7.84 (d, 2H), 7.77 (d, 2H), 7.53 (m, 1H), 7.37 (t, 1H), 6.64 (s, 2H), 6.53 (q, 1H), 1.78 (d, 3H); LCMS: 422 [M+1]; c-Met Ki: 0.154 μM.

Example 3

(4-{5-Amino-6-[(R)-1-(2,6-dichloro-3-fluoro-phenyl)-ethoxy]-pyrazin-2-yl}-phenyl)-piperazin-1-yl-methanone

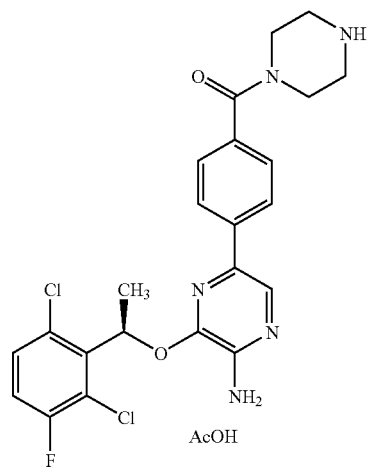

The title compound was prepared according to procedure 4. ¹H NMR (400 MHz, DMSO-d$_6$) δ 8.11 (s, 1H), 7.73 (d, 2H), 7.53 (m, 1H), 7.37 (t, 1H), 7.31 (d, 2H), 6.55 (m, 3H), 3.51 (br, 2H), 3.32 (br, 2H), 2.67 (br, 4H), 1.77 (d, 3H); LCMS: 490 [M+1]; c-Met Ki: 0.027 μM.

Example 4

4-(4-{5-Amino-6-[(R)-1-(2,6-dichloro-3-fluoro-phenyl)-ethoxy]-pyrazin-2-yl}-benzoyl)-piperazine-1-carboxylic acid tert-butyl ester

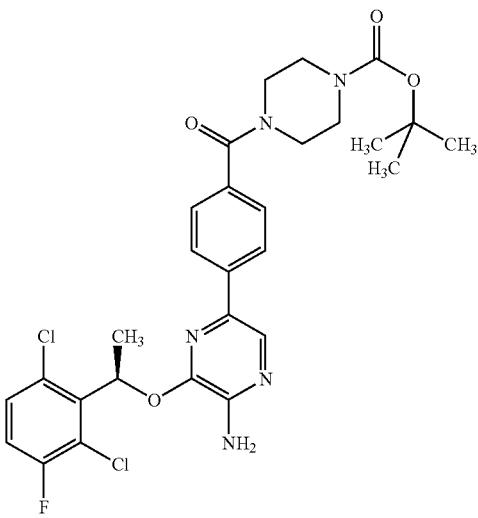

The title compound was prepared according to procedure 16 followed by 20. ¹H NMR (400 MHz, DMSO-d$_6$) δ 8.12 (s, 1H), 7.72 (d, 2H), 7.50 (m, 1H), 7.33 (t, 3H), 6.55 (m, 3H), 3.51 (br, 2H), 3.39 (m, 3H), 3.32 (br, 3H), 1.77 (d, 3H), 1.40 (s, 9H); LCMS: 590 [M+1]; c-Met Ki: 0.335 μM.

Example 5

3-[(1R)-1-(2,6-dichloro-3-fluorophenyl)ethoxy]-5-[4-(piperazin-1-ylcarbonyl)phenyl]pyridin-2-amine

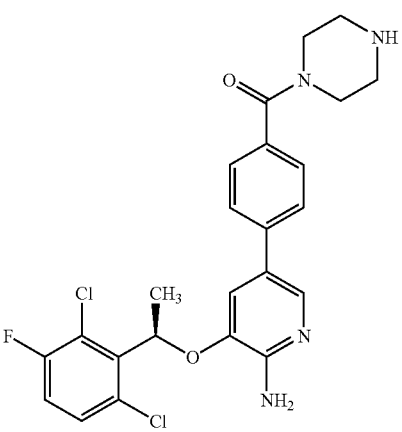

The title compound was prepared according to procedure 20 followed by 21 as a racemic mixture with the corresponding S enantiomer of Example 119, followed by separation by chiral chromatography. The title compound was also prepared as an enantiomerically pure compound starting from the chiral starting material ¹H NMR (400 MHz, DMSO-D6) δ ppm 1.83 (d, J=6.57 Hz, 3H) 3.35 (s, 4H) 3.69 (s, 4H) 6.24 (q, J=6.57 Hz, 1H) 6.91-7.08 (m, 2H) 7.10 (d, J=1.26 Hz, 1H)

7.46 (t, J=8.72 Hz, 1H) 7.50 (s, 4H) 7.58 (dd, J=8.97, 4.93 Hz, 1H) 7.91 (d, J=1.77 Hz, 1H) 9.35 (s, 2H); LCMS: 490 [M+1]; c-Met Ki: 0.01 µM.

Example 6

4-{6-amino-5-[(1R)-1-(2,6-dichloro-3-fluorophenyl)ethoxy]pyridin-3-yl}-N-[2-(dimethylamino)ethyl]-N-methylbenzamide

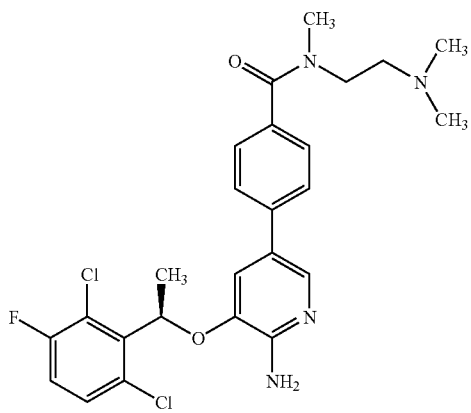

The title compound was prepared according to procedure 20. ¹H NMR (400 MHz, DMSO-D6) δ ppm 1.80 (d, J=6.82 Hz, 3H) 1.97 (s, 3H) 2.19 (s, 3H) 2.30-2.42 (m, J=1.77 Hz, 2H) 2.93 (s, 3H) 3.22-3.29 (m, 1H) 3.44-3.61 (m, 1H) 5.95 (s, 2H) 6.14 (q, J=6.57 Hz, 1H) 6.98 (d, J=1.01 Hz, 1H) 7.30-7.39 (m, 2H) 7.40-7.47 (m, 3H) 7.51-7.62 (m, 1H) 7.87 (d, J=1.77 Hz, 1H); LCMS: 506 [M+1]; c-Met Ki: 0.01 µM.

Example 7

(4-{6-amino-5-[(1R)-1-(2,6-dichloro-3-fluorophenyl)ethoxy]pyridin-3-yl}phenyl)methanol

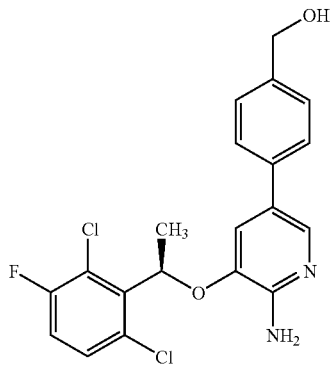

The title compound was prepared according to procedure 27. ¹H NMR (400 MHz, DMSO-D6) δ ppm 1.84 (d, J=6.57 Hz, 3H) 4.49 (d, J=5.81 Hz, 2H) 5.20 (t, J=5.81 Hz, 1H) 6.25 (q, J=6.57 Hz, 1H) 6.46-6.88 (m, 2H) 7.04 (d, J=1.52 Hz, 1H) 7.34 (s, 4H) 7.46 (t, J=8.72 Hz, 1H) 7.59 (dd, J=8.97, 4.93 Hz, 1H) 7.76 (d, J=1.52 Hz, 1H); LCMS: 408 [M+1]; c-Met Ki: 0.051 µM.

Example 8

4-{6-amino-5-[(1R)-1-(2,6-dichloro-3-fluorophenyl)ethoxy]pyridin-3-yl}-N-[3-(dimethylamino)propyl]-N-methylbenzamide

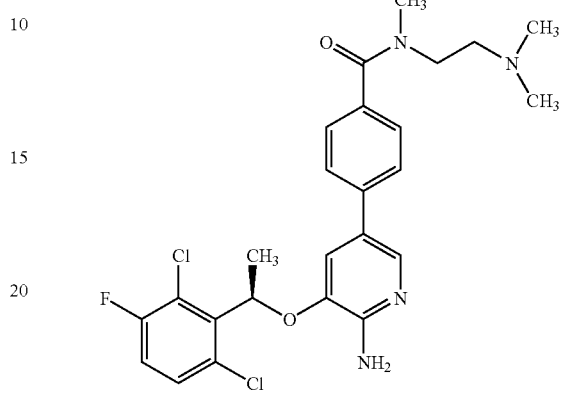

The title compound was prepared according to procedure 27. ¹H NMR (400 MHz, DMSO-D6) δ ppm 1.60-1.73 (m, 2H) 1.80 (d, J=6.57 Hz, 3H) 1.94 (s, 3H) 2.13 (s, 3H) 2.20-2.29 (m, 2H) 2.92 (s, 3H) 3.36-3.50 (m, 2H) 5.96 (s, 2H) 6.14 (q, J=6.57 Hz, 1H) 6.98 (s, 1H) 7.37 (s, 2H) 7.40-7.51 (m, 3H) 7.55 (dd, J=8.84, 4.80 Hz, 1H) 7.86 (d, J=1.77 Hz, 1H); LCMS: 520 [M+1]; c-Met Ki: 0.01 µM.

Example 9 tert-butyl 4-(4-{6-amino-5-[(1R)-1-(2,6-dichloro-3-fluorophenyl)ethoxy]pyridin-3-yl}benzoyl)piperazine-1-carboxylate

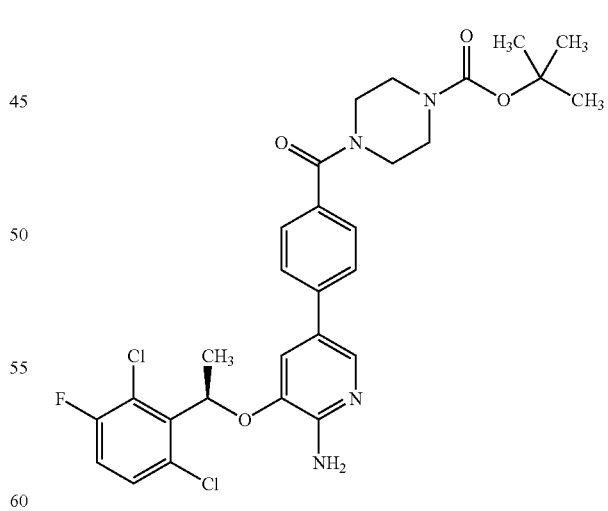

The title compound was prepared according to procedure 20. ¹H NMR (400 MHz, chloroform-D) δ ppm 1.46 (s, 9H) 1.86 (d, J=6.82 Hz, 3H) 3.30-3.89 (m, 8H) 4.90 (s, 2H) 6.11 (q, J=6.57 Hz, 1H) 6.98 (d, J=1.52 Hz, 1H) 7.01-7.10 (m, 1H) 7.30 (dd, J=8.97, 4.93 Hz, 1H) 7.35-7.43 (m, 4H) 7.88 (d, J=1.77 Hz, 1H); LCMS: 590 [M+1]; c-Met Ki: 0.03 µM.

Example 10

3-[(R)-1-(2,6-Dichloro-3-fluoro-phenyl)-ethoxy]-5-[1-(1-methyl-piperidin-4-yl)-1H-pyrazol-4-yl]-pyridin-2-ylamine

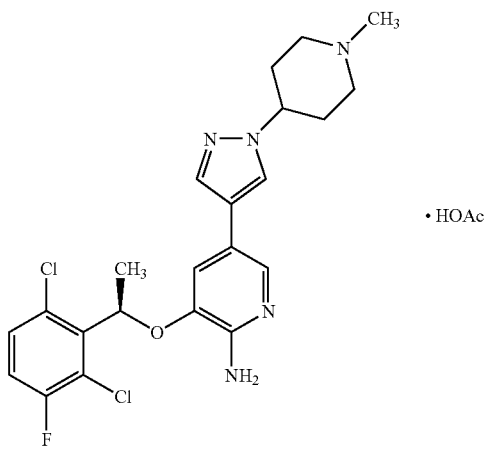

· HOAc

The title compound was prepared according to procedure 62 using 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine and 4-(4-bromo-pyrazol-1-yl)-1-methy-piperidine (prepared according to general procedure 11. $^1$H NMR (400 MHz, CDCl$_3$) δ 7.65 (s, 1H), 7.55 (s, 1H), 7.50 (s, 1H), 7.31 (m, 1H), 7.06 (m, 1H), 6.87 (s, 1H), 6.08 (m, 1H), 5.50 (bs, 2H), 4.18 (m, 1H), 3.11 (m, 2H), 2.40 (s, 3H), 2.30 (m, 2H), 2.20 (m, 4H), 2.07 (s, 3H), 1.86 (d, J=8 Hz, 3H); LCMS: 464 [M+1]; c-Met Ki: 0.01 μM.

Example 11

1-[4-(4-{6-Amino-5-[(R)-1-(2,6-dichloro-3-fluoro-phenyl)-ethoxy]-pyridin-3-yl}-pyrazol-1-yl)-piperidin-1-yl]-2-hydroxy-ethanone

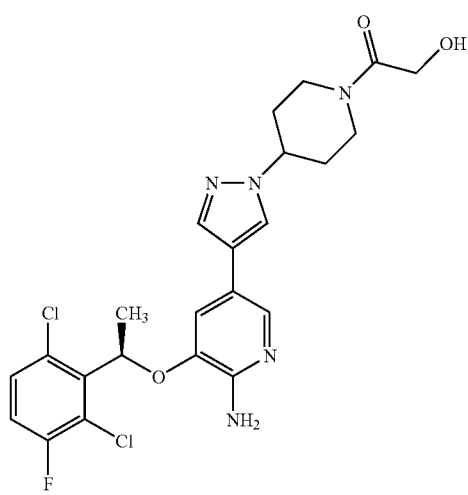

The title compound was prepared according to procedure 63. $^1$H NMR (400 MHz, CDCl$_3$) δ 7.72 (s, 1H), 7.57 (s, 1H), 7.47 (s, 1H), 7.31 (m, 1H), 7.06 (m, 1H), 6.86 (s, 1H), 6.08 (m, 1H), 5.00 (bs, 2H), 4.70 (m, 1H), 4.36 (m, 1H), 4.21 (s, 1H), 3.70 (m, 1H), 3.18 (m, 1H), 3.00 (m, 1H), 2.223 (m, 2H), 2.01 (m, 2H), 1.86 (d, J=8 Hz, 3H); LCMS: 508 [M+1]; c-Met Ki: 0.004 μM.

Example 12

3-[(R)-1-(2,6-Dichloro-3-fluoro-phenyl)-ethoxy]-5-(1-piperidin-4-yl-1H-pyrazol-4-yl)-pyridin-2-ylamine

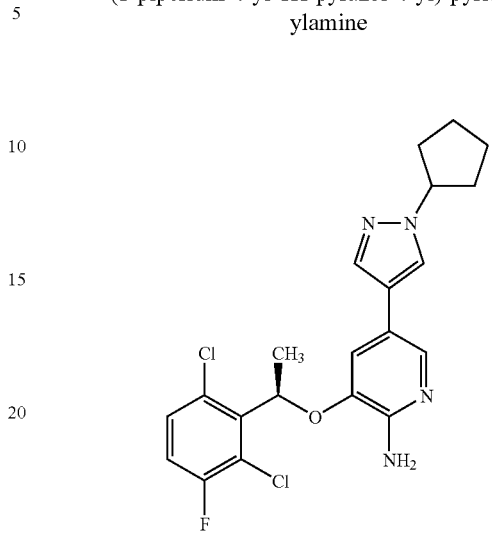

The title compound was prepared according to procedure 62 using 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine and 4-(4-bromo-pyrazol-1-yl)-1-cyclopentyl-piperidine (prepared according to general procedure 11 using bromocyclopentane as alkylation reagent). $^1$H NMR (400 MHz, CDCl$_3$) δ 7.73 (s, 1H), 7.55 (s, 1H), 7.48 (s, 1H), 7.31 (m, 1H), 7.07 (m, 1H), 6.88 (s, 1H), 6.08 (m, 1H), 4.64 (m, 1H), 2.04 (m, 2H), 1.98 (m, 2H), 1.86 (d, J=8 Hz, 3H), 1.73 (m, 2H); LCMS: 435 [M+1]; c-Met Ki: 0.02 μM.

Example 13

3-[(R)-1-(2,6-Dichloro-3-fluoro-phenyl)-ethoxy]-5-(1-piperidin-4-yl-1H-pyrazol-4-yl)-pyridin-2-ylamine

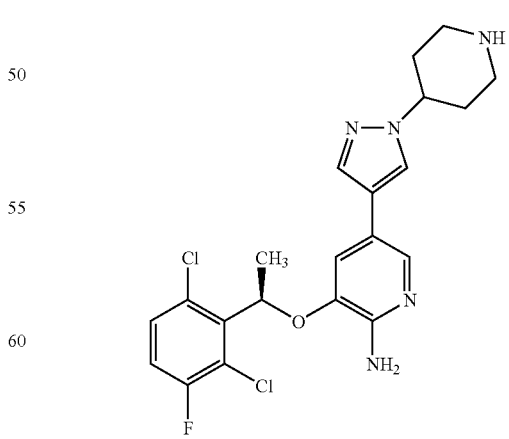

The title compound was prepared according to procedure 62. $^1$H NMR (400 MHz, CDCl$_3$) δ 7.69 (s, 1H), 7.56 (s, 1H), 7.50 (s, 1H), 7.32 (m, 1H), 7.07 (m, 1H), 6.87 (m, 1H), 6.07 (m, 1H), 5.25 (bs, 2H), 4.30 (m, 1H), 3.41 (m, 2H), 2.96 (m, 2H), 2.26 (m, 2H), 2.12 (m, 2H), 1.86 (d, J=8 Hz, 3H); LCMS: 450 [M+1]; c-Met Ki: 0.003 µM.

Example 14

3-[(R)-1-(2,6-Dichloro-3-fluoro-phenyl)-ethoxy]-5-(1-piperidin-4-yl-1H-pyrazol-4-yl)-pyrazin-2-ylamine

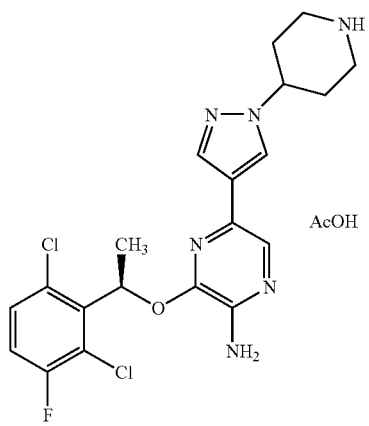

The title compound was prepared according to procedure 66. $^1$H NMR (400 MHz, DMSO-d$_6$) δ 7.86 (s, 1H), 7.76 (s, 1H), 7.63 (m, 2H), 7.54 (m, 1H), 7.37 (t, 1H), 6.46 (q, 1H), 6.15 (s, 1H), 4.10 (m, 1H), 3.01 (m, 2H), 1.95 (m, 2H), 1.85 (s, 2H), 1.75 (d, 3H), 1.67 (dd, 1H); LCMS: 451 [M+1]; c-Met Ki: 0.010 µM.

Example 15

3-[(R)-1-(2,6-Dichloro-3-fluoro-phenyl)-ethoxy]-5-(1H-pyrazol-4-yl)-pyrazin-2-ylamine

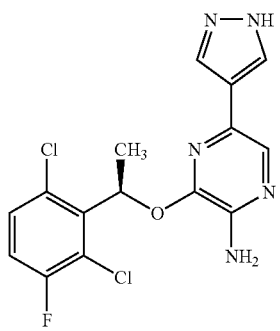

The title compound was prepared according to procedure 3 using 5-bromo-3-[(R)-1-(2,6-dichloro-3-fluoro-phenyl)-ethoxy]-pyrazin-2-ylamine and 4-(4,4,5,5-Tetramethyl-[1,3,2]dioxaborolan-2-yl)-pyrazole-1-carboxylic acid tert-butyl ester. $^1$H NMR (400 MHz, DMSO-d$_6$) δ 12.81 (s, 1H), 7.79 (s, 1H), 7.48 (m, 1H), 7.36 (t, 1H), 6.48 (q, 1H), 6.12 (s, 2H), 1.75 (d, 3H); LCMS: 368 [M+1]; c-Met Ki: 0.065 µM.

Example 16

1-[4-(4-{5-Amino-6-[(R)-1-(2,6-dichloro-3-fluoro-phenyl)-ethoxy]-pyrazin-2-yl}-pyrazol-1-yl)-piperidin-1-yl]-2-hydroxy-ethanone

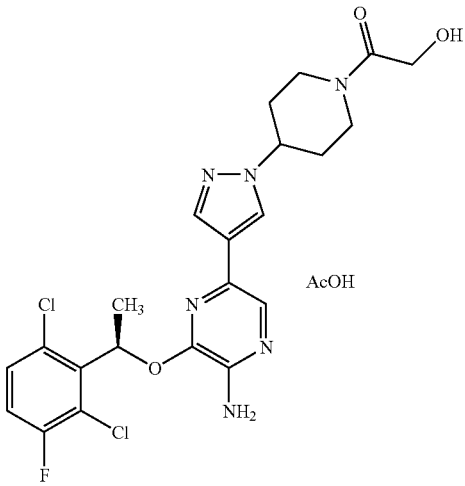

The title compound was prepared according to procedures 62 and 63, using 5-bromo-3-[(R)-1-(2,6-dichloro-3-fluoro-phenyl)-ethoxy]-pyrazin-2-ylamine as the starting material. $^1$H NMR (400 MHz, DMSO-d$_6$) δ 7.91 (s, 1H), 7.76 (s, 1H), 7.64 (s, 1H), 7.49 (m, 1H), 7.36 (t, 1H), 6.46 (q, 1H), 6.15 (s, 2H), 4.57 (br, 1H), 4.40 (m, 2H), 4.12 (br, 2H), 3.77 (m, 1H), 3.35 (m, 2H), 3.43 (m, 1H), 3.16 (m, 2H), 1.75 (d, 3H); LCMS: 509 [M+1]; c-Met Ki: 0.015 µM.

Example 17

3-[(R)-1-(2,6-Dichloro-3-fluoro-phenyl)-ethoxy]-5-[1-(1-methyl-piperidin-4-yl)-1H-pyrazol-4-yl]-pyrazin-2-ylamine

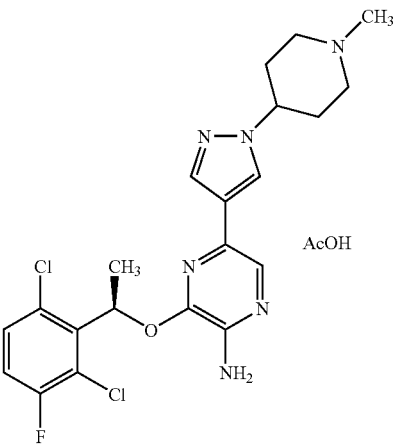

The title compound was prepared according to procedure 62 using 5-bromo-3-[(R)-1-(2,6-dichloro-3-fluoro-phenyl)-ethoxy]-pyrazin-2-ylamine and 4-(4-bromo-pyrazol-1-yl)-1-methy-piperidine (prepared according to general procedure 11). $^1$H NMR (400 MHz, DMSO-d$_6$) δ 7.88 (s, 1H), 7.76 (s, 1H), 7.64 (s, 1H), 7.49 (m, 1H), 7.36 (t, 1H), 6.46 (q, 1H), 6.15 (s, 2H), 4.02 (m, 1H), 2.84 (m, 2H), 2.19 (s, 3H), 2.00 (m, 4H), 1.85 (m, 3H), 1.75 (d, 3H); LCMS: 465 [M+1]; c-Met Ki: 0.03 μM.

Example 18

1-[4-(4-{5-Amino-6-[(R)-1-(2,6-dichloro-3-fluoro-phenyl)-ethoxy]-pyrazin-2-yl}-pyrazol-1-yl)-piperidin-1-yl]-2-dimethylamino-ethanone

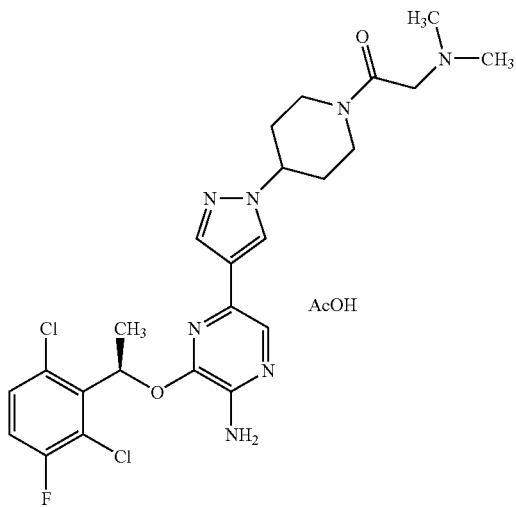

The title compound was prepared according to procedure 63 using 3-[(R)-1-(2,6-dichloro-3-fluorophenyl)-ethoxy]-5-(1-piperidin-4-yl-1H-pyrazol-4-yl)-pyrazin-2-ylamine coupled with dimethylamino-acetic acid in the presence of HOBt/EDC/triethylamine in DMF as described in procedure 5 using 5-bromo-3-[(R)-1-(2,6-dichloro-3-fluoro-phenyl)-ethoxy]-pyrazin-2-ylamine as the starting material. $^1$H NMR (400 MHz, DMSO-d$_6$) δ 7.90 (s, 1H), 7.76 (s, 1H), 7.65 (s, 1H), 7.49 (m, 1H), 7.36 (t, 1H), 6.47 (q, 1H), 6.15 (s, 2H), 4.39 (m, 1H), 4.16 (m, 1H), 3.16 (m, 2H), 3.02 (m, 1H), 2.75 (m, 1H), 2.19 (s, 6H), 2.01 (m, 2H), 1.88 (s, 1H), 1.75 (d, 3H); LCMS: 536 [M+1]; c-Met Ki: 0.015 μM.

Example 19

3-[(R)-1-(2-Chloro-3,6-difluoro-phenyl)-ethoxy]-5-(1-piperidin-4-yl-1H-pyrazol-4-yl)-pyridin-2-ylamine

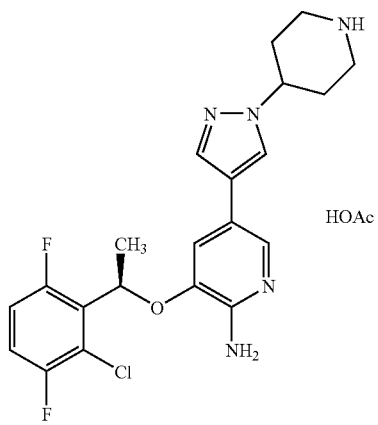

The title compound was prepared according to procedure 62 using 5-bromo-3-[(R)-1-(2-chloro-3,6-difluoro-phenyl)-ethoxy]-pyridin-2-ylamine as starting material (according to the methods for the synthesis of 5-bromo-3-[1-(2,6-dichloro-3-fluoro-phenyl)-ethoxy]-pyridin-2-ylamine from (S)-1-(2-chloro-3,6-difluoro-phenyl)-ethanol, obtained from Syn-Chem, Inc.). $^1$H NMR (400 MHz, DMSO-d6) δ 7.88 (s, 1H), 7.70 (s, 1H), 7.50 (s, 1H), 7.38 (m, 1H), 7.25 (m, 1H), 6.99 (s, 1H), 5.88 (m, 1H), 5.48 (bs, 2H), 4.08 (m, 1H), 2.96 (m, 2H), 2.53 (m, 1H), 2.45 (m, 1H), 1.89 (m, 1H), 1.80 (m, 4H), 1.67 (m, 4H); LCMS: 434 [M+1]; c-Met Ki: 0.09 μM.

Biological Examples

It will be appreciated that, in any given series of compounds, a range of biological activities will be observed. In its presently preferred aspects, this invention relates to novel compounds capable of modulating, regulating and/or inhibiting protein kinase activity. The following assays may be employed to select those compounds demonstrating the optimal degree of the desired activity.

Assay Procedures

The following in vitro assay may be used to determine the level of activity and effect of the different compounds of the present invention on one or more of the PKs. Similar assays can be designed along the same lines for any PK using techniques well known in the art. A literature reference is provided (Technikova-Dobrova Z, Sardanelli A M, Papa S FEBS Lett. 1991 Nov. 4; 292: 69-72).

The general procedure is as follows: compounds and kinase assay reagents are introduced into test wells. The assay is initiated by addition of the kinase enzyme. Enzyme inhibitors reduce the measured activity of the enzyme.

In the continuous-coupled spectrophotometric assay the time-dependent production of ADP by the kinase is determined by analysis of the rate of consumption of NADH by measurement of the decrease in absorbance at 340 nm. As the PK produces ADP it is re-converted to ATP by reaction with phosphoenol pyruvate and pyruvate kinase. Pyruvate is also produced in this reaction. Pyruvate is subsequently converted to lactate by reaction with lactate dehydrogenase, which simultaneously converts NADH to NAD. NADH has a measurable absorbance at 340 nm whereas NAD does not.

The presently preferred protocol for conducting the continuous-coupled spectrophotometric experiments for specific PKs is provided below. However, adaptation of this protocol for determining the activity of compounds against other RTKs, as well as for CTKs and STKs, is well within the scope of knowledge of those skilled in the art.

HGFR Continuous-Coupled Spectrophotometric Assay

This assay analyzes the tyrosine kinase activity of HGFR on the Met-2 substrate peptide, a peptide derived from the activation loop of the HGFR.

Materials and Reagents:
1. HGFR enzyme from Upstate (Met, active) Cat. # 14-526
2. Met-2 Peptide (HGFR Activation Loop) Ac-ARDMY-DKEYYSVHNK (MW=1960). Dissolve up in 200 mM HEPES, pH 7.5 at 10 mM stock.
3. 1 M PEP (phospho-enol-pyruvate) in 200 mM HEPES, pH 7.5
4. 100 mM NADH (B-Nicotinamide Adenine Dinucleotide, Reduced Form) in 200 mM HEPES, pH 7.5
5. 4 M MgCl$_2$ (Magnesium Chloride) in ddH$_2$O
6. 1 M DTT (Dithiothreitol) in 200 mM HEPES, pH 7.5
7. 15 Units/mL LDH (Lactic Dehydrogenase)
8. 15 Units/mL PK (Pyruvate Kinase)
9. 5M NaCl dissolved in ddH$_2$O 10. Tween-20 (Protein Grade) 10% Solution
11. 1 M HEPES buffer: (N-[2-Hydroxethyl]piperazine-N-[2-ethanesulfonic acid]) Sodium Salt. Dissolve in ddH2O, adjust pH to 7.5, bring volume to 1 L. Filter at 0.1 μm.
12. HPLC Grade Water; Burdick and Jackson #365-4, 1×4 liters (or equivalent)
13. 100% DMSO (SIGMA)
14. Costar # 3880—black clear flat bottom half area plates for $K_i$ determination and % inhibition
15. Costar # 3359—96 well polypropylene plates, round bottom for serial dilutions
16. Costar # 3635—UV-plate clear flat bottom plates for % inhibition
17. Beckman DU-650 w/micro cell holders
18. Beckman 4-position micro cell cuvette Procedure:

Prep Dilution Buffer (DB) for Enzyme (For 30 mL prep)
1. DB final concentration is 2 mM DTT, 25 mM NaCl$_2$, 5 mM MgCl$_2$, 0.01% Tween-20, and 50 mM HEPES buffer, pH 7.5.
2. Make up 50 mM HEPES by adding 1.5 mL 1 M HEPES into 28.1 mL of ddH$_2$O. Add rest of the reagents. Into 50 mL conical vial, add 60 μL of 1M DTT, 150 μL 5M NaCl$_2$, 150 μL 1M MgCl$_2$, and 30 μL of 10% Tween-20 to give total volume of 30 mL.
3. Vortex for 5-10 seconds.
4. Aliquot out DB at 1 mL/tube and label tubes as "DB HGFR"
5. Note: This can be prepared and stored ahead of time.
6. Freeze un-used aliquots in microcentrifuge tubes at −20° C. freezer.

Prep Compounds
1. For compound dilution plate, add 4 μL of 10 mM stock into column 1 of plate, and bring volume to 100 μL with 100% DMSO.
2. Set up the Precision 2000 dilution method. A final concentration of 200 μM compound in 50% DMSO, 100 mM HEPES (1:2 serial dilution).

Prep Coupled Enzymatic Buffer:
1. Final concentration in assay:

| Reagent (Stock Conc.) | Final Conc. In Assay |
|---|---|
| a. PEP (1 M) | 1 mM |
| b. NADH (100 mM) | 300 μM |
| c. MgCl$_2$ (4 M) | 20 mM |
| d. DTT (1 M) | 2 mM |
| e. ATP (500 mM) | 300 μM |
| f. HEPES 200 mM (pH 7.5) | 100 mM |
| g. Pyruvate Kinase (PK) | 15 units/mL |
| h. Lactic Dehydrogenase (LDH) | 15 units/mL |
| i. Met-2 peptide (10 mM) | 0.500 mM |
| j. HGFR | 50 nM |

2. For a 10 mL reaction buffer add 10 μL of 1M PEP, 33 μL of 100 mM NADH, 50 μL of 4M MgCl$_2$, 20 μL of 1M DTT, 6 μL of 500 mM ATP, and 500 μL of 10 mM Met-2 peptide into 100 mM HEPES buffer pH 7.5 and vortex/mix.
3. Add coupling enzymes, LDH and PK, into reaction mix. Mix by gentle inversion.

Running Samples
1. Spectrophotometer settings:

| | |
|---|---|
| i. Absorbance wavelength (λ): | 340 nm |
| ii. Incubation time: | 10 min |
| iii. Run time: | 10 min |
| iv. Temperature: | 37° C. |

2. Add 85 μL of CE reaction mix into each well of assay plate.
3. Add 5 μL of diluted compound into a well of the assay plate.
4. Add 5 μL of 50% DMSO for negative control into last column of assay plate.
5. Mix with multi-channel pipettor or orbital shaker.
6. Pre-incubate for 10 minutes at 37° C.
7. Add 10 μL of 500 nM HGFR to each well of assay plate; the final HGFR concentration is 50 nM in a total final volume of 100 μL.
8. Measure activity for 10 minutes at λ=340 nm and 37° C.

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359-371). General procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. General procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

MET Transphosphorylation Assay

This assay is used to measure phosphotyrosine levels on a poly(glutamic acid: tyrosine, 4:1) substrate as a means for identifying agonists/antagonists of met transphosphorylation of the substrate.

Materials and Reagents:
1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 mL PBS, filter through a 4 μm filter.
6. Purified GST fusion protein containing the Met kinase domain, SUGEN, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 mL, mix 10 mL 1M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4× ATP Reaction Mixture: for 10 mL, mix 0.4 mL 1 M manganese chloride and 0.02 mL 0.1 M ATP in 9.56 mL $dH_2O$.
12. 4× Negative Controls Mixture: for 10 mL, mix 0.4 mL 1 M manganese chloride in 9.6 mL $dH_2O$.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. $ABTS/H_2O_2$: mix 15 mL ABST solution with 2 μL $H_2O_2$ five minutes before use.
20. 0.2 M HCl Procedure:
1. Coat ELISA plates with 2 μg Poly(Glu-Tyr) in 100 μL PBS, hold overnight at 4° C.
2. Block plate with 150 μL of 5% BSA/PBS for 60 min.
3. Wash plate twice with PBS then once with 50 mM Hepes buffer pH 7.4.
4. Add 50 μL of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in $dH_2O$) for controls to plate.
6. Incubate the kinase/compound mixture for 15 minutes.
7. Add 25 μL of 40 mM $MnCl_2$ to the negative control wells.
8. Add 25 μL $ATP/MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of $ABTS/H_2O_2$ solution to each well.
16. If necessary, stop the development reaction with the addition of 100 μL of 0.2M HCl per well.
17. Read plate on Dynatech MR7000 ELISA reader with the test filter at 410 nM and the reference filter at 630 nM.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:
1. The appropriate ligand.
2. The appropriate engineered cells.
3. BrdU Labeling Reagent: 10 mM, in PBS, pH7.4 (Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 μM) for 1.5 hours.
5. After incubation with labeling reagent, the medium is removed by decanting and tapping the inverted plate on a paper towel. FixDenat solution is added (50 μl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 μL/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 μL/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 μl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

HGF-Induced BrdU Incorporation Assay

Materials and Reagents:
1. Recombinant human HGF (Cat. No. 249-HG, R&D Systems, Inc. USA).
2. BxPC-3 cells (ATCC CRL-1687).

Remaining Materials and Reagents, as above.

Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 μL serum-free medium (RPMI with 0.1% BSA) for 24 hours.
3. On day 3, 25 μL containing ligand (prepared at 1 μg/mL in RPMI with 0.1% BSA; final HGF conc. is 200 ng/mL) and test compounds are added to the cells. The negative control wells receive 25 μL serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 μM, and 1:3 dilutions are used (i.e. final test compound concentration range is 0.137-100 μM).
4. After 18 hours of ligand activation, 12.5 μL of diluted BrdU labeling reagent (1:100 in RPMI, 0.1% BSA) is added to each well and the cells are incubated with BrdU (final concentration is 10 μM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 μL/well) and the plate is incubated for 90 minutes at room temperature on a plate shaker.
8. Same as General Procedure.
9. Same as General Procedure.
10. Same as General Procedure.

Cellular HGFR Autophosphorylation Assay

A549 cells (ATCC) were used in this assay. Cells were seeded in the growth media (RPMI+10% FBS) into 96 well plates and cultured overnight at 37° C. for attachment. Cells were exposed to the starvation media (RPMI+0.05% BSA). Dilutions of the inhibitors were added to the plates and incubated at 37° C. for 1 hour. Cells were then stimulated by adding 40 ng/mL HGF for 15 minutes. Cells were washed once with 1 mM $Na_3VO_4$ in HBSS and then lysed. The lysates were diluted with 1 mM $Na_3VO_4$ in HBSS and transferred to a 96 well goat ant-rabbit coated plate (Pierce) which was pre-coated with anti-HGFR antibody (Zymed Laboratories). The plates were incubated overnight at 4° C. and washed with 1% Tween 20 in PBS for seven times. HRP-PY20 (Santa Cruz) was diluted and added to the plates for 30 minutes incubation. Plates were then washed again and TMB peroxidase substrate (Kirkegaard & Perry) was added and incubated for 10 minutes. The reaction was then stopped by adding 0.09N $H_2SO_4$. Plates were measured at OD-450 nm using a spectrophotometer. $IC_{50}$ values were calculated by curve fitting using a four-parameter analysis.

Compounds of the invention were measured for HGFR inhibition activity; the data are shown in each Example. Ki data were obtained using the HGFR Continuous-Coupled Spectrophotometric Assay, and $IC_{50}$ data were obtained using the Cellular HGFR Autophosphorylation Assay, both of which are described above.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

All references cited herein, including any priority documents, are hereby incorporated by reference in their entireties.

We claim:
1. A compound of the formula:

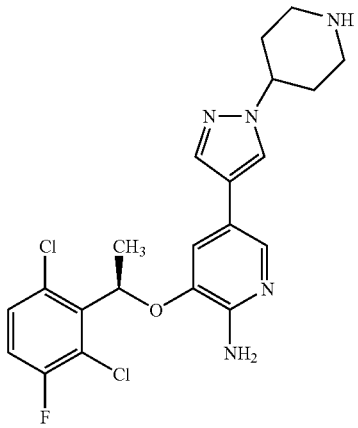

or a pharmaceutically acceptable salt thereof.
2. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,858,643 B2 |
| APPLICATION NO. | : 11/212331 |
| DATED | : December 28, 2010 |
| INVENTOR(S) | : Jingrong Cui et al. |

It is certified that error appears in the above-identified patent and that said Letters Patent is hereby corrected as shown below:

In the specification:

Column 118, line 39, delete "procedure 11" and insert --procedure 65--

Column 139, line 28, delete "procedure 11" and insert --procedure 65--

Column 140, line 31, delete "procedure 11" and insert --procedure 65--

Column 142, lines 66-67, delete "procedure 11" and insert --procedure 65--

Signed and Sealed this
Twenty-seventh Day of October, 2015

Michelle K. Lee
*Director of the United States Patent and Trademark Office*